US011384345B2

(12) United States Patent
Delarue et al.

(10) Patent No.: US 11,384,345 B2
(45) Date of Patent: Jul. 12, 2022

(54) DNA POLYMERASE THETA MUTANTS, METHODS OF PRODUCING THESE MUTANTS, AND THEIR USES

(71) Applicants: INSTITUT PASTEUR, Paris (FR); CENTRE NATIONAL DE LA RECHERCHE SCIENTIFIQUE, Paris (FR)

(72) Inventors: Marc Delarue, Versailles (FR); Volahasina (Irina) Randrianjatovo Gbalou, Fleury-Merogis (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/648,532

(22) PCT Filed: Sep. 20, 2018

(86) PCT No.: PCT/EP2018/075510
§ 371 (c)(1),
(2) Date: Mar. 18, 2020

(87) PCT Pub. No.: WO2019/057835
PCT Pub. Date: Mar. 28, 2019

(65) Prior Publication Data
US 2020/0224181 A1 Jul. 16, 2020

Related U.S. Application Data

(60) Provisional application No. 62/560,693, filed on Sep. 20, 2017.

(51) Int. Cl.
*C12N 15/10* (2006.01)
*C12N 9/12* (2006.01)
(52) U.S. Cl.
CPC ......... *C12N 9/1252* (2013.01); *C12N 15/102* (2013.01); *C12N 15/1093* (2013.01); *C12Y 207/07007* (2013.01)
(58) Field of Classification Search
CPC .............. C12N 9/1252; C12N 15/102; C12N 15/1093; C12Y 207/07007
See application file for complete search history.

(56) References Cited

U.S. PATENT DOCUMENTS

2020/0370027 A1\* 11/2020 Ybert ............. C12Y 207/07007

FOREIGN PATENT DOCUMENTS

WO 2009/126632 A1 10/2009
WO 2017/075421 A1 5/2017

OTHER PUBLICATIONS

International Search Report and Written Opinion, PCT/EP2018/075510, dated Dec. 19, 2018.
(Continued)

*Primary Examiner* — Jeremy C Flinders
(74) *Attorney, Agent, or Firm* — Arrigo, Lee, Guttman & Mouta-Bellum LLP

(57) ABSTRACT

The invention relates to mutant DNA polymerases of the Pol theta subfamily capable of performing non-templated nucleic acid extension, or of a functional fragment of such a polymerase, methods of producing these mutant DNA polymerases, kits and methods of using these mutant DNA polymerases.

17 Claims, 33 Drawing Sheets

Specification includes a Sequence Listing.

(56) References Cited

OTHER PUBLICATIONS

Sergey Lapa, et al., "The toolbox for modified aptamers," Molecular Biotechnology, vol. 58, No. 2, pp. 79-92 (2015).
Tatiana Kent, et al., "DNA polymerase [theta] specializes in incorporating synthetic expanded-size (xDNA) nucleotides," Nucleic Acids Research, vol. 44, No. 9, pp. 9381-9392 (2016).

* cited by examiner

FIGURE 1A

```
                605            610             615
                 •              •               •
Taq pol I    L L V A L D Y S Q I E L R V L A H Human pol θ  S I L A A D Y S Q L E L R I L A H
                 •              •               •
               2325           2330            2335
```

FIGURE 2A-C

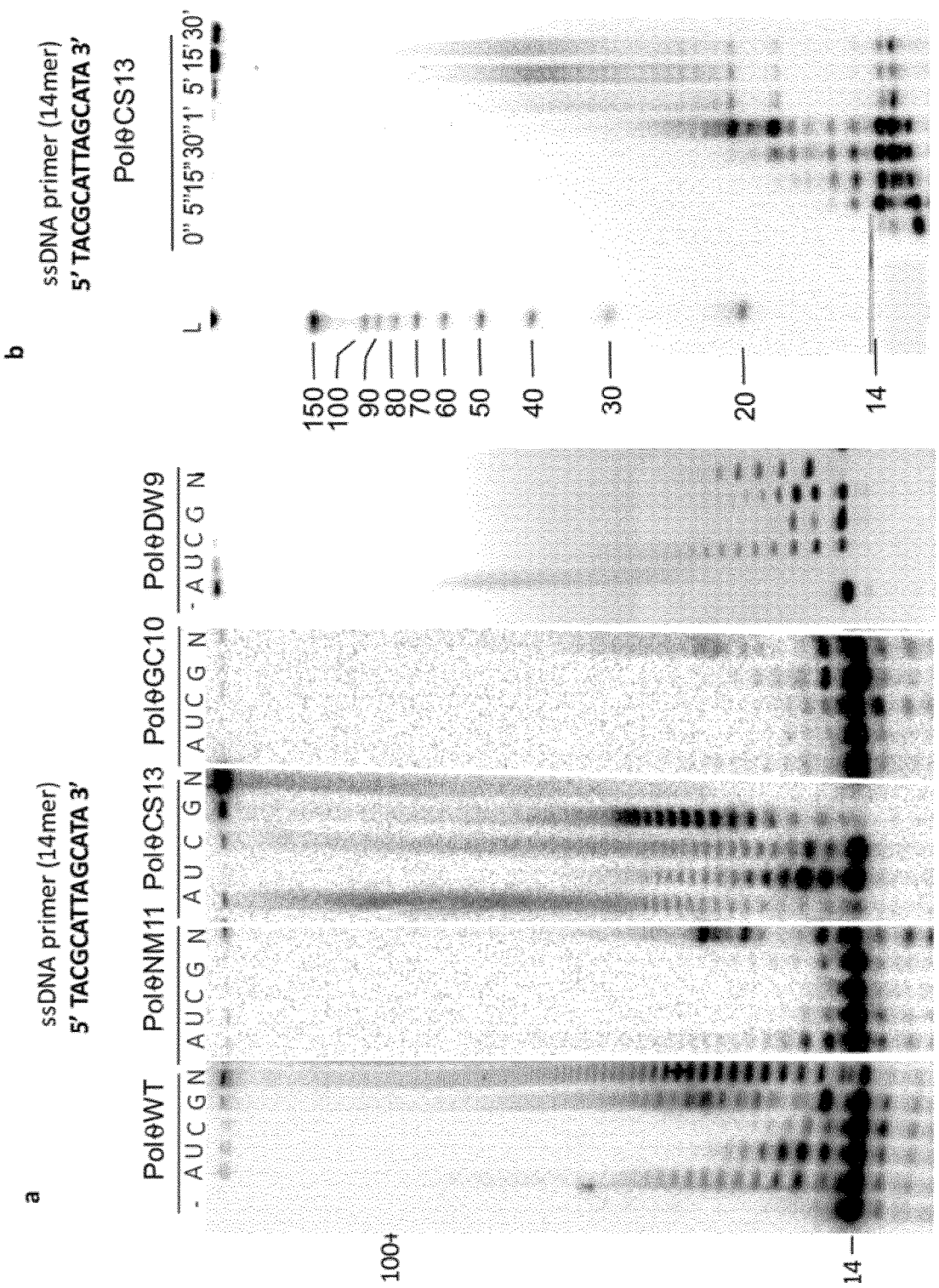
FIGURE 4A-B

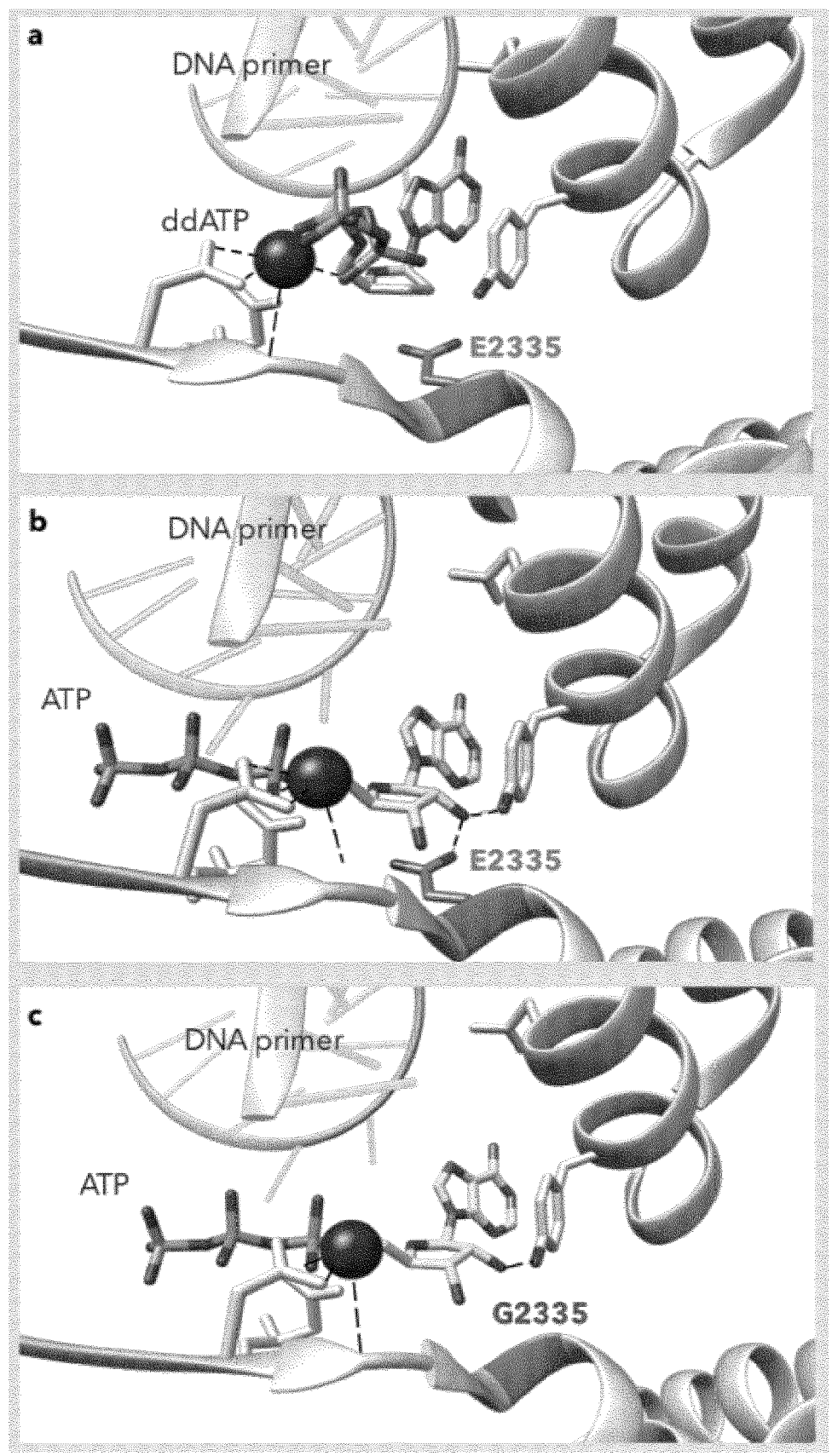
FIGURE 5A-C

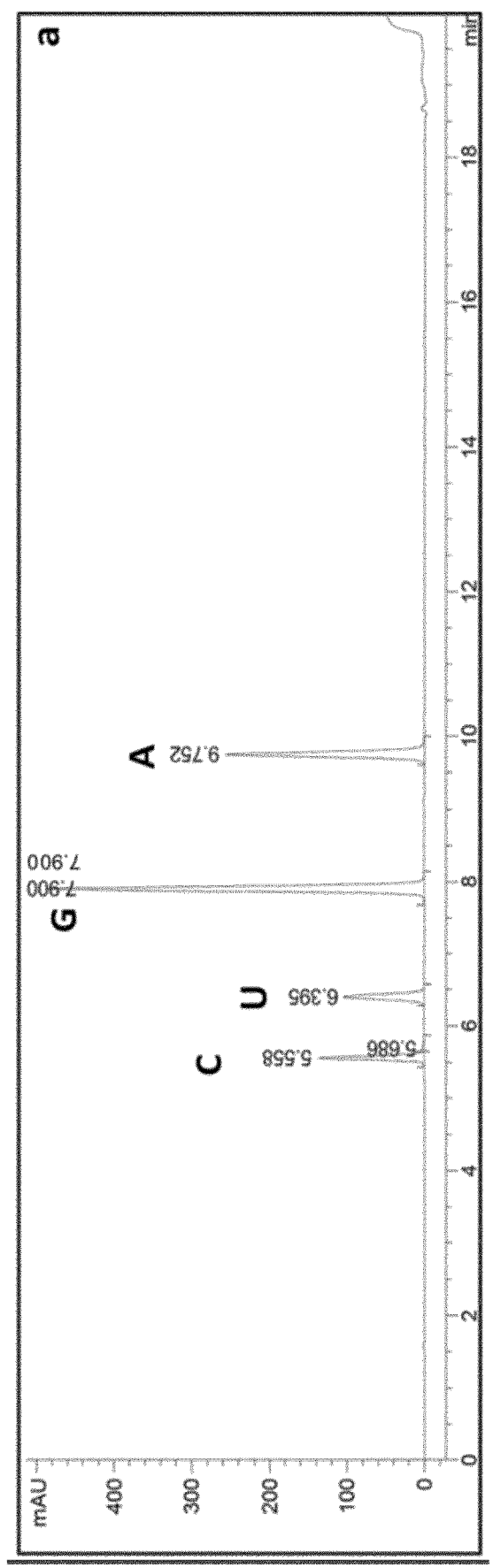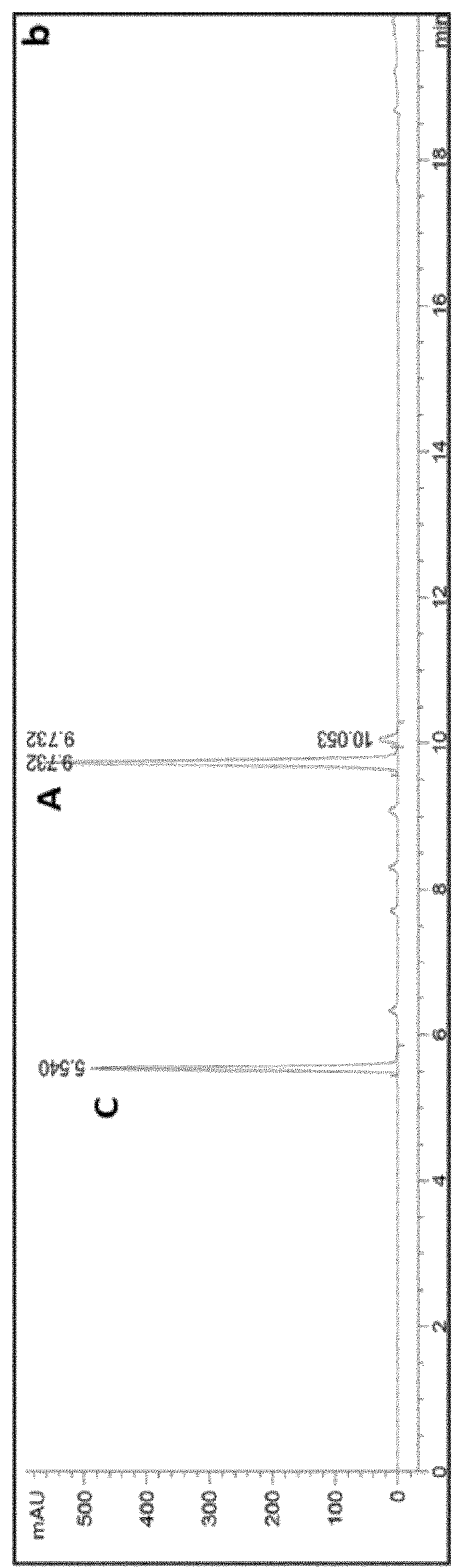
FIGURE 6 A-B

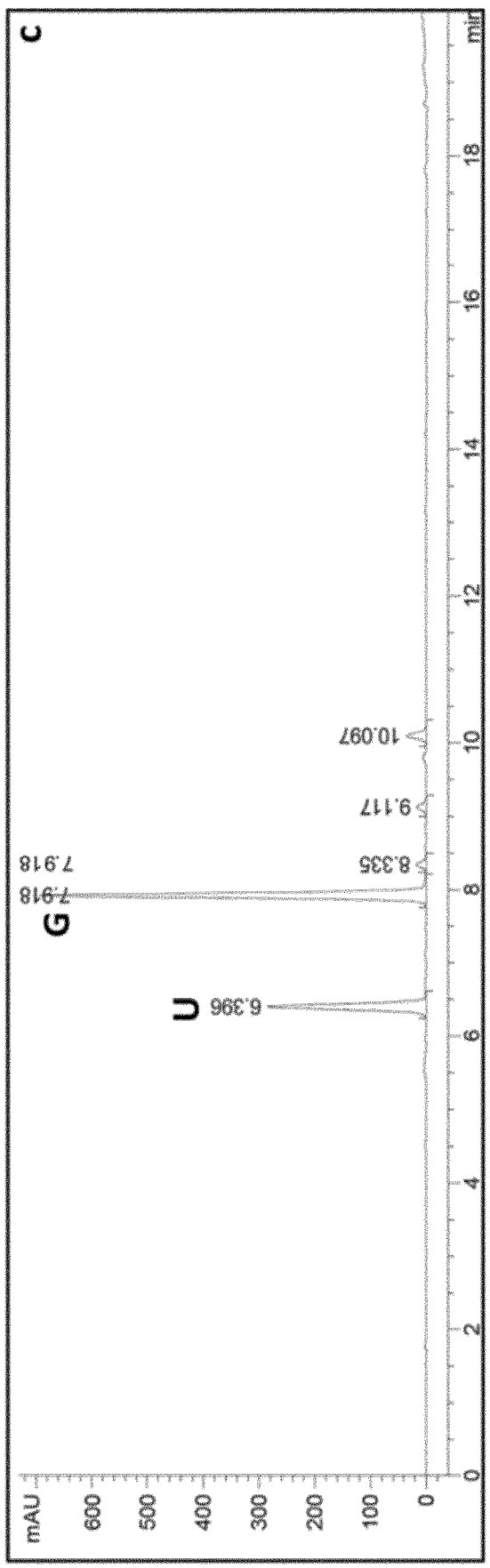
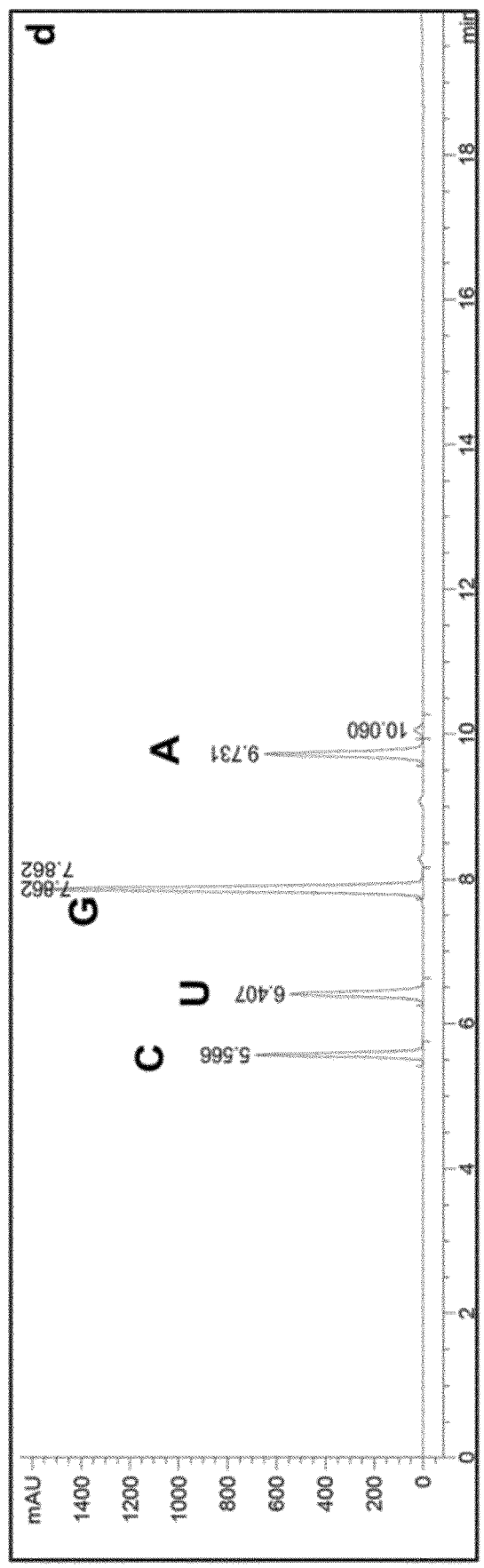
FIGURE 6 C-D

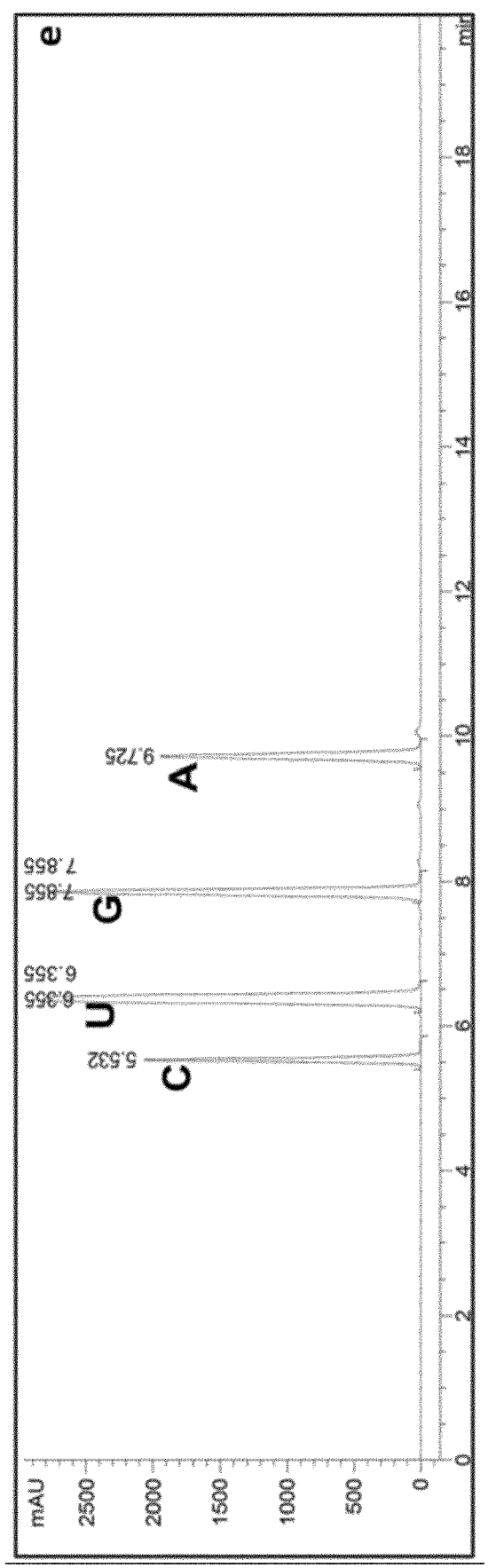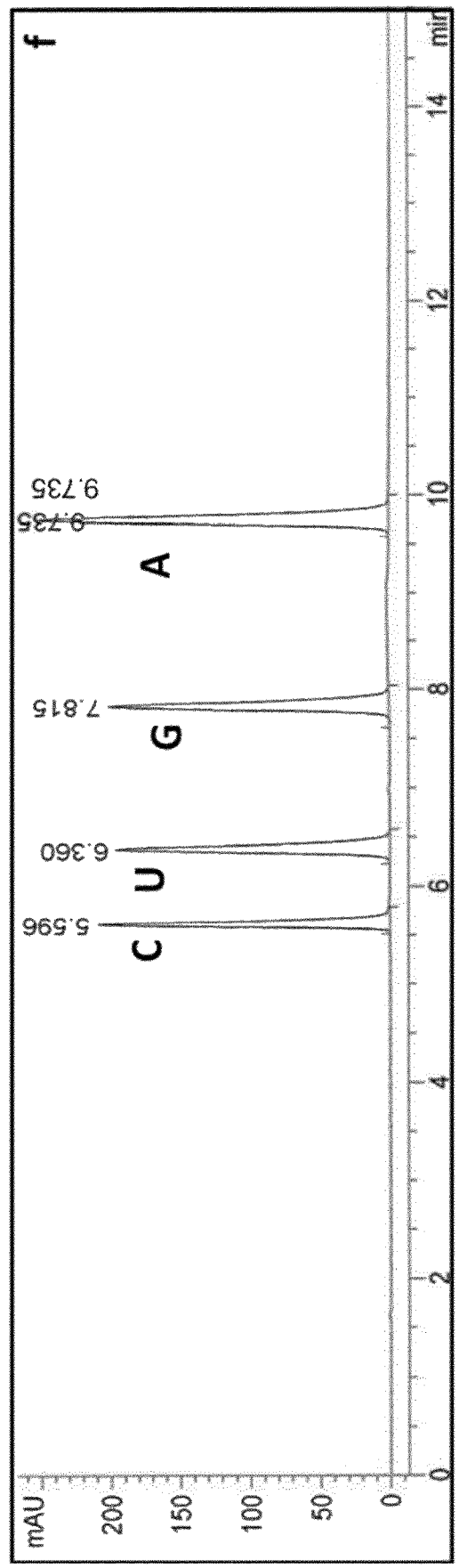
FIGURE 6 E-F

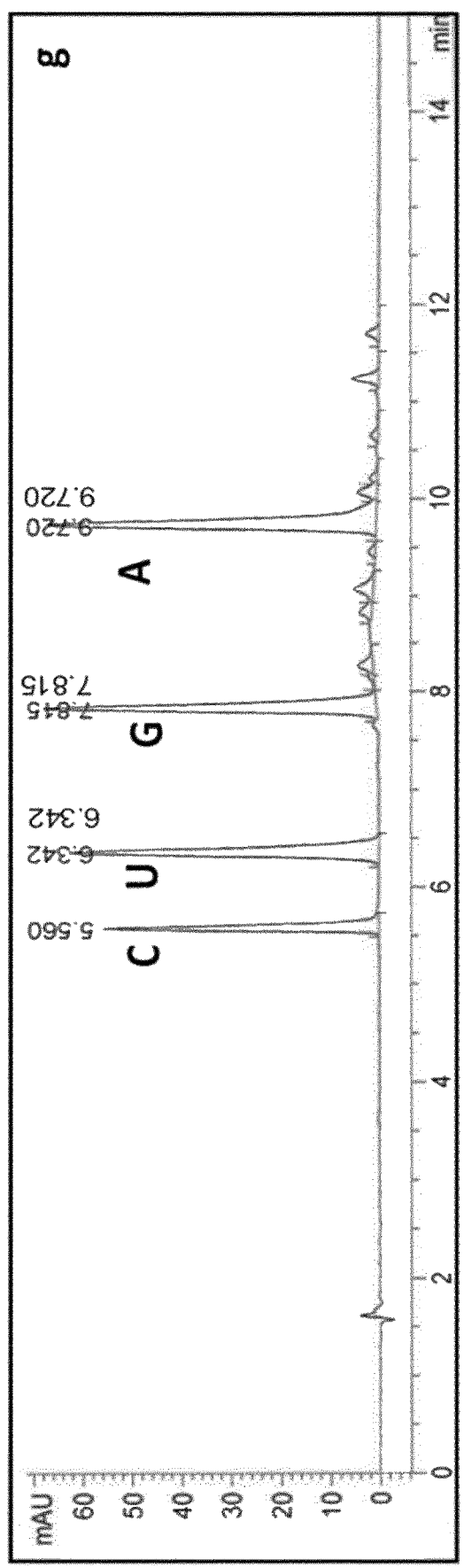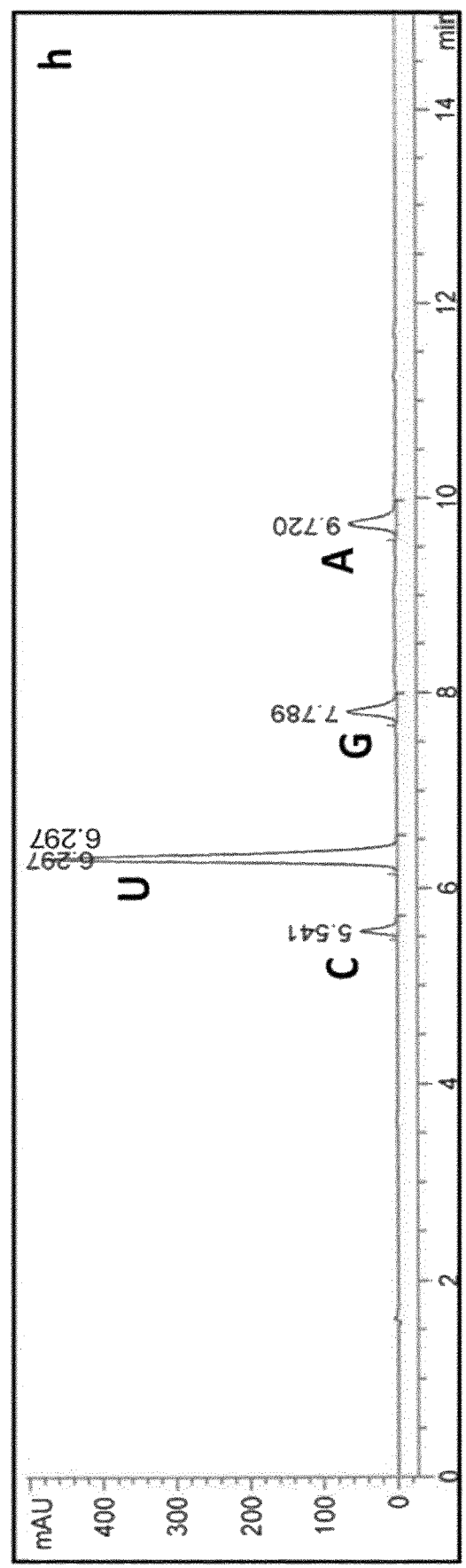
FIGURE 6 G-H

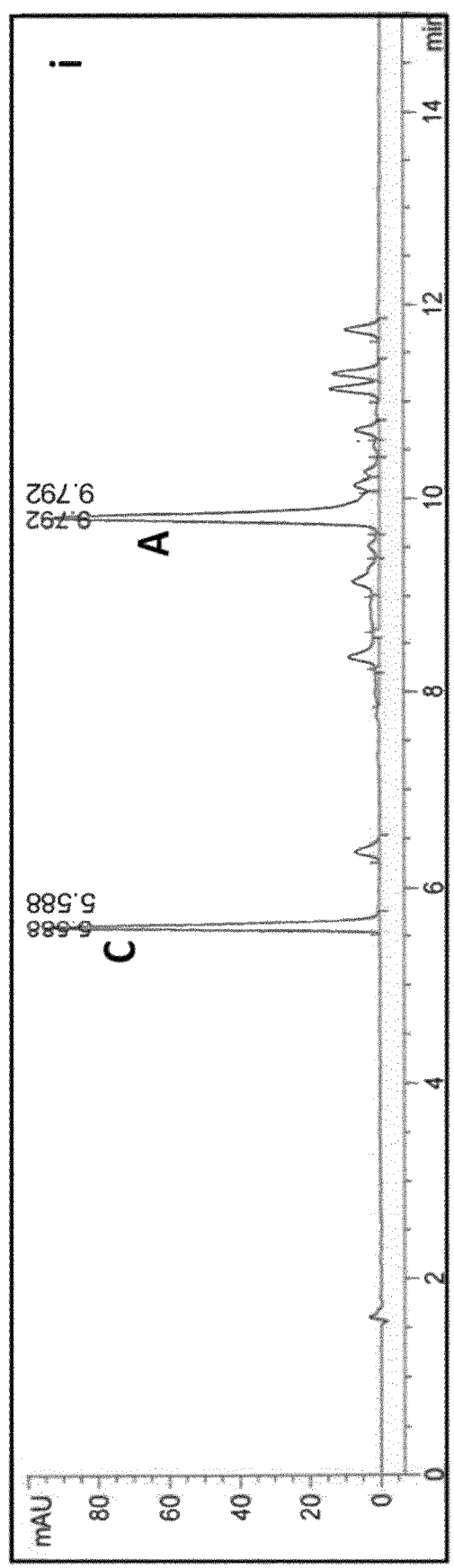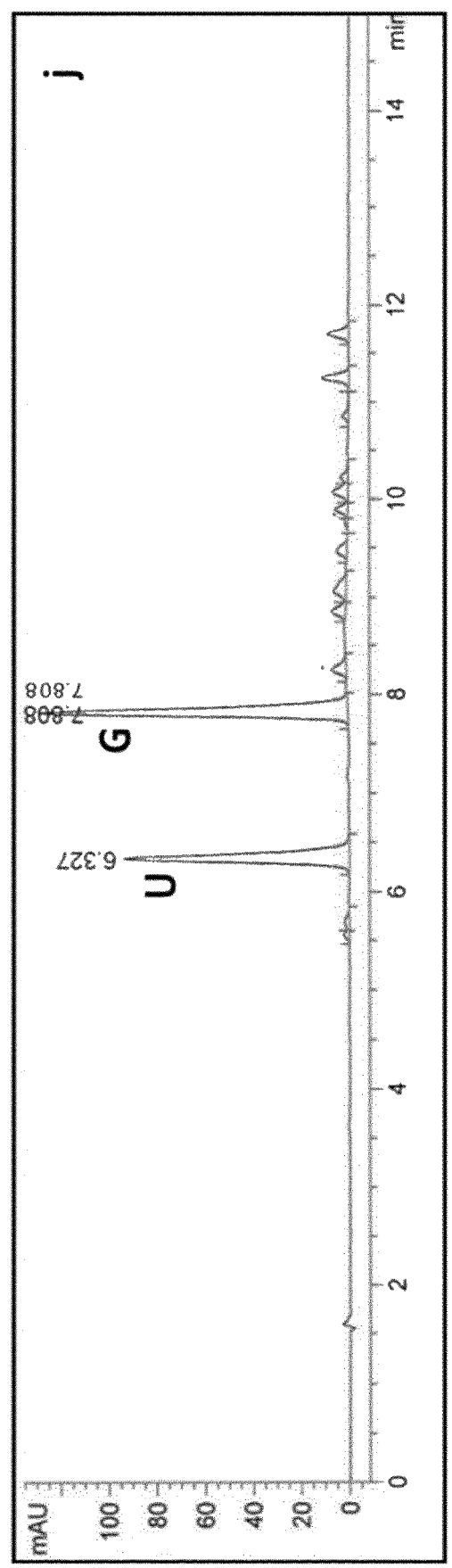
FIGURE 6 I-J

SEQUENCE LISTING

<160> NUMBER OF SEQ ID NOS: 26

<210> SEQ ID NO 1
<211> LENGTH: 2590
<212> TYPE: PRT
<213> ORGANISM: Homo sapiens

<400> SEQUENCE: 1

Met Asn Leu Leu Arg Arg Ser Gly Lys Arg Arg Ser Glu Ser Gly
1               5                   10                  15

Ser Asp Ser Phe Ser Gly Ser Gly Gly Asp Ser Ser Ala Ser Pro Gln
                20                  25                  30

Phe Leu Ser Gly Ser Val Leu Ser Pro Pro Gly Leu Gly Arg Cys
            35                  40                  45

Leu Lys Ala Ala Ala Ala Gly Glu Cys Lys Pro Thr Val Pro Asp Tyr
        50                  55                  60

Glu Arg Asp Lys Leu Leu Leu Ala Asn Trp Gly Leu Pro Lys Ala Val
65                  70                  75                  80

Leu Glu Lys Tyr His Ser Phe Gly Val Lys Met Phe Glu Trp Gln
            85                  90                  95

Ala Glu Cys Leu Leu Leu Gly Gln Val Leu Glu Gly Lys Asn Leu Val
                100                 105                 110

Tyr Ser Ala Pro Thr Ser Ala Gly Lys Thr Leu Val Ala Glu Leu Leu
            115                 120                 125

Ile Leu Lys Arg Val Leu Glu Met Arg Lys Lys Ala Leu Phe Ile Leu
        130                 135                 140

Pro Phe Val Ser Val Ala Lys Glu Lys Lys Tyr Tyr Leu Gln Ser Leu
145                 150                 155                 160

Phe Gln Glu Val Gly Ile Lys Val Asp Gly Tyr Met Gly Ser Thr Ser
                165                 170                 175

Pro Ser Arg His Phe Ser Ser Leu Asp Ile Ala Val Cys Thr Ile Glu
            180                 185                 190

Arg Ala Asn Gly Leu Ile Asn Arg Leu Ile Glu Glu Asn Lys Met Asp
        195                 200                 205

-continued

```
Leu Leu Gly Met Val Val Asp Glu Leu His Met Leu Gly Asp Ser
        210                 215                 220

His Arg Gly Tyr Leu Leu Glu Leu Leu Thr Lys Ile Cys Tyr Ile
225                 230                 235                 240

Thr Arg Lys Ser Ala Ser Cys Gln Ala Asp Leu Ala Ser Ser Leu Ser
                245                 250                 255

Asn Ala Val Gln Ile Val Gly Met Ser Ala Thr Leu Pro Asn Leu Glu
                260                 265                 270

Leu Val Ala Ser Trp Leu Asn Ala Glu Leu Tyr His Thr Asp Phe Arg
                275                 280                 285

Pro Val Pro Leu Leu Glu Ser Val Lys Val Gly Asn Ser Ile Tyr Asp
        290                 295                 300

Ser Ser Met Lys Leu Val Arg Glu Phe Glu Pro Met Leu Gln Val Lys
305                 310                 315                 320

Gly Asp Glu Asp His Val Val Ser Leu Cys Tyr Glu Thr Ile Cys Asp
                325                 330                 335

Asn His Ser Val Leu Leu Phe Cys Pro Ser Lys Lys Trp Cys Glu Lys
                340                 345                 350

Leu Ala Asp Ile Ile Ala Arg Glu Phe Tyr Asn Leu His His Gln Ala
        355                 360                 365

Glu Gly Leu Val Lys Pro Ser Glu Cys Pro Val Ile Leu Glu Gln
        370                 375                 380

Lys Glu Leu Leu Glu Val Met Asp Gln Leu Arg Arg Leu Pro Ser Gly
385                 390                 395                 400

Leu Asp Ser Val Leu Gln Lys Thr Val Pro Trp Gly Val Ala Phe His
                405                 410                 415

His Ala Gly Leu Thr Phe Glu Glu Arg Asp Ile Ile Glu Gly Ala Phe
            420                 425                 430

Arg Gln Gly Leu Ile Arg Val Leu Ala Ala Thr Ser Thr Leu Ser Ser
        435                 440                 445

Gly Val Asn Leu Pro Ala Arg Arg Val Ile Ile Arg Thr Pro Ile Phe
        450                 455                 460

Gly Gly Arg Pro Leu Asp Ile Leu Thr Tyr Lys Gln Met Val Gly Arg
465                 470                 475                 480

Ala Gly Arg Lys Gly Val Asp Thr Val Gly Glu Ser Ile Leu Ile Cys
                485                 490                 495

Lys Asn Ser Glu Lys Ser Lys Gly Ile Ala Leu Leu Gln Gly Ser Leu
                500                 505                 510

Lys Pro Val Arg Ser Cys Leu Gln Arg Arg Glu Gly Glu Glu Val Thr
            515                 520                 525

Gly Ser Met Ile Arg Ala Ile Leu Glu Ile Ile Val Gly Gly Val Ala
        530                 535                 540

Ser Thr Ser Gln Asp Met His Thr Tyr Ala Ala Cys Thr Phe Leu Ala
545                 550                 555                 560

Ala Ser Met Lys Glu Gly Lys Gln Gly Ile Gln Arg Asn Gln Glu Ser
                565                 570                 575

Val Gln Leu Gly Ala Ile Glu Ala Cys Val Met Trp Leu Leu Glu Asn
            580                 585                 590

Glu Phe Ile Gln Ser Thr Glu Ala Ser Asp Gly Thr Glu Gly Lys Val
        595                 600                 605

Tyr His Pro Thr His Leu Gly Ser Ala Thr Leu Ser Ser Ser Leu Ser
610                 615                 620

Pro Ala Asp Thr Leu Asp Ile Phe Ala Asp Leu Gln Arg Ala Met Lys
```

```
                625                 630                 635                 640
        Gly Phe Val Leu Glu Asn Asp Leu His Ile Leu Tyr Leu Val Thr Pro
                        645                 650                 655

Met Phe Glu Asp Trp Thr Thr Ile Asp Trp Tyr Arg Phe Phe Cys Leu
                        660                 665                 670

Trp Glu Lys Leu Pro Thr Ser Met Lys Arg Val Ala Glu Leu Val Gly
                        675                 680                 685

Val Glu Glu Gly Phe Leu Ala Arg Cys Val Lys Gly Lys Val Val Ala
                        690                 695                 700

Arg Thr Glu Arg Gln His Arg Gln Met Ala Ile His Lys Arg Phe Phe
        705                 710                 715                 720

Thr Ser Leu Val Leu Leu Asp Leu Ile Ser Glu Val Pro Leu Arg Glu
                        725                 730                 735

Ile Asn Gln Lys Tyr Gly Cys Asn Arg Gly Gln Ile Gln Ser Leu Gln
                        740                 745                 750

Gln Ser Ala Ala Val Tyr Ala Gly Met Ile Thr Val Phe Ser Asn Arg
                        755                 760                 765

Leu Gly Trp His Asn Met Glu Leu Leu Leu Ser Gln Phe Gln Lys Arg
                        770                 775                 780

Leu Thr Phe Gly Ile Gln Arg Glu Leu Cys Asp Leu Val Arg Val Ser
        785                 790                 795                 800

Leu Leu Asn Ala Gln Arg Ala Arg Val Leu Tyr Ala Ser Gly Phe His
                        805                 810                 815

Thr Val Ala Asp Leu Ala Arg Ala Asn Ile Val Glu Val Glu Val Ile
                        820                 825                 830

Leu Lys Asn Ala Val Pro Phe Lys Ser Ala Arg Lys Ala Val Asp Glu
                        835                 840                 845

Glu Glu Glu Ala Val Glu Glu Arg Arg Asn Met Arg Thr Ile Trp Val
                        850                 855                 860

Thr Gly Arg Lys Gly Leu Thr Glu Arg Glu Ala Ala Ala Leu Ile Val
        865                 870                 875                 880

Glu Glu Ala Arg Met Ile Leu Gln Gln Asp Leu Val Glu Met Gly Val
                        885                 890                 895

Gln Trp Asn Pro Cys Ala Leu Leu His Ser Ser Thr Cys Ser Leu Thr
                        900                 905                 910

His Ser Glu Ser Glu Val Lys Glu His Thr Phe Ile Ser Gln Thr Lys
                        915                 920                 925

Ser Ser Tyr Lys Lys Leu Thr Ser Lys Asn Lys Ser Asn Thr Ile Phe
        930                 935                 940

Ser Asp Ser Tyr Ile Lys His Ser Pro Asn Ile Val Gln Asp Leu Asn
        945                 950                 955                 960

Lys Ser Arg Glu His Thr Ser Ser Phe Asn Cys Asn Phe Gln Asn Gly
                        965                 970                 975

Asn Gln Glu His Gln Thr Cys Ser Ile Phe Arg Ala Arg Lys Arg Ala
                        980                 985                 990

Ser Leu Asp Ile Asn Lys Glu Lys Pro Gly Ala Ser Gln Asn Glu Gly
                        995                 1000                1005

Lys Thr Ser Asp Lys Lys Val Val Gln Thr Phe Ser Gln Lys Thr
                        1010                1015                1020

Lys Lys Ala Pro Leu Asn Phe Asn Ser Glu Lys Met Ser Arg Ser
                        1025                1030                1035

Phe Arg Ser Trp Lys Arg Arg Lys His Leu Lys Arg Ser Arg Asp
                        1040                1045                1050
```

-continued

Ser Ser Pro Leu Lys Asp Ser Gly Ala Cys Arg Ile His Leu Gln
1055                1060                    1065

Gly Gln Thr Leu Ser Asn Pro Ser Leu Cys Glu Asp Pro Phe Thr
1070                1075                    1080

Leu Asp Glu Lys Lys Thr Glu Phe Arg Asn Ser Gly Pro Phe Ala
1085                1090                    1095

Lys Asn Val Ser Leu Ser Gly Lys Glu Lys Asp Asn Lys Thr Ser
1100                1105                    1110

Phe Pro Leu Gln Ile Lys Gln Asn Cys Ser Trp Asn Ile Thr Leu
1115                1120                    1125

Thr Asn Asp Asn Phe Val Glu His Ile Val Thr Gly Ser Gln Ser
1130                1135                    1140

Lys Asn Val Thr Cys Gln Ala Thr Ser Val Val Ser Glu Lys Gly
1145                1150                    1155

Arg Gly Val Ala Val Glu Ala Glu Lys Ile Asn Glu Val Leu Ile
1160                1165                    1170

Gln Asn Gly Ser Lys Asn Gln Asn Val Tyr Met Lys His His Asp
1175                1180                    1185

Ile His Pro Ile Asn Gln Tyr Leu Arg Lys Gln Ser His Glu Gln
1190                1195                    1200

Thr Ser Thr Ile Thr Lys Gln Lys Asn Ile Ile Glu Arg Gln Met
1205                1210                    1215

Pro Cys Glu Ala Val Ser Ser Tyr Ile Asn Arg Asp Ser Asn Val
1220                1225                    1230

Thr Ile Asn Cys Glu Arg Ile Lys Leu Asn Thr Glu Glu Asn Lys
1235                1240                    1245

Pro Ser His Phe Gln Ala Leu Gly Asp Asp Ile Ser Arg Thr Val
1250                1255                    1260

Ile Pro Ser Glu Val Leu Pro Ser Ala Gly Ala Phe Ser Lys Ser
1265                1270                    1275

Glu Gly Gln His Glu Asn Phe Leu Asn Ile Ser Arg Leu Gln Glu
1280                1285                    1290

Lys Thr Gly Thr Tyr Thr Thr Asn Lys Thr Lys Asn Asn His Val
1295                1300                    1305

Ser Asp Leu Gly Leu Val Leu Cys Asp Phe Glu Asp Ser Phe Tyr
1310                1315                    1320

Leu Asp Thr Gln Ser Glu Lys Ile Ile Gln Gln Met Ala Thr Glu
1325                1330                    1335

Asn Ala Lys Leu Gly Ala Lys Asp Thr Asn Leu Ala Ala Gly Ile
1340                1345                    1350

Met Gln Lys Ser Leu Val Gln Gln Asn Ser Met Asn Ser Phe Gln
1355                1360                    1365

Lys Glu Cys His Ile Pro Phe Pro Ala Glu Gln His Pro Leu Gly
1370                1375                    1380

Ala Thr Lys Ile Asp His Leu Asp Leu Lys Thr Val Gly Thr Met
1385                1390                    1395

Lys Gln Ser Ser Asp Ser His Gly Val Asp Ile Leu Thr Pro Glu
1400                1405                    1410

Ser Pro Ile Phe His Ser Pro Ile Leu Leu Glu Glu Asn Gly Leu
1415                1420                    1425

Phe Leu Lys Lys Asn Glu Val Ser Val Thr Asp Ser Gln Leu Asn
1430                1435                    1440

```
Ser Phe Leu Gln Gly Tyr Gln Thr Gln Glu Thr Val Lys Pro Val
    1445                1450                1455

Ile Leu Leu Ile Pro Gln Lys Arg Thr Pro Thr Gly Val Glu Gly
    1460                1465                1470

Glu Cys Leu Pro Val Pro Glu Thr Ser Leu Asn Met Ser Asp Ser
    1475                1480                1485

Leu Leu Phe Asp Ser Phe Ser Asp Asp Tyr Leu Val Lys Glu Gln
    1490                1495                1500

Leu Pro Asp Met Gln Met Lys Glu Pro Leu Pro Ser Glu Val Thr
    1505                1510                1515

Ser Asn His Phe Ser Asp Ser Leu Cys Leu Gln Glu Asp Leu Ile
    1520                1525                1530

Lys Lys Ser Asn Val Asn Glu Asn Gln Asp Thr His Gln Gln Leu
    1535                1540                1545

Thr Cys Ser Asn Asp Glu Ser Ile Ile Phe Ser Glu Met Asp Ser
    1550                1555                1560

Val Gln Met Val Glu Ala Leu Asp Asn Val Asp Ile Phe Pro Val
    1565                1570                1575

Gln Glu Lys Asn His Thr Val Val Ser Pro Arg Ala Leu Glu Leu
    1580                1585                1590

Ser Asp Pro Val Leu Asp Glu His His Gln Gly Asp Gln Asp Gly
    1595                1600                1605

Gly Asp Gln Asp Glu Arg Ala Glu Lys Ser Lys Leu Thr Gly Thr
    1610                1615                1620

Arg Gln Asn His Ser Phe Ile Trp Ser Gly Ala Ser Phe Asp Leu
    1625                1630                1635

Ser Pro Gly Leu Gln Arg Ile Leu Asp Lys Val Ser Ser Pro Leu
    1640                1645                1650

Glu Asn Glu Lys Leu Lys Ser Met Thr Ile Asn Phe Ser Ser Leu
    1655                1660                1665

Asn Arg Lys Asn Thr Glu Leu Asn Glu Glu Gln Glu Val Ile Ser
    1670                1675                1680

Asn Leu Glu Thr Lys Gln Val Gln Gly Ile Ser Phe Ser Ser Asn
    1685                1690                1695

Asn Glu Val Lys Ser Lys Ile Glu Met Leu Glu Asn Asn Ala Asn
    1700                1705                1710

His Asp Glu Thr Ser Ser Leu Leu Pro Arg Lys Glu Ser Asn Ile
    1715                1720                1725

Val Asp Asp Asn Gly Leu Ile Pro Pro Thr Pro Ile Pro Thr Ser
    1730                1735                1740

Ala Ser Lys Leu Thr Phe Pro Gly Ile Leu Glu Thr Pro Val Asn
    1745                1750                1755

Pro Trp Lys Thr Asn Asn Val Leu Gln Pro Gly Glu Ser Tyr Leu
    1760                1765                1770

Phe Gly Ser Pro Ser Asp Ile Lys Asn His Asp Leu Ser Pro Gly
    1775                1780                1785

Ser Arg Asn Gly Phe Lys Asp Asn Ser Pro Ile Ser Asp Thr Ser
    1790                1795                1800

Phe Ser Leu Gln Leu Ser Gln Asp Gly Leu Gln Leu Thr Pro Ala
    1805                1810                1815

Ser Ser Ser Ser Glu Ser Leu Ser Ile Ile Asp Val Ala Ser Asp
    1820                1825                1830

Gln Asn Leu Phe Gln Thr Phe Ile Lys Glu Trp Arg Cys Lys Lys
```

-continued

```
            1835                1840                1845
Arg Phe Ser Ile Ser Leu Ala Cys Glu Lys Ile Arg Ser Leu Thr
            1850                1855                1860
Ser Ser Lys Thr Ala Thr Ile Gly Ser Arg Phe Lys Gln Ala Ser
            1865                1870                1875
Ser Pro Gln Glu Ile Pro Ile Arg Asp Asp Gly Phe Pro Ile Lys
            1880                1885                1890
Gly Cys Asp Asp Thr Leu Val Val Gly Leu Ala Val Cys Trp Gly
            1895                1900                1905
Gly Arg Asp Ala Tyr Tyr Phe Ser Leu Gln Lys Glu Gln Lys His
            1910                1915                1920
Ser Glu Ile Ser Ala Ser Leu Val Pro Pro Ser Leu Asp Pro Ser
            1925                1930                1935
Leu Thr Leu Lys Asp Arg Met Trp Tyr Leu Gln Ser Cys Leu Arg
            1940                1945                1950
Lys Glu Ser Asp Lys Glu Cys Ser Val Val Ile Tyr Asp Phe Ile
            1955                1960                1965
Gln Ser Tyr Lys Ile Leu Leu Leu Ser Cys Gly Ile Ser Leu Glu
            1970                1975                1980
Gln Ser Tyr Glu Asp Pro Lys Val Ala Cys Trp Leu Leu Asp Pro
            1985                1990                1995
Asp Ser Gln Glu Pro Thr Leu His Ser Ile Val Thr Ser Phe Leu
            2000                2005                2010
Pro His Glu Leu Pro Leu Leu Glu Gly Met Glu Thr Ser Gln Gly
            2015                2020                2025
Ile Gln Ser Leu Gly Leu Asn Ala Gly Ser Glu His Ser Gly Arg
            2030                2035                2040
Tyr Arg Ala Ser Val Glu Ser Ile Leu Ile Phe Asn Ser Met Asn
            2045                2050                2055
Gln Leu Asn Ser Leu Leu Gln Lys Glu Asn Leu Gln Asp Val Phe
            2060                2065                2070
Arg Lys Val Glu Met Pro Ser Gln Tyr Cys Leu Ala Leu Leu Glu
            2075                2080                2085
Leu Asn Gly Ile Gly Phe Ser Thr Ala Glu Cys Glu Ser Gln Lys
            2090                2095                2100
His Ile Met Gln Ala Lys Leu Asp Ala Ile Glu Thr Gln Ala Tyr
            2105                2110                2115
Gln Leu Ala Gly His Ser Phe Ser Phe Thr Ser Ser Asp Asp Ile
            2120                2125                2130
Ala Glu Val Leu Phe Leu Glu Leu Lys Leu Pro Pro Asn Arg Glu
            2135                2140                2145
Met Lys Asn Gln Gly Ser Lys Lys Thr Leu Gly Ser Thr Arg Arg
            2150                2155                2160
Gly Ile Asp Asn Gly Arg Lys Leu Arg Leu Gly Arg Gln Phe Ser
            2165                2170                2175
Thr Ser Lys Asp Val Leu Asn Lys Leu Lys Ala Leu His Pro Leu
            2180                2185                2190
Pro Gly Leu Ile Leu Glu Trp Arg Arg Ile Thr Asn Ala Ile Thr
            2195                2200                2205
Lys Val Val Phe Pro Leu Gln Arg Glu Lys Cys Leu Asn Pro Phe
            2210                2215                2220
Leu Gly Met Glu Arg Ile Tyr Pro Val Ser Gln Ser His Thr Ala
            2225                2230                2235
```

```
Thr Gly Arg Ile Thr Phe Thr Glu Pro Asn Ile Gln Asn Val Pro
    2240                2245                2250

Arg Asp Phe Glu Ile Lys Met Pro Thr Leu Val Gly Glu Ser Pro
    2255                2260                2265

Pro Ser Gln Ala Val Gly Lys Gly Leu Leu Pro Met Gly Arg Gly
    2270                2275                2280

Lys Tyr Lys Lys Gly Phe Ser Val Asn Pro Arg Cys Gln Ala Gln
    2285                2290                2295

Met Glu Glu Arg Ala Ala Asp Arg Gly Met Pro Phe Ser Ile Ser
    2300                2305                2310

Met Arg His Ala Phe Val Pro Phe Pro Gly Gly Ser Ile Leu Ala
    2315                2320                2325

Ala Asp Tyr Ser Gln Leu Glu Leu Arg Ile Leu Ala His Leu Ser
    2330                2335                2340

His Asp Arg Arg Leu Ile Gln Val Leu Asn Thr Gly Ala Asp Val
    2345                2350                2355

Phe Arg Ser Ile Ala Ala Glu Trp Lys Met Ile Glu Pro Glu Ser
    2360                2365                2370

Val Gly Asp Asp Leu Arg Gln Gln Ala Lys Gln Ile Cys Tyr Gly
    2375                2380                2385

Ile Ile Tyr Gly Met Gly Ala Lys Ser Leu Gly Glu Gln Met Gly
    2390                2395                2400

Ile Lys Glu Asn Asp Ala Ala Cys Tyr Ile Asp Ser Phe Lys Ser
    2405                2410                2415

Arg Tyr Thr Gly Ile Asn Gln Phe Met Thr Glu Thr Val Lys Asn
    2420                2425                2430

Cys Lys Arg Asp Gly Phe Val Gln Thr Ile Leu Gly Arg Arg Arg
    2435                2440                2445

Tyr Leu Pro Gly Ile Lys Asp Asn Asn Pro Tyr Arg Lys Ala His
    2450                2455                2460

Ala Glu Arg Gln Ala Ile Asn Thr Ile Val Gln Gly Ser Ala Ala
    2465                2470                2475

Asp Ile Val Lys Ile Ala Thr Val Asn Ile Gln Lys Gln Leu Glu
    2480                2485                2490

Thr Phe His Ser Thr Phe Lys Ser His Gly His Arg Glu Gly Met
    2495                2500                2505

Leu Gln Ser Asp Gln Thr Gly Leu Ser Arg Lys Arg Lys Leu Gln
    2510                2515                2520

Gly Met Phe Cys Pro Ile Arg Gly Gly Phe Phe Ile Leu Gln Leu
    2525                2530                2535

His Asp Glu Leu Leu Tyr Glu Val Ala Glu Glu Asp Val Val Gln
    2540                2545                2550

Val Ala Gln Ile Val Lys Asn Glu Met Glu Ser Ala Val Lys Leu
    2555                2560                2565

Ser Val Lys Leu Lys Val Lys Val Lys Ile Gly Ala Ser Trp Gly
    2570                2575                2580

Glu Leu Lys Asp Phe Asp Val
    2585                2590

<210> SEQ ID NO 2
<211> LENGTH: 2544
<212> TYPE: PRT
<213> ORGANISM: Mus musculus
```

```
<400> SEQUENCE: 2

Met Ser Leu Pro Arg Ser Arg Lys Arg Arg Ser Ser Gly
1               5                   10                  15

Ser Asp Thr Phe Ser Gly Asp Gly Asp Ser Phe Val Ser Pro Gln Leu
                20                  25                  30

Arg Cys Gly Pro Val Leu Ser Pro Pro Gly Leu Gly Arg Gly Arg
            35                  40                  45

Arg Leu Thr Gly Thr Gly Thr Asn Lys Arg Arg Val Ser Asp Asp Gln
    50                  55                  60

Ile Asp Gln Leu Leu Leu Ala Asn Trp Gly Leu Pro Lys Ala Val Leu
65                  70                  75                  80

Glu Lys Tyr His Ser Phe Gly Val Arg Lys Met Phe Glu Trp Gln Ala
                85                  90                  95

Glu Cys Leu Leu Leu Gly His Val Leu Glu Gly Lys Asn Leu Val Tyr
            100                 105                 110

Ser Ala Pro Thr Ser Ala Gly Lys Thr Leu Val Ala Glu Leu Leu Ile
            115                 120                 125

Leu Lys Arg Val Leu Glu Thr Arg Lys Lys Ala Leu Phe Ile Leu Pro
130                 135                 140

Phe Val Ser Val Ala Lys Glu Lys Lys Cys Tyr Leu Gln Ser Leu Phe
145                 150                 155                 160

Gln Glu Val Gly Leu Lys Val Asp Gly Tyr Met Gly Ser Thr Ser Pro
                165                 170                 175

Thr Gly Gln Phe Ser Ser Leu Asp Ile Ala Val Cys Thr Ile Glu Arg
            180                 185                 190

Ala Asn Gly Leu Val Asn Arg Leu Ile Glu Glu Asn Lys Met Asp Leu
    195                 200                 205

Leu Gly Met Val Val Asp Glu Leu His Met Leu Gly Asp Ser His
210                 215                 220

Arg Gly Tyr Leu Leu Glu Leu Leu Thr Lys Ile Cys Tyr Val Thr
225                 230                 235                 240

Arg Lys Ser Ala Ser His Gln Ala Glu Ser Ala Ser Thr Leu Ser Asn
            245                 250                 255

Ala Val Gln Ile Val Gly Met Ser Ala Thr Leu Pro Asn Leu Gln Leu
            260                 265                 270

Val Ala Ser Trp Leu Asn Ala Glu Leu Tyr His Thr Asp Phe Arg Pro
        275                 280                 285

Val Pro Leu Leu Glu Ser Ile Lys Ile Gly Asn Ser Ile Tyr Asp Ser
    290                 295                 300

Ser Met Lys Leu Val Arg Glu Phe Gln Pro Leu Leu Gln Val Lys Gly
305                 310                 315                 320

Asp Glu Asp His Ile Val Ser Leu Cys Tyr Glu Thr Ile Gln Asp Asn
                325                 330                 335

His Ser Val Leu Ile Phe Cys Pro Ser Lys Lys Trp Cys Glu Lys Val
            340                 345                 350

Ala Asp Ile Ile Ala Arg Glu Phe Tyr Asn Leu His His Gln Pro Glu
    355                 360                 365

Gly Leu Val Lys Ser Ser Glu Phe Pro Pro Val Ile Leu Asp Gln Lys
370                 375                 380

Ser Leu Leu Glu Val Met Asp Gln Leu Lys Arg Ser Pro Ser Gly Leu
385                 390                 395                 400

Asp Ser Val Leu Lys Asn Thr Val Pro Trp Gly Val Ala Phe His His
                405                 410                 415
```

```
Ala Gly Leu Thr Phe Glu Arg Asp Ile Ile Glu Gly Ala Phe Arg
            420                 425                 430

Gln Gly Phe Ile Arg Val Leu Ala Ala Thr Ser Thr Leu Ser Ser Gly
        435                 440                 445

Val Asn Leu Pro Ala Arg Arg Val Ile Ile Arg Thr Pro Ile Phe Ser
450                 455                 460

Gly Gln Pro Leu Asp Ile Leu Thr Tyr Lys Gln Met Val Gly Arg Ala
465                 470                 475                 480

Gly Arg Lys Gly Val Asp Thr Met Gly Glu Ser Ile Leu Val Cys Lys
                485                 490                 495

Asn Ser Glu Lys Ser Lys Gly Ile Ala Leu Leu Gln Gly Ser Leu Glu
                500                 505                 510

Pro Val His Ser Cys Leu Gln Arg Gln Gly Glu Val Thr Ala Ser Met
                515                 520                 525

Ile Arg Ala Ile Leu Glu Ile Ile Val Gly Gly Val Ala Ser Thr Ser
530                 535                 540

Gln Asp Met Gln Thr Tyr Ala Ala Cys Thr Phe Leu Ala Ala Ala Ile
545                 550                 555                 560

Gln Glu Gly Lys Gln Gly Met Gln Arg Asn Gln Asp Asp Ala Gln Leu
                565                 570                 575

Gly Ala Ile Asp Ala Cys Val Thr Trp Leu Leu Glu Asn Glu Phe Ile
                580                 585                 590

Gln Val Ala Glu Pro Gly Asp Gly Thr Gly Gly Lys Val Tyr His Pro
                595                 600                 605

Thr His Leu Gly Ser Ala Thr Leu Ser Ser Ser Leu Ser Pro Thr Asp
        610                 615                 620

Thr Leu Asp Ile Phe Ala Asp Leu Gln Arg Ala Met Lys Gly Phe Val
625                 630                 635                 640

Leu Glu Asn Asp Leu His Ile Val Tyr Leu Val Thr Pro Val Phe Glu
                645                 650                 655

Asp Trp Ile Ser Ile Asp Trp Tyr Arg Phe Phe Cys Leu Trp Glu Lys
                660                 665                 670

Leu Pro Thr Ser Met Lys Arg Val Ala Glu Leu Val Gly Val Glu Glu
                675                 680                 685

Gly Phe Leu Ala Arg Cys Val Lys Gly Lys Val Val Ala Arg Thr Glu
        690                 695                 700

Arg Gln His Arg Gln Met Ala Ile His Lys Arg Phe Phe Thr Ser Leu
705                 710                 715                 720

Val Leu Leu Asp Leu Ile Ser Glu Ile Pro Leu Lys Asp Ile Asn Gln
                725                 730                 735

Lys Tyr Gly Cys Asn Arg Gly Gln Ile Gln Ser Leu Gln Gln Ser Ala
                740                 745                 750

Ala Val Tyr Ala Gly Met Ile Thr Val Phe Ser Asn Arg Leu Gly Trp
                755                 760                 765

His Asn Met Glu Leu Leu Leu Ser Gln Phe Gln Lys Arg Leu Thr Phe
            770                 775                 780

Gly Ile Gln Arg Glu Leu Cys Asp Leu Ile Arg Val Ser Leu Leu Asn
785                 790                 795                 800

Ala Gln Arg Ala Arg Phe Leu Tyr Ala Ser Gly Phe Leu Thr Val Ala
                805                 810                 815

Asp Leu Ala Arg Ala Asp Ser Ala Glu Val Glu Val Ala Leu Lys Asn
            820                 825                 830
```

```
Ser Leu Pro Phe Lys Ser Ala Arg Lys Ala Val Asp Glu Glu Glu
        835                 840                 845

Ala Ala Glu Glu Arg Arg Ser Met Arg Thr Ile Trp Val Thr Gly Lys
850                 855                 860

Gly Leu Ser Ala Arg Glu Ala Ala Leu Ile Val Glu Glu Ala Lys
865                 870                 875                 880

Met Ile Leu Gln Gln Asp Leu Ile Glu Met Gly Val Arg Trp Asp Pro
                885                 890                 895

Lys Ser Pro Leu Ser Ser Ser Thr His Ser Arg Thr Ser Thr Ser Glu
                900                 905                 910

Val Lys Glu His Thr Phe Lys Ser Gln Thr Lys Ser Ser His Lys Arg
                915                 920                 925

Leu Ala Ser Met Gly Arg Asn Ser Ile Arg Ala Ser Gly Ser Asn Asp
                930                 935                 940

Lys Pro Ser Pro Asp Ala Glu Arg Gly Ile Asp Asp Cys Ser Glu His
945                 950                 955                 960

Ala Asp Ser Leu Cys Lys Phe Gln Gly Asn Phe Glu Pro Gln Thr Pro
                965                 970                 975

Ser Ile Cys Thr Ala Arg Lys Arg Thr Ser Leu Gly Ile Asn Lys Glu
                980                 985                 990

Met Leu Arg Lys Ser Leu Lys Glu  Gly Lys Pro Ser Thr  Lys Glu Val
        995                 1000                1005

Leu Gln Thr Phe Ser Ser Glu  Lys Thr Arg Lys Thr  Ala Leu Ser
    1010                1015                1020

Phe Ser Ser Glu Gln Val Asn  Asn Thr Leu Pro Ser  Gly Arg Asp
    1025                1030                1035

Arg Lys Tyr Gln Lys Lys Ser  Trp Gly Ser Ser Pro  Val Arg Asp
    1040                1045                1050

Ser Gly Met His Arg Gly Asp  Leu Gln Gly Gln Thr  Met Cys Thr
    1055                1060                1065

Ser Ala Leu Cys Glu Asp Ser  Gln Lys Ser Leu Glu  Glu Gln Asn
    1070                1075                1080

Ala Glu Phe Arg Ser Pro Gly  Leu Phe Ala Lys His  Leu Pro Ser
    1085                1090                1095

Cys Ala Lys Glu Lys Cys Lys  Lys Pro Ser Leu Pro  Leu Gln Arg
    1100                1105                1110

Gln Gln Ala Cys Ser Arg Arg  Ser Thr Glu Ser Cys  Ala Ala Val
    1115                1120                1125

Gly His Pro Ala Ala Gly Ser  Ser Pro Ala Ala Ala  Arg Asp Arg
    1130                1135                1140

Arg Gly Leu Ala Ala Arg Glu  Thr Glu Lys Gly Asn  Glu Ala Leu
    1145                1150                1155

Thr Glu Asn Gly Gly Glu Ser  Gln Leu Gln Asp Thr  Tyr Pro Val
    1160                1165                1170

Ser Gln Tyr Leu Glu Tyr His  Ser Glu Lys His Thr  Asn Thr Cys
    1175                1180                1185

Thr Arg Gln Lys Thr Leu Thr  Glu Gly Gln Ala Gly  Ser Ser Tyr
    1190                1195                1200

Val Ala Arg Asp Ser Asn Asp  Ala Ala Pro Ile Lys  Cys Glu Arg
    1205                1210                1215

Met Lys Leu Asn Ser Lys Asp  Arg Asp Ser Asn Pro  Cys Arg Gln
    1220                1225                1230

Ala Leu Gly Ser Tyr Thr Gly  Arg Thr Glu Ala Leu  Gln Ser Thr
```

-continued

```
            1235                1240                1245

Ala Lys Leu Gly Gln Ala Gly Gly Gln Cys Glu Asn Leu Leu Asn
        1250                1255                1260

Ser Ser Gly Val Gln Gly Lys Thr Gly Ala His Ala Thr Asn Arg
        1265                1270                1275

Thr Glu His Ser His Ala Ser Asn Pro Ala Phe Cys Asp Phe Gly
        1280                1285                1290

Asp Ser Leu Asp Leu Asp Thr Gln Ser Glu Glu Ile Ile Glu Gln
        1295                1300                1305

Met Ala Thr Glu Asn Thr Met Gln Gly Ala Lys Ala Val Val Ile
        1310                1315                1320

Met Glu Glu Gly Ser Ala Met Gln Asn Lys Cys His Ser Thr Pro
        1325                1330                1335

Gly Asp Gln His Val Pro Gly Ala Ala Asn Thr Asp His Val Asp
        1340                1345                1350

Ser Lys Lys Val Glu Ser Val Lys Ala Asn Thr Glu Lys Asn Ile
        1355                1360                1365

Asn Arg Gly Ala Pro Val Ser Leu Ile Phe His Thr Gln Gly Glu
        1370                1375                1380

Asn Gly Ala Cys Phe Lys Gly Asn Glu His Ser Val Thr Asp Ser
        1385                1390                1395

Gln Leu Asn Ser Phe Leu Gln Gly Phe Glu Thr Gln Glu Ile Val
        1400                1405                1410

Lys Pro Ile Ile Pro Leu Ala Pro Gln Met Arg Thr Pro Thr Gly
        1415                1420                1425

Val Glu Glu Glu Ser Leu Pro Glu Thr Ser Leu Asn Met Ser Asp
        1430                1435                1440

Ser Ile Leu Phe Asp Ser Phe Gly Glu Asp Gly Phe Gly Gln Gly
        1445                1450                1455

Gln Ser Pro Asp Ile Lys Ala Asn Gln Pro Leu Leu Ser Glu Met
        1460                1465                1470

Thr Pro Asn His Phe Ser Asn Pro Pro His Pro Gln Glu Asp Pro
        1475                1480                1485

Val Met Thr Pro Thr Val Ser Glu Pro Gln Gly Thr Gln Gln Gln
        1490                1495                1500

Gly Val Cys Leu Ser Gly Glu Ser Ile Ile Phe Ser Asp Ile Asp
        1505                1510                1515

Ser Ala Gln Val Ile Glu Ala Leu Asp Asn Met Ala Ala Phe His
        1520                1525                1530

Val Gln Glu Asn Cys Asn Ser Val Ala Leu Lys Thr Leu Glu Pro
        1535                1540                1545

Ser Asp Ser Ala Val Leu Gly Asn Glu Cys Pro Gln Gly Lys Leu
        1550                1555                1560

Val Arg Gly Asp Gln Asn Glu Gly Ser Pro Lys Pro Lys Leu Thr
        1565                1570                1575

Glu Thr Asn Gln Asp Asn Ser Phe Thr Trp Ser Gly Ala Ser Phe
        1580                1585                1590

Asn Leu Ser Pro Glu Leu Gln Arg Ile Leu Asp Lys Val Ser Ser
        1595                1600                1605

Pro Arg Glu Asn Glu Lys Pro Lys Met Ile His Val Asn Leu Ser
        1610                1615                1620

Ser Phe Glu Gly Asn Ser Lys Glu Ser His Glu Arg Glu Glu Ile
        1625                1630                1635
```

```
Asn Ser Asp Leu Gly Thr Val Gln Arg Thr Ser Val Phe Pro Ser
    1640            1645                1650

Asn Glu Val Lys Asn Arg Thr Glu Gly Leu Glu Ser Lys Ala Arg
    1655            1660                1665

His Gly Gly Ala Ser Ser Pro Leu Pro Arg Lys Glu Ser Ala Ala
    1670            1675                1680

Ala Asp Asp Asn Gly Leu Ile Pro Pro Thr Pro Val Pro Ala Ser
    1685            1690                1695

Ala Ser Lys Val Ala Phe Pro Glu Ile Leu Gly Thr Ser Val Lys
    1700            1705                1710

Arg Gln Lys Ala Ser Ser Ala Leu Gln Pro Gly Glu Ser Cys Leu
    1715            1720                1725

Phe Gly Ser Pro Ser Asp Asn Gln Asn Gln Asp Leu Ser Gln Glu
    1730            1735                1740

Leu Arg Asp Ser Leu Lys Asp Tyr Asp Gly Ser Val Ala Asp Thr
    1745            1750                1755

Ser Phe Phe Leu Gln Ser Gln Asp Gly Leu Leu Leu Thr Gln Ala
    1760            1765                1770

Ser Cys Ser Ser Glu Ser Leu Ala Ile Ile Asp Val Ala Ser Asp
    1775            1780                1785

Gln Ile Leu Phe Gln Thr Phe Val Lys Glu Trp Gln Cys Gln Lys
    1790            1795                1800

Arg Phe Ser Ile Ser Leu Ala Cys Glu Lys Met Thr Ser Ser Met
    1805            1810                1815

Ser Ser Lys Thr Ala Thr Ile Gly Gly Lys Leu Lys Gln Val Ser
    1820            1825                1830

Leu Pro Gln Glu Ala Thr Val Glu Asp Ala Gly Phe Pro Val Arg
    1835            1840                1845

Gly Cys Asp Gly Ala Val Val Gly Leu Ala Val Cys Trp Gly
    1850            1855                1860

Ala Lys Asp Ala Tyr Tyr Leu Ser Leu Gln Lys Glu Gln Lys Gln
    1865            1870                1875

Ser Glu Ile Ser Pro Ser Leu Ala Pro Pro Leu Asp Ala Thr
    1880            1885                1890

Leu Thr Val Lys Glu Arg Met Glu Cys Leu Gln Ser Cys Leu Gln
    1895            1900                1905

Lys Lys Ser Asp Arg Glu Arg Ser Val Val Thr Tyr Asp Phe Ile
    1910            1915                1920

Gln Thr Tyr Lys Val Leu Leu Leu Ser Cys Gly Ile Ser Leu Glu
    1925            1930                1935

Pro Ser Tyr Glu Asp Pro Lys Val Ala Cys Trp Leu Leu Asp Pro
    1940            1945                1950

Asp Ser Lys Glu Pro Thr Leu His Ser Ile Val Thr Ser Phe Leu
    1955            1960                1965

Pro His Glu Leu Ala Leu Leu Glu Gly Met Glu Thr Gly Pro Gly
    1970            1975                1980

Ile Gln Ser Leu Gly Leu Asn Val Asn Thr Glu His Ser Gly Arg
    1985            1990                1995

Tyr Arg Ala Ser Val Glu Ser Val Leu Ile Phe Asn Ser Met Asn
    2000            2005                2010

Gln Leu Asn Ser Leu Leu Gln Lys Glu Asn Leu His Asp Ile Phe
    2015            2020                2025
```

```
Cys Lys Val Glu Met Pro Ser Gln Tyr Cys Leu Ala Leu Leu Glu
2030                2035                2040

Leu Asn Gly Ile Gly Phe Ser Thr Ala Glu Cys Glu Ser Gln Lys
2045                2050                2055

His Val Met Gln Ala Lys Leu Asp Ala Ile Glu Thr Gln Ala Tyr
2060                2065                2070

Gln Leu Ala Gly His Ser Phe Ser Phe Thr Ser Ala Asp Asp Ile
2075                2080                2085

Ala Gln Val Leu Phe Leu Glu Leu Lys Leu Pro Pro Asn Gly Glu
2090                2095                2100

Met Lys Thr Gln Gly Ser Lys Lys Thr Leu Gly Ser Thr Arg Arg
2105                2110                2115

Gly Asn Glu Ser Gly Arg Arg Met Arg Leu Gly Arg Gln Phe Ser
2120                2125                2130

Thr Ser Lys Asp Ile Leu Asn Lys Leu Lys Gly Leu His Pro Leu
2135                2140                2145

Pro Gly Leu Ile Leu Glu Trp Arg Arg Ile Ser Asn Ala Ile Thr
2150                2155                2160

Lys Val Val Phe Pro Leu Gln Arg Glu Lys His Leu Asn Pro Leu
2165                2170                2175

Leu Arg Met Glu Arg Ile Tyr Pro Val Ser Gln Ser His Thr Ala
2180                2185                2190

Thr Gly Arg Ile Thr Phe Thr Glu Pro Asn Ile Gln Asn Val Pro
2195                2200                2205

Arg Asp Phe Glu Ile Lys Met Pro Thr Leu Val Arg Glu Ser Pro
2210                2215                2220

Pro Ser Gln Ala Pro Lys Gly Arg Phe Pro Met Ala Ile Gly Gln
2225                2230                2235

Asp Lys Lys Val Tyr Gly Leu His Pro Gly His Arg Thr Gln Met
2240                2245                2250

Glu Glu Lys Ala Ser Asp Arg Gly Val Pro Phe Ser Val Ser Met
2255                2260                2265

Arg His Ala Phe Val Pro Phe Pro Gly Gly Leu Ile Leu Ala Ala
2270                2275                2280

Asp Tyr Ser Gln Leu Glu Leu Arg Ile Leu Ala His Leu Ser Arg
2285                2290                2295

Asp Cys Arg Leu Ile Gln Val Leu Asn Thr Gly Ala Asp Val Phe
2300                2305                2310

Arg Ser Ile Ala Ala Glu Trp Lys Met Ile Glu Pro Asp Ala Val
2315                2320                2325

Gly Asp Asp Leu Arg Gln His Ala Lys Gln Ile Cys Tyr Gly Ile
2330                2335                2340

Ile Tyr Gly Met Gly Ala Lys Ser Leu Gly Glu Gln Met Gly Ile
2345                2350                2355

Lys Glu Asn Asp Ala Ala Ser Tyr Ile Asp Ser Phe Lys Ser Arg
2360                2365                2370

Tyr Lys Gly Ile Asn His Phe Met Arg Asp Thr Val Lys Asn Cys
2375                2380                2385

Arg Lys Asn Gly Phe Val Glu Thr Ile Leu Gly Arg Arg Arg Tyr
2390                2395                2400

Leu Pro Gly Ile Lys Asp Asp Asn Pro Tyr His Lys Ala His Ala
2405                2410                2415

Glu Arg Gln Ala Ile Asn Thr Thr Val Gln Gly Ser Ala Ala Asp
```

```
            2420                2425                2430
Ile Val Lys Ile Ala Thr Val Asn Ile Gln Lys Gln Leu Glu Thr
        2435                2440                2445

Phe Arg Ser Thr Phe Lys Ser His Gly His Arg Glu Ser Met Leu
    2450                2455                2460

Gln Asn Asp Arg Thr Gly Leu Leu Pro Lys Arg Lys Leu Lys Gly
    2465                2470                2475

Met Phe Cys Pro Met Arg Gly Gly Phe Phe Ile Leu Gln Leu His
    2480                2485                2490

Asp Glu Leu Leu Tyr Glu Val Ala Glu Glu Asp Val Val Gln Val
    2495                2500                2505

Ala Gln Ile Val Lys Asn Glu Met Glu Cys Ala Ile Lys Leu Ser
    2510                2515                2520

Val Lys Leu Lys Val Lys Val Lys Ile Gly Ala Ser Trp Gly Glu
    2525                2530                2535

Leu Lys Asp Phe Asp Val
    2540

<210> SEQ ID NO 3
<211> LENGTH: 2579
<212> TYPE: PRT
<213> ORGANISM: Danio rerio

<400> SEQUENCE: 3

Met Met Thr Ser Thr Thr Arg Lys Ile Tyr Leu Gly Gln His Arg Ile
1               5                   10                  15

Val Lys Thr Arg Gly Leu Ser Leu Ala Asp Glu Lys Pro Gly Gln Arg
            20                  25                  30

Gln Leu Ser Asn Leu Cys Gln Glu Asp Val Ser Glu Asn Arg Ser Cys
        35                  40                  45

Ile Ala Pro Lys Gln Ile Gln Ser Lys Gln Trp Met Pro Gly Asp Ser
    50                  55                  60

Ser Leu Ala Met Asp Glu Glu Ile Leu Gln Ala Ile Asp Glu Leu Gly
65                  70                  75                  80

Pro Glu Val Leu Lys Phe Lys Lys Ile Glu Lys Ile Gln Thr Glu
                85                  90                  95

Pro Ala Pro Leu Lys Lys Asn Cys Asp Phe Pro Lys Ile Pro Glu Ile
            100                 105                 110

Gln Lys Glu Gln Asn Thr Glu Asn Ile Ser Pro Ser Ser Pro Ser Glu
        115                 120                 125

His Lys Arg Thr Arg Thr Gln Ala Lys Lys Glu Gly Asp Trp Lys Asp
    130                 135                 140

Leu Ala Gln Lys Leu Leu Phe Ser Glu Thr Lys Lys Ile Glu Val Gly
145                 150                 155                 160

Gly Arg Thr His Asp Leu Lys Gln Asn Arg Asp Tyr Ser Ser Pro Gln
                165                 170                 175

Lys Ile Leu Asn Ser Met Lys Lys Thr Ser Lys Val Ala Lys Ser Lys
            180                 185                 190

Gln Lys Leu Asn Phe Arg Glu Val Thr Ser Pro Asn Asp Ser Lys Asp
        195                 200                 205

Tyr Ile Leu Phe Ser Pro Thr His Met Ala Ala Ala Lys Glu Arg Ser
    210                 215                 220

Val Leu Gln Gln Gln Lys Arg Ser Leu Lys Asn Gln Ser Val Ser Val
225                 230                 235                 240
```

```
Leu Thr Pro Pro Pro Gly Leu Asp Leu Thr Val Leu Gly Asp Ala Thr
                245                 250                 255

Leu Ser Asp Ala Ala Gln Ser Ile His Met Gly Arg Pro Ala Asp Gln
            260                 265                 270

Leu Asp Lys Leu Leu Leu Ser Ser Trp Gly Leu Pro Lys Pro Val Leu
        275                 280                 285

Glu Lys Tyr Gln Ser Leu Gly Val His Arg Met Phe Glu Trp Gln Ala
    290                 295                 300

Glu Cys Leu Thr Leu Gly Lys Val Leu Glu Gly Gln Asn Leu Val Tyr
305                 310                 315                 320

Ser Ala Pro Thr Ser Ala Gly Lys Thr Leu Val Ser Glu Leu Leu Ile
                325                 330                 335

Leu Lys Arg Val Leu Glu Thr Arg Gln Lys Ala Met Phe Ile Leu Pro
            340                 345                 350

Phe Val Ser Val Ala Arg Glu Lys Met Phe Tyr Leu Gln Asn Val Phe
        355                 360                 365

Gln Glu Ala Gly Ile Arg Val Glu Gly Tyr Met Gly Ser Thr Ser Ala
    370                 375                 380

Ala Gly Gly Phe Ser Ala Leu Asp Val Ala Val Cys Thr Ile Glu Lys
385                 390                 395                 400

Ala Asn Gly Leu Val Asn Arg Leu Ile Glu Glu Asp Lys Leu Asp Leu
                405                 410                 415

Leu Gly Thr Val Val Asp Glu Leu His Met Val Gly Asp Ser Gly
            420                 425                 430

Arg Gly Tyr Leu Leu Glu Leu Leu Thr Lys Ile Arg Tyr Ile Ala
        435                 440                 445

Gln Lys Thr Ala Thr Arg Asn Ser Gly Gln Ser Thr Ser Thr Gly Val
    450                 455                 460

Gln Ile Ile Gly Met Ser Ala Thr Leu Pro Asn Leu Asp Leu Leu Ala
465                 470                 475                 480

Arg Trp Leu Ser Ala Glu Leu Tyr Ser Thr Asn Tyr Arg Pro Val Pro
                485                 490                 495

Leu Met Glu Trp Val Lys Ile Gly Thr Asn Ile Tyr Asp Gly Ser Leu
            500                 505                 510

Asn Leu Val Arg Gln Phe Thr Pro Ala Leu Pro Ile Lys Gly Asp Asp
        515                 520                 525

Asp His Ile Val Ser Leu Cys Phe Glu Thr Val Gln Asp Gly His Ser
    530                 535                 540

Ala Leu Leu Phe Cys Pro Ser Lys Asn Trp Cys Glu Lys Leu Ala Asp
545                 550                 555                 560

Ser Ile Gly Arg Glu Phe Tyr Asn Leu His His Lys Glu Met Gln Ser
                565                 570                 575

Gly Ser Gly Gly Gln Ser Ile Phe Leu Asn Gln Glu Gly Leu Leu Asp
            580                 585                 590

Val Leu Ala Gln Leu Lys Arg Thr Pro Ala Gly Leu Asp His Val Leu
        595                 600                 605

Gln Arg Thr Val Pro Trp Gly Val Ala Phe His Ala Gly Leu Thr
    610                 615                 620

Phe Asp Glu Arg Asp Ile Leu Glu Gly Ala Phe Arg Gln Gly Tyr Ile
625                 630                 635                 640

Arg Val Leu Ala Ala Thr Ser Thr Leu Ser Ser Gly Val Asn Leu Pro
                645                 650                 655

Ala Arg Arg Val Ile Ile Arg Thr Pro Val Phe Asn Gly His Leu Leu
```

-continued

```
            660                 665                 670
Asp Ile Leu Thr Tyr Lys Gln Met Val Gly Arg Ala Gly Arg Lys Gly
                675                 680                 685
Val Asp Thr Ile Gly Glu Ser Val Leu Val Cys Lys Glu Ala Glu Arg
    690                 695                 700
Ala Lys Gly Met Ser Leu Ile Gln Gly Ser Leu Lys Pro Ile Ser Ser
705                 710                 715                 720
Cys Leu Val Lys Arg Glu Gly Glu Val Thr Thr Ser Met Leu Arg
                725                 730                 735
Ala Ile Leu Glu Ile Ile Val Gly Val Ala Ser Ser Pro Gln Asp
                740                 745                 750
Val Arg Met Tyr Ala Ala Cys Thr Leu Leu Ala Ala Ser Ile Ala Ala
                755                 760                 765
Glu Glu Ala His Gln Asp Gly Ser Glu Ser Ala Arg Asn Lys Gly
                770                 775                 780
Ala Ile Glu Ala Cys Ile Glu Trp Leu Met Asp Asn Glu Phe Ile His
785                 790                 795                 800
Ile Gln Lys Glu Gly Asp Val Glu Arg Tyr Cys Pro Thr His Leu Gly
                805                 810                 815
Ser Ala Thr Leu Ser Ser Ser Leu Ser Pro Pro Glu Ala Leu Gly Ile
                820                 825                 830
Phe Ala Asp Leu Gln Arg Ala Met Lys Gly Phe Val Leu Glu Asn Asp
                835                 840                 845
Leu His Ile Leu Tyr Gln Ile Thr Pro Val Tyr Val Asp Trp Thr Thr
                850                 855                 860
Ile Asp Trp Tyr Gln Phe Phe Cys Leu Trp Glu Gln Leu Pro Ser Ala
865                 870                 875                 880
Met Lys Arg Val Ala Glu Met Val Gly Ile Glu Gly Phe Leu Ala
                885                 890                 895
Arg Ser Val Gly Gly Lys Leu Ile Ala Lys Thr Glu Lys Gln Arg Arg
                900                 905                 910
Gln Met Ala Ile His Lys Arg Phe Phe Thr Thr Leu Val Leu Leu Asp
                915                 920                 925
Leu Val Ser Glu Glu Pro Leu Gly Ala Val Ala Lys Lys Tyr Gly Cys
                930                 935                 940
Ser Arg Gly Gln Leu Gln Ser Leu Gln Gln Ser Ala Ser Thr Tyr Ala
945                 950                 955                 960
Gly Met Val Thr Val Phe Cys Asn Arg Leu Gly Trp His Asn Leu Glu
                965                 970                 975
Leu Leu Leu Ser Gln Phe Gln Ser Arg Leu Ser Phe Gly Val Gln Arg
                980                 985                 990
Glu Leu Cys Asp Leu Val Arg Ile Ser Leu Leu Thr Ala Gln Arg Ala
                995                 1000                 1005
Arg Thr Leu Tyr Ser Ser Gly Phe Val Thr Val Ala Glu Leu Ala
                1010                 1015                 1020
Arg Ala Asp Val Ser Glu Val Glu Lys Ala Leu Arg Lys Ala Ile
                1025                 1030                 1035
Pro Phe Lys Ser Ser Arg Gln Ala Val Asp Glu Ser Glu Val Glu
                1040                 1045                 1050
Ala Gln Glu Arg Lys Ser Met Arg Cys Ile Trp Val Ser Gly Lys
                1055                 1060                 1065
Lys Ala Leu Thr Glu Arg Glu Ala Ala Gln Gln Ile Val Ala Glu
                1070                 1075                 1080
```

```
Ala Gln Leu Leu Leu Gln Lys Asp Leu Ala Leu Leu Gly Val Glu
    1085                1090                1095

Trp Ser Pro Ala Cys Leu Pro Ala Lys Thr Gln Pro Asp Asn Ser
    1100                1105                1110

Ser Thr Val Lys Ser Asn Thr Glu Pro Arg Ser Met Ser Gly Gly
    1115                1120                1125

Thr Glu His Glu Gly Asp Gln Asp Leu Met Ser Asn Val Thr Glu
    1130                1135                1140

Glu Lys Leu Leu Leu Glu Asn Asn Ser Asp Asn Asn Ser His Pro
    1145                1150                1155

Pro Leu Arg Pro Leu Glu Ser Thr Thr Asn Ser Glu Lys Thr Met
    1160                1165                1170

Asp Val Asp Ser Gly Val Ser Ser Ala Glu Cys Gln Pro Asp Lys
    1175                1180                1185

Lys Cys Glu Leu Gln Ser Ser Val Leu His Lys Val Leu Lys Ser
    1190                1195                1200

Ile Asn Thr Lys Asp Lys Gly Cys Asp Asn Asn His Thr Val Glu
    1205                1210                1215

Ser Ser Ser Glu Thr Leu Gln Arg Arg Asn Ser Cys Leu Asn Thr
    1220                1225                1230

Cys Ile Ser Gly Asn Asp Gln His Cys Val Ser Pro Val Ser Lys
    1235                1240                1245

Arg Arg Arg Met Asp Ala Ala Gly Asp Glu Glu Gly Pro Thr Val
    1250                1255                1260

Thr Gly Val Lys Met Arg Ile Ala Asn Gly Leu Ala Thr Asp Arg
    1265                1270                1275

Lys Glu Met Pro Lys Pro Glu Glu Leu Cys Arg Ile Asp Gln Val
    1280                1285                1290

Lys Met Lys Leu Asn Lys Asp Thr Gly Leu Lys Lys Asp Ser Arg
    1295                1300                1305

Ser Cys Thr Pro Leu Pro Asn Gly Glu Val Thr Asn Val Cys Val
    1310                1315                1320

Phe Ser Ser Gly Lys Gly Lys Lys Arg Thr Ser Lys Met Lys His
    1325                1330                1335

Leu Asn Ile Asn Glu Asp Ile Tyr His Glu Thr Gln Thr Glu Lys
    1340                1345                1350

Glu Glu Met Val Ala Glu Ile Tyr Gly Lys Phe Ser Asn Ile Asp
    1355                1360                1365

Gln Asn Glu Gly Asp Leu His Val Asn Thr Arg Val Lys Asn Asp
    1370                1375                1380

Leu Val Cys Asn Ser Glu Lys Leu Ser Ser Pro Asp Leu Tyr Thr
    1385                1390                1395

Asn Gly Ile Glu Glu Phe Gly Asp Ser Phe Gln Leu Asp Thr Gln
    1400                1405                1410

Thr Glu Lys Met Leu His Gly His Asp Phe Ser His Arg Asn Val
    1415                1420                1425

Glu Phe Asn Val Arg Glu Asn Lys Gln Asp Asn Gln Val Asp Ser
    1430                1435                1440

Thr Ser Glu Lys Val Val Lys Gln Ser Ser Phe Leu Glu Lys Glu
    1445                1450                1455

Asn Arg Val Ser Lys Glu Gln Asn Lys Gly Pro Phe Glu Ser Leu
    1460                1465                1470
```

-continued

```
Ser  Leu  His  Asp  Asn  Gly  Trp  Pro  Thr  Glu  Ala  Lys  Pro  Lys  Tyr
     1475                1480                1485

Asn  Ile  Ser  Leu  Thr  Asp  Ser  Gln  Leu  Glu  Asn  Ile  Leu  Asn  Tyr
     1490                1495                1500

Ser  Asn  Gln  Val  Pro  Glu  Glu  Gln  Cys  Ala  Asn  Lys  Pro  Ala
     1505                1510                1515

Glu  Gln  Arg  Glu  Asn  Asn  Glu  Ser  Ser  Asp  His  Val  Thr  Asp  Asn
     1520                1525                1530

Ser  Phe  Asp  Arg  Ser  Ser  Ser  Phe  Leu  Phe  Asp  Ser  Leu  Tyr  Asp
     1535                1540                1545

Asn  Ser  Ile  Leu  Asp  Ala  Met  Glu  Glu  Ala  Ala  Ile  Asp  Gln  Asp
     1550                1555                1560

Asn  Lys  Gly  Asp  Gln  Glu  Ala  Glu  Val  Lys  Val  Asn  Ser  Asn  Gly
     1565                1570                1575

Ser  Ser  Pro  Glu  Leu  Ile  Pro  Glu  Arg  Arg  Glu  Ala  Leu  Pro  Thr
     1580                1585                1590

Asp  Asp  Gln  Glu  Ala  Ile  Gln  Trp  Gly  Glu  Ser  Ser  Phe  Asn  Leu
     1595                1600                1605

Ser  Glu  Trp  Gly  Asp  Ser  Leu  Ile  Ile  Gly  Glu  Gln  Tyr  Leu  Glu
     1610                1615                1620

Lys  Ile  Ser  Lys  Ala  Cys  Asp  Gly  Pro  Arg  Leu  Gly  Ala  Glu  Lys
     1625                1630                1635

Pro  Ser  Tyr  Thr  Asp  Asp  Ile  Val  Ser  Glu  Leu  Asn  Val  Ser  Gln
     1640                1645                1650

Ser  Asn  Glu  Tyr  Gln  Gln  Lys  Val  Glu  Arg  His  Arg  Leu  Asn  Ser
     1655                1660                1665

Ser  Ser  Phe  His  Ile  Ser  Pro  Gly  Met  Gln  Asp  Leu  Phe  Asp  Lys
     1670                1675                1680

Trp  Ser  Asp  Gln  Phe  Ser  Thr  Val  Pro  Asp  Ala  Thr  Ala  His  Ser
     1685                1690                1695

Asn  Ser  Leu  Val  Glu  Pro  Asn  Ala  Val  Val  Leu  Glu  Glu  Ala  Val
     1700                1705                1710

Ser  Leu  Thr  Lys  Thr  Lys  Glu  Ile  Glu  Lys  Glu  Gly  Pro  Glu  Val
     1715                1720                1725

Ser  Arg  Ser  Glu  Asp  Phe  Val  Thr  Val  Gln  Ala  Lys  Lys  Val  Thr
     1730                1735                1740

Pro  Ser  Asp  Leu  Val  Pro  Pro  Thr  Gln  Val  Leu  Glu  Pro  Val  Thr
     1745                1750                1755

Pro  Arg  Val  Lys  Met  Thr  Thr  Ser  Ala  Ile  Gln  Ser  Pro  Lys  Asn
     1760                1765                1770

Val  Thr  Lys  Gln  Arg  Ser  Glu  Leu  Asp  Pro  Asn  Ile  Lys  Ser  Cys
     1775                1780                1785

Thr  Gln  Arg  Tyr  His  Gln  Pro  Cys  Leu  Arg  Thr  Asn  Ser  Thr  Ser
     1790                1795                1800

Val  Leu  Gly  Ala  Pro  Leu  Ala  Asp  Glu  Gly  Phe  Thr  Arg  Leu  Ser
     1805                1810                1815

Gln  Cys  Pro  Ser  Leu  Pro  Ala  Ser  Asn  Ser  Cys  Ser  Pro  Glu  Thr
     1820                1825                1830

Phe  Ser  Ile  Ile  Asp  Val  Ala  Ser  Asp  Arg  Arg  Leu  Phe  Glu  Thr
     1835                1840                1845

Phe  Val  Asn  Glu  Trp  Lys  Thr  Lys  Glu  Arg  Phe  Ser  Leu  Ala  Val
     1850                1855                1860

Ala  Cys  Glu  Lys  Thr  Asp  Ser  Thr  Ser  Val  Gln  Pro  Glu  Thr  Val
```

```
                    1865                1870                1875

Ile Gly Gly Lys Phe Lys Lys Pro Thr Thr Pro Met Arg Asn Lys
            1880                1885                1890

Arg Lys Asp Gly Phe Leu Leu Lys Gly Tyr Glu Asp Leu Val Val
            1895                1900                1905

Ile Gly Ile Ser Val Ser Trp Gly Ala Lys Asp Ala Tyr Phe Val
            1910                1915                1920

Ser Leu Gln Gln Glu Leu Val Asp Thr Asp Ile Ser Ala Ser Leu
            1925                1930                1935

Ala Pro Pro Pro Leu Asp Asp Thr Leu Thr Val Glu Glu Arg Leu
            1940                1945                1950

Lys Gln Ile Gln Ser Cys Leu Gln Lys Asp Ser Ser Val Thr Val
            1955                1960                1965

Thr Tyr Asp Phe Ile His Leu Tyr Lys Ile Leu Leu Leu Ala Cys
            1970                1975                1980

Glu Leu Ala Val Arg Gly Thr Phe Glu Asp Pro Lys Ile Ala Cys
            1985                1990                1995

Trp Leu Leu Asp Ser Ser Ser Lys Glu Arg Thr Leu His Asn Met
            2000                2005                2010

Val Thr Ser Phe Ala Thr Glu Asp Leu Pro Leu Leu Glu Gly Ile
            2015                2020                2025

Ser Ala Gly Gln Gly Val Gln Ser Leu Gly Ile Phe Gly Glu Ala
            2030                2035                2040

Ser Gln Pro Gly Arg Tyr Arg Ala Ala Ile Glu Ser Val Leu Val
            2045                2050                2055

Phe Arg Val Met Thr Gln Leu Asn Cys Leu Leu Glu Lys Asp Gly
            2060                2065                2070

Phe Leu Asp Val Phe Lys Lys Val Glu Met Pro Thr Gln Tyr Cys
            2075                2080                2085

Leu Ala Leu Leu Glu Leu Asn Gly Ile Gly Phe Ser Ile Ala Glu
            2090                2095                2100

Cys Glu Ala Gln Lys His Val Met Gln Ala Lys Leu Ser Ala Leu
            2105                2110                2115

Glu Ser Gln Ala Tyr Gln Leu Ala Gly His Ser Phe Ser Leu Thr
            2120                2125                2130

Ser Pro Glu Asp Val Ala Glu Val Leu Phe Leu Glu Leu Lys Leu
            2135                2140                2145

Pro Pro Asn Gly Asp Leu Asn Gly Leu Lys Asn Lys Lys Thr Leu
            2150                2155                2160

Gly Tyr Thr Arg Arg Ala Gly Ala Arg Ile Lys Leu Ser Lys Gln
            2165                2170                2175

Phe Ser Thr Thr Lys Asp Val Leu Glu Lys Leu Lys Pro Leu His
            2180                2185                2190

Pro Leu Pro Gly Val Ile Leu Glu Trp Arg Arg Ile Thr Asn Ala
            2195                2200                2205

Leu Thr Lys Val Val Phe Pro Leu Gln Arg Glu Lys Lys Trp His
            2210                2215                2220

Ser His Leu Lys Met Asp Arg Ile His Pro Ile Ser Gln Ser His
            2225                2230                2235

Thr Ala Thr Gly Arg Val Ser Phe Thr Glu Pro Asn Ile Gln Asn
            2240                2245                2250

Val Pro Lys Asp Phe Glu Ile Gln Met Pro Thr Leu Ile Glu Glu
            2255                2260                2265
```

```
Ser Gln Thr Ser Gln Asn Gly Gly Ser Lys Met Trp Cys Lys Arg
        2270                2275                2280

Thr Lys Ile Asn Arg Gln Leu Ala Pro Leu Leu Lys Val Ser Asp
    2285                2290                2295

Lys Ser Pro Asp Lys Gly Met Gln Phe Ser Val Ser Met Arg His
    2300                2305                2310

Ala Phe Val Pro Phe Ser Gly Gly Leu Ile Leu Ala Val Asp Tyr
    2315                2320                2325

Ser Gln Leu Glu Leu Arg Ile Leu Ala His Leu Ser Arg Asp Arg
    2330                2335                2340

Arg Leu Leu His Val Leu Asn Ser Gly Ala Asp Val Phe Lys Ser
    2345                2350                2355

Ile Ala Ala Glu Trp Lys Met Val Asp Pro Ala Ser Val Asp Asp
    2360                2365                2370

Asn Met Arg Gln Gln Ala Lys Gln Ile Cys Tyr Gly Ile Ile Tyr
    2375                2380                2385

Gly Met Gly Ala Lys Ser Leu Gly Glu Gln Met Gly Ile Glu Glu
    2390                2395                2400

Asn Asp Ala Ala Cys Tyr Ile Glu Thr Phe Lys Ser Arg Tyr Asn
    2405                2410                2415

Gly Ile Gln Asn Phe Leu Arg Glu Thr Val Gln Lys Cys Gly Lys
    2420                2425                2430

Asn Gly Tyr Val Lys Thr Leu Leu Gly Arg Lys Arg Phe Leu Pro
    2435                2440                2445

Gly Ile Lys Asp Ser Asn Val Tyr Ile Lys Ser His Ala Glu Arg
    2450                2455                2460

Gln Ala Val Asn Thr Thr Val Gln Gly Ser Ala Ala Asp Ile Val
    2465                2470                2475

Lys Leu Ala Thr Ile Asn Ile Gln Arg Arg Ile Glu Glu Ala Phe
    2480                2485                2490

Pro Gly Val Pro Thr Ser His Gln His Pro Ser Ile Arg Leu Gly
    2495                2500                2505

Gly Arg His Arg Asn Gln Phe Arg Pro Leu Arg Gly Gly Tyr Phe
    2510                2515                2520

Ile Leu Gln Leu His Asp Glu Leu Ile Tyr Glu Val Ala Glu Glu
    2525                2530                2535

Asp Val Ile Gln Val Ala Gln Ile Val Lys Arg Glu Met Glu Ser
    2540                2545                2550

Val Val Lys Leu Tyr Val Lys Leu Arg Val Lys Val Lys Val Gly
    2555                2560                2565

Pro Ser Trp Gly Asn Leu Gln Asp Leu Asp Ile
    2570                2575

<210> SEQ ID NO 4
<211> LENGTH: 2059
<212> TYPE: PRT
<213> ORGANISM: Drosophila melanogaster

<400> SEQUENCE: 4

Met Ala Phe Ser Gln Ser Phe Asn Phe Gly Asn Ser Thr Leu Met Ala
1               5                   10                  15

Leu Glu Lys Gly Met Gln Ala Asp Asp Lys Glu Asn Ala Gln Pro Gly
            20                  25                  30

Asn Gly Asn Ile Gln Val Gln Ser Ala Gly Asn Glu Val Asn Ser Glu
```

-continued

```
                35                  40                  45
Ile Gln Glu Ile Asn Ser Glu Phe Phe Arg Asp Glu Phe Ser Tyr Glu
 50                  55                  60
Val Asn Gln Ala His Lys Pro Ala Glu Gln Ser Val Val Asn Val Ser
 65                  70                  75                  80
Gln Val Gln Gln His Met Ala Val Val Ser Asn Gln Asp Ser Glu Asp
                     85                  90                  95
Gln Ser Arg Ser Ser Ala Leu Asn Asp Gln Ile Cys Thr Gln Ser Ser
                100                 105                 110
Phe Glu Gly Glu Asp Ala Gly Ala Asp Ala Val Leu Asp Gln Pro Asn
                115                 120                 125
Leu Asp Glu Asn Ser Phe Leu Cys Pro Ala Gln Asp Glu Glu Ala Ser
130                 135                 140
Glu Gln Leu Lys Glu Asp Ile Leu His Ser His Ser Val Leu Ala Lys
145                 150                 155                 160
Gln Glu Phe Tyr Gln Glu Ile Ser Gln Val Thr Gln Asn Leu Ser Ser
                165                 170                 175
Met Ser Pro Asn Gln Leu Arg Val Ser Pro Asn Ser Ser Arg Ile Arg
                180                 185                 190
Glu Ala Met Pro Glu Arg Pro Ala Met Pro Leu Asp Leu Asn Thr Leu
                195                 200                 205
Arg Ser Ile Ser Ala Trp Asn Leu Pro Met Ser Ile Gln Ala Glu Tyr
210                 215                 220
Lys Lys Lys Gly Val Val Asp Met Phe Asp Trp Gln Val Glu Cys Leu
225                 230                 235                 240
Ser Lys Pro Arg Leu Leu Phe Glu His Cys Asn Leu Val Tyr Ser Ala
                245                 250                 255
Pro Thr Ser Ala Gly Lys Thr Leu Val Ser Glu Ile Leu Met Leu Lys
                260                 265                 270
Thr Val Leu Glu Arg Gly Lys Lys Val Leu Leu Ile Leu Pro Phe Ile
                275                 280                 285
Ser Val Val Arg Glu Lys Met Phe Tyr Met Gln Asp Leu Leu Thr Pro
290                 295                 300
Ala Gly Tyr Arg Val Glu Gly Phe Tyr Gly Gly Tyr Thr Pro Pro Gly
305                 310                 315                 320
Gly Phe Glu Ser Leu His Val Ala Ile Cys Thr Ile Glu Lys Ala Asn
                325                 330                 335
Ser Ile Val Asn Lys Leu Met Glu Gln Gly Lys Leu Glu Thr Ile Gly
                340                 345                 350
Met Val Val Asp Glu Val His Leu Ile Ser Asp Lys Gly Arg Gly
                355                 360                 365
Tyr Ile Leu Glu Leu Leu Ala Lys Ile Leu Tyr Met Ser Arg Arg
                370                 375                 380
Asn Gly Leu Gln Ile Gln Val Ile Thr Met Ser Ala Thr Leu Glu Asn
385                 390                 395                 400
Val Gln Leu Leu Gln Ser Trp Leu Asp Ala Glu Leu Tyr Ile Thr Asn
                405                 410                 415
Tyr Arg Pro Val Ala Leu Lys Glu Met Ile Lys Val Gly Thr Val Ile
                420                 425                 430
Tyr Asp His Arg Leu Lys Leu Val Arg Asp Val Ala Lys Gln Lys Val
                435                 440                 445
Leu Leu Lys Gly Leu Glu Asn Asp Ser Asp Val Ala Leu Leu Cys
450                 455                 460
```

-continued

```
Ile Glu Thr Leu Leu Glu Gly Cys Ser Val Ile Val Phe Cys Pro Ser
465                 470                 475                 480

Lys Asp Trp Cys Glu Asn Leu Ala Val Gln Leu Ala Thr Ala Ile His
            485                 490                 495

Val Gln Ile Lys Ser Glu Thr Val Leu Gly Gln Arg Leu Arg Thr Asn
        500                 505                 510

Leu Asn Pro Arg Ala Ile Ala Glu Val Lys Gln Gln Leu Arg Asp Ile
    515                 520                 525

Pro Thr Gly Leu Asp Gly Val Met Ser Lys Ala Ile Thr Tyr Ala Cys
530                 535                 540

Ala Phe His His Ala Gly Leu Thr Thr Glu Glu Arg Asp Ile Ile Glu
545                 550                 555                 560

Ala Ser Phe Lys Ala Gly Ala Leu Lys Val Leu Val Ala Thr Ser Thr
            565                 570                 575

Leu Ser Ser Gly Val Asn Leu Pro Ala Arg Arg Val Leu Ile Arg Ser
        580                 585                 590

Pro Leu Phe Gly Gly Lys Gln Met Ser Ser Leu Thr Tyr Arg Gln Met
    595                 600                 605

Ile Gly Arg Ala Gly Arg Met Gly Lys Asp Thr Leu Gly Glu Ser Ile
610                 615                 620

Leu Ile Cys Asn Glu Ile Asn Ala Arg Met Gly Arg Asp Leu Val Val
625                 630                 635                 640

Ser Glu Leu Gln Pro Ile Thr Ser Cys Leu Asp Met Asp Gly Ser Thr
            645                 650                 655

His Leu Lys Arg Ala Leu Leu Glu Val Ile Ser Ser Gly Val Ala Asn
        660                 665                 670

Thr Lys Glu Asp Ile Asp Phe Phe Val Asn Cys Thr Leu Leu Ser Ala
    675                 680                 685

Gln Lys Ala Phe His Ala Lys Glu Lys Pro Pro Asp Glu Glu Ser Asp
690                 695                 700

Ala Asn Tyr Ile Asn Asp Ala Leu Asp Phe Leu Val Glu Tyr Glu Phe
705                 710                 715                 720

Val Arg Leu Gln Arg Asn Glu Glu Arg Glu Thr Ala Val Tyr Val Ala
            725                 730                 735

Thr Arg Leu Gly Ala Ala Cys Leu Ala Ser Ser Met Pro Pro Thr Asp
        740                 745                 750

Gly Leu Ile Leu Phe Ala Glu Leu Gln Lys Ser Arg Arg Ser Phe Val
    755                 760                 765

Leu Glu Ser Glu Leu His Ala Val Tyr Leu Val Thr Pro Tyr Ser Val
770                 775                 780

Cys Tyr Gln Leu Gln Asp Ile Asp Trp Leu Leu Tyr Val His Met Trp
785                 790                 795                 800

Glu Lys Leu Ser Ser Pro Met Lys Lys Val Gly Glu Leu Val Gly Val
            805                 810                 815

Arg Asp Ala Phe Leu Tyr Lys Ala Leu Arg Gly Gln Thr Lys Leu Asp
        820                 825                 830

Tyr Lys Gln Met Gln Ile His Lys Arg Phe Tyr Ile Ala Leu Ala Leu
    835                 840                 845

Glu Glu Leu Val Asn Glu Thr Pro Ile Asn Val Val His Lys Tyr
850                 855                 860

Lys Cys His Arg Gly Met Leu Gln Ser Leu Gln Gln Met Ala Ser Thr
865                 870                 875                 880
```

```
Phe Ala Gly Ile Val Thr Ala Phe Cys Asn Ser Leu Gln Trp Ser Thr
                    885                 890                 895

Leu Ala Leu Ile Val Ser Gln Phe Lys Asp Arg Leu Phe Phe Gly Ile
            900                 905                 910

His Arg Asp Leu Ile Asp Leu Met Arg Ile Pro Asp Leu Ser Gln Lys
            915                 920                 925

Arg Ala Arg Ala Leu Phe Asp Ala Gly Ile Thr Ser Leu Val Glu Leu
        930                 935                 940

Ala Gly Ala Asp Pro Val Glu Leu Glu Lys Val Leu Tyr Asn Ser Ile
945                 950                 955                 960

Ser Phe Asp Ser Ala Lys Gln His Asp His Glu Asn Ala Asp Glu Ala
                965                 970                 975

Ala Lys Arg Asn Val Val Arg Asn Phe Tyr Ile Thr Gly Lys Ala Gly
            980                 985                 990

Met Thr Val Ser Glu Ala Ala Lys Leu Leu Ile Gly Glu Ala Arg Gln
            995                 1000                1005

Phe Val Gln His Glu Ile Gly Leu Gly Thr Ile Lys Trp Thr Gln
    1010                1015                1020

Thr Gln Ala Gly Val Glu Ile Ala Ser Arg Ala Ile His Asp Gly
    1025                1030                1035

Gly Glu Val Asp Leu His Met Ser Leu Glu Glu Gln Pro Pro
    1040                1045                1050

Val Lys Arg Lys Leu Ser Ile Glu Glu Asn Gly Thr Ala Asn Ser
    1055                1060                1065

Gln Lys Asn Pro Arg Leu Glu Thr Val Val Asp Thr Gln Arg Gly
    1070                1075                1080

Tyr Lys Val Asp Lys Asn Ile Ala Asn Gln Ser Lys Met Asn Pro
    1085                1090                1095

Asn Leu Lys Glu Ile Asp Ala Gln Asn Lys Ala Arg Arg Asn Ser
    1100                1105                1110

Thr Ala His Met Asp Asn Leu Asn Pro Ile Ser Asn Asp Pro Cys
    1115                1120                1125

Gln Asn Asn Val Asn Val Lys Thr Ala Gln Pro Ile Ile Ser Asn
    1130                1135                1140

Leu Asn Asp Ile Gln Lys Gln Gly Ser Gln Ile Glu Lys Met Lys
    1145                1150                1155

Ile Asn Pro Ala Thr Val Val Cys Ser Pro Gln Leu Ala Asn Glu
    1160                1165                1170

Glu Lys Pro Ser Thr Ser Gln Ser Ala Arg Arg Lys Leu Val Asn
    1175                1180                1185

Glu Gly Met Ala Glu Arg Arg Arg Val Ala Leu Met Lys Ile Gln
    1190                1195                1200

Gln Arg Thr Gln Lys Glu Asn Gln Ser Lys Asp Gln Pro Ile Gln
    1205                1210                1215

Ala Ser Arg Ser Asn Gln Leu Ser Ser Pro Val Asn Arg Thr Pro
    1220                1225                1230

Ala Asn Arg Trp Thr Gln Ser Glu Asn Pro Asn Asn Glu Met Asn
    1235                1240                1245

Asn Ser Gln Leu Pro Arg Arg Asn Pro Arg Asn Gln Ser Pro Val
    1250                1255                1260

Pro Asn Ala Asn Arg Thr Ala Ser Arg Lys Val Ser Asn Ala Glu
    1265                1270                1275

Glu Asp Leu Phe Met Ala Asp Asp Ser Phe Met Leu Asn Thr Gly
```

```
            1280              1285              1290
Leu Ala Ala Ala Leu Thr Ala Ala Glu Ser Lys Ile Ala Ser Cys
    1295              1300              1305
Thr Glu Ala Asp Val Ile Pro Ser Ser Gln Pro Lys Glu Pro Glu
    1310              1315              1320
Val Ile Gly Ala Leu Thr Pro His Ala Ser Arg Leu Lys Arg Ser
    1325              1330              1335
Asp Gln Leu Arg Ser Gln Arg Ile Gln Ser Pro Ser Pro Thr Pro
    1340              1345              1350
Gln Arg Glu Ile Glu Ile Asp Leu Glu Ser Lys Asn Glu Ser Asn
    1355              1360              1365
Gly Val Ser Ser Met Glu Ile Ser Asp Met Ser Met Glu Asn Pro
    1370              1375              1380
Leu Met Lys Asn Pro Leu His Leu Asn Ala Ser His Ile Met Ser
    1385              1390              1395
Cys Ser Lys Val Asp Glu Thr Ala Ser Ser Phe Ser Ser Ile Asp
    1400              1405              1410
Ile Ile Asp Val Cys Gly His Arg Asn Ala Phe Gln Ala Ala Ile
    1415              1420              1425
Ile Glu Ile Asn Asn Ala Thr Arg Leu Gly Phe Ser Val Gly Leu
    1430              1435              1440
Gln Ala Gln Ala Gly Lys Gln Lys Pro Leu Ile Gly Ser Asn Leu
    1445              1450              1455
Leu Ile Asn Gln Val Ala Ala Ala Glu Asn Arg Glu Ala Ala Ala
    1460              1465              1470
Arg Glu Arg Val Leu Phe Gln Val Asp Asp Thr Asn Phe Ile Ser
    1475              1480              1485
Gly Val Ser Phe Cys Leu Ala Asp Asn Val Ala Tyr Tyr Trp Asn
    1490              1495              1500
Met Gln Ile Asp Glu Arg Ala Ala Tyr Gln Gly Val Pro Thr Pro
    1505              1510              1515
Leu Lys Val Gln Glu Leu Cys Asn Leu Met Ala Arg Lys Asp Leu
    1520              1525              1530
Thr Leu Val Met His Asp Gly Lys Glu Gln Leu Lys Met Leu Arg
    1535              1540              1545
Lys Ala Ile Pro Gln Leu Lys Arg Ile Ser Ala Lys Leu Glu Asp
    1550              1555              1560
Ala Lys Val Ala Asn Trp Leu Leu Gln Pro Asp Lys Thr Val Asn
    1565              1570              1575
Phe Leu Asn Met Cys Gln Thr Phe Ala Pro Glu Cys Thr Gly Leu
    1580              1585              1590
Ala Asn Leu Cys Gly Ser Gly Arg Gly Tyr Ser Ser Tyr Gly Leu
    1595              1600              1605
Asp Thr Ser Ser Ala Ile Leu Pro Arg Ile Arg Thr Ala Ile Glu
    1610              1615              1620
Ser Cys Val Thr Leu His Ile Leu Gln Gly Gln Thr Glu Asn Leu
    1625              1630              1635
Ser Arg Ile Gly Asn Gly Asp Leu Leu Lys Phe Phe His Asp Ile
    1640              1645              1650
Glu Met Pro Ile Gln Leu Thr Leu Cys Gln Met Glu Leu Val Gly
    1655              1660              1665
Phe Pro Ala Gln Lys Gln Arg Leu Gln Gln Leu Tyr Gln Arg Met
    1670              1675              1680
```

```
Val Ala Val Met Lys Lys Val Glu Thr Lys Ile Tyr Glu Gln His
    1685            1690                1695

Gly Ser Arg Phe Asn Leu Gly Ser Ser Gln Ala Val Ala Lys Val
    1700            1705                1710

Leu Gly Leu His Arg Lys Ala Lys Gly Arg Val Thr Thr Ser Arg
    1715            1720                1725

Gln Val Leu Glu Lys Leu Asn Ser Pro Ile Ser His Leu Ile Leu
    1730            1735                1740

Gly Tyr Arg Lys Leu Ser Gly Leu Leu Ala Lys Ser Ile Gln Pro
    1745            1750                1755

Leu Met Glu Cys Cys Gln Ala Asp Arg Ile His Gly Gln Ser Ile
    1760            1765                1770

Thr Tyr Thr Ala Thr Gly Arg Ile Ser Met Thr Glu Pro Asn Leu
    1775            1780                1785

Gln Asn Val Ala Lys Glu Phe Ser Ile Gln Val Gly Ser Asp Val
    1790            1795                1800

Val His Ile Ser Cys Arg Ser Pro Phe Met Pro Thr Asp Glu Ser
    1805            1810                1815

Arg Cys Leu Leu Ser Ala Asp Phe Cys Gln Leu Glu Met Arg Ile
    1820            1825                1830

Leu Ala His Met Ser Gln Asp Lys Ala Leu Leu Glu Val Met Lys
    1835            1840                1845

Ser Ser Gln Asp Leu Phe Ile Ala Ile Ala Ala His Trp Asn Lys
    1850            1855                1860

Ile Glu Glu Ser Glu Val Thr Gln Asp Leu Arg Asn Ser Thr Lys
    1865            1870                1875

Gln Val Cys Tyr Gly Ile Val Tyr Gly Met Gly Met Arg Ser Leu
    1880            1885                1890

Ala Glu Ser Leu Asn Cys Ser Glu Gln Glu Ala Arg Met Ile Ser
    1895            1900                1905

Asp Gln Phe His Gln Ala Tyr Lys Gly Ile Arg Asp Tyr Thr Thr
    1910            1915                1920

Arg Val Val Asn Phe Ala Arg Ser Lys Gly Phe Val Glu Thr Ile
    1925            1930                1935

Thr Gly Arg Arg Arg Tyr Leu Glu Asn Ile Asn Ser Asp Val Glu
    1940            1945                1950

His Leu Lys Asn Gln Ala Glu Arg Gln Ala Val Asn Ser Thr Ile
    1955            1960                1965

Gln Gly Ser Ala Ala Asp Ile Ala Lys Asn Ala Ile Leu Lys Met
    1970            1975                1980

Glu Lys Asn Ile Glu Arg Tyr Arg Glu Lys Leu Ala Leu Gly Asp
    1985            1990                1995

Asn Ser Val Asp Leu Val Met His Leu His Asp Glu Leu Ile Phe
    2000            2005                2010

Glu Val Pro Thr Gly Lys Ala Lys Lys Ile Ala Lys Val Leu Ser
    2015            2020                2025

Leu Thr Met Glu Asn Cys Val Lys Leu Ser Val Pro Leu Lys Val
    2030            2035                2040

Lys Leu Arg Ile Gly Arg Ser Trp Gly Glu Phe Lys Glu Val Ser
    2045            2050                2055

Val
```

```
<210> SEQ ID NO 5
<211> LENGTH: 900
<212> TYPE: PRT
<213> ORGANISM: Homo sapiens

<400> SEQUENCE: 5

Met Glu Asn Tyr Glu Ala Leu Val Gly Phe Asp Leu Cys Asn Thr Pro
1               5                   10                  15

Leu Ser Ser Val Ala Gln Lys Ile Met Ser Ala Met His Ser Gly Asp
            20                  25                  30

Leu Val Asp Ser Lys Thr Trp Gly Lys Ser Thr Glu Thr Met Glu Val
        35                  40                  45

Ile Asn Lys Ser Ser Val Lys Tyr Ser Val Gln Leu Glu Asp Arg Lys
    50                  55                  60

Thr Gln Ser Pro Glu Lys Lys Asp Leu Lys Ser Leu Arg Ser Gln Thr
65                  70                  75                  80

Ser Arg Gly Ser Ala Lys Leu Ser Pro Gln Ser Phe Ser Val Arg Leu
                85                  90                  95

Thr Asp Gln Leu Ser Ala Asp Gln Lys Ser Ile Ser Ser Leu
            100                 105                 110

Thr Leu Ser Ser Cys Leu Ile Pro Gln Tyr Asn Gln Glu Ala Ser Val
        115                 120                 125

Leu Gln Lys Lys Gly His Lys Arg Lys His Phe Leu Met Glu Asn Ile
    130                 135                 140

Asn Asn Glu Asn Lys Gly Ser Ile Asn Leu Lys Arg Lys His Ile Thr
145                 150                 155                 160

Tyr Asn Asn Leu Ser Glu Lys Thr Ser Lys Gln Met Ala Leu Glu Glu
                165                 170                 175

Asp Thr Asp Asp Ala Glu Gly Tyr Leu Asn Ser Gly Asn Ser Gly Ala
            180                 185                 190

Leu Lys Lys His Phe Cys Asp Ile Arg His Leu Asp Asp Trp Ala Lys
        195                 200                 205

Ser Gln Leu Ile Glu Met Leu Lys Gln Ala Ala Ala Leu Val Ile Thr
    210                 215                 220

Val Met Tyr Thr Asp Gly Ser Thr Gln Leu Gly Ala Asp Gln Thr Pro
225                 230                 235                 240

Val Ser Ser Val Arg Gly Ile Val Val Leu Val Lys Arg Gln Ala Glu
                245                 250                 255

Gly Gly His Gly Cys Pro Asp Ala Pro Ala Cys Gly Pro Val Leu Glu
            260                 265                 270

Gly Phe Val Ser Asp Asp Pro Cys Ile Tyr Ile Gln Ile Glu His Ser
        275                 280                 285

Ala Ile Trp Asp Gln Glu Gln Glu Ala His Gln Gln Phe Ala Arg Asn
    290                 295                 300

Val Leu Phe Gln Thr Met Lys Cys Lys Cys Pro Val Ile Cys Phe Asn
305                 310                 315                 320

Ala Lys Asp Phe Val Arg Ile Val Leu Gln Phe Gly Asn Asp Gly
                325                 330                 335

Ser Trp Lys His Val Ala Asp Phe Ile Gly Leu Asp Pro Arg Ile Ala
            340                 345                 350

Ala Trp Leu Ile Asp Pro Ser Asp Ala Thr Pro Ser Phe Glu Asp Leu
        355                 360                 365

Val Glu Lys Tyr Cys Glu Lys Ser Ile Thr Val Lys Val Asn Ser Thr
    370                 375                 380
```

```
Tyr Gly Asn Ser Ser Arg Asn Ile Val Asn Gln Asn Val Arg Glu Asn
385                 390                 395                 400

Leu Lys Thr Leu Tyr Arg Leu Thr Met Asp Leu Cys Ser Lys Leu Lys
            405                 410                 415

Asp Tyr Gly Leu Trp Gln Leu Phe Arg Thr Leu Glu Leu Pro Leu Ile
            420                 425                 430

Pro Ile Leu Ala Val Met Glu Ser His Ala Ile Gln Val Asn Lys Glu
            435                 440                 445

Glu Met Glu Lys Thr Ser Ala Leu Leu Gly Ala Arg Leu Lys Glu Leu
    450                 455                 460

Glu Gln Glu Ala His Phe Val Ala Gly Glu Arg Phe Leu Ile Thr Ser
465                 470                 475                 480

Asn Asn Gln Leu Arg Glu Ile Leu Phe Gly Lys Leu Lys Leu His Leu
                485                 490                 495

Leu Ser Gln Arg Asn Ser Leu Pro Arg Thr Gly Leu Gln Lys Tyr Pro
                500                 505                 510

Ser Thr Ser Glu Ala Val Leu Asn Ala Leu Arg Asp Leu His Pro Leu
            515                 520                 525

Pro Lys Ile Ile Leu Glu Tyr Arg Gln Val His Lys Ile Lys Ser Thr
            530                 535                 540

Phe Val Asp Gly Leu Leu Ala Cys Met Lys Lys Gly Ser Ile Ser Ser
545                 550                 555                 560

Thr Trp Asn Gln Thr Gly Thr Val Thr Gly Arg Leu Ser Ala Lys His
                565                 570                 575

Pro Asn Ile Gln Gly Ile Ser Lys His Pro Ile Gln Ile Thr Thr Pro
            580                 585                 590

Lys Asn Phe Lys Gly Lys Glu Asp Lys Ile Leu Thr Ile Ser Pro Arg
            595                 600                 605

Ala Met Phe Val Ser Ser Lys Gly His Thr Phe Leu Ala Ala Asp Phe
            610                 615                 620

Ser Gln Ile Glu Leu Arg Ile Leu Thr His Leu Ser Gly Asp Pro Glu
625                 630                 635                 640

Leu Leu Lys Leu Phe Gln Glu Ser Glu Arg Asp Asp Val Phe Ser Thr
                645                 650                 655

Leu Thr Ser Gln Trp Lys Asp Val Pro Val Glu Gln Val Thr His Ala
            660                 665                 670

Asp Arg Glu Gln Thr Lys Lys Val Val Tyr Ala Val Val Tyr Gly Ala
                675                 680                 685

Gly Lys Glu Arg Leu Ala Ala Cys Leu Gly Val Pro Ile Gln Glu Ala
    690                 695                 700

Ala Gln Phe Leu Glu Ser Phe Leu Gln Lys Tyr Lys Lys Ile Lys Asp
705                 710                 715                 720

Phe Ala Arg Ala Ala Ile Ala Gln Cys His Gln Thr Gly Cys Val Val
            725                 730                 735

Ser Ile Met Gly Arg Arg Arg Pro Leu Pro Arg Ile His Ala His Asp
            740                 745                 750

Gln Gln Leu Arg Ala Gln Ala Glu Arg Gln Ala Val Asn Phe Val Val
            755                 760                 765

Gln Gly Ser Ala Ala Asp Leu Cys Lys Leu Ala Met Ile His Val Phe
            770                 775                 780

Thr Ala Val Ala Ala Ser His Thr Leu Thr Ala Arg Leu Val Ala Gln
785                 790                 795                 800

Ile His Asp Glu Leu Leu Phe Glu Val Glu Asp Pro Gln Ile Pro Glu
```

```
                       805                 810                 815
        Cys Ala Ala Leu Val Arg Arg Thr Met Glu Ser Leu Glu Gln Val Gln
                    820                 825                 830

Ala Leu Glu Leu Gln Leu Gln Val Pro Leu Lys Val Ser Leu Ser Ala
                    835                 840                 845

Gly Arg Ser Trp Gly His Leu Val Pro Leu Gln Glu Ala Trp Gly Pro
                    850                 855                 860

Pro Pro Gly Pro Cys Arg Thr Glu Ser Pro Ser Asn Ser Leu Ala Ala
        865                 870                 875                 880

Pro Gly Ser Pro Ala Ser Thr Gln Pro Pro Leu His Phe Ser Pro
                        885                 890                 895

Ser Phe Cys Leu
                    900

<210> SEQ ID NO 6
<211> LENGTH: 864
<212> TYPE: PRT
<213> ORGANISM: Mus musculus

<400> SEQUENCE: 6

Met Glu Asn Tyr Glu Ala Cys Val Gly Phe Asp Val Cys Glu Ile Pro
1               5                   10                  15

Leu Ser Ala Val Ala Gln Lys Ile Met Ser Ala Met Arg Ser Gly Asp
            20                  25                  30

Phe Met Asp Ser Arg Asn Glu Gly Glu Ser Thr Asn Thr Ser Lys Val
        35                  40                  45

Ala Lys Lys Ser Ser Val His Tyr Ser Val Leu Ala Glu His Glu Glu
    50                  55                  60

Thr Gln Ser Leu Gly Thr Lys Asn Pro Glu Ser Leu Ile Thr Gln Thr
65                  70                  75                  80

Pro Arg Gly Ser Ile Glu Leu Cys Pro Gln Pro Ser Ile Thr Lys Leu
                85                  90                  95

Thr Cys Gln Leu Ser Ala Gly Gln Val Gln Asn Ser Ile Ser Ser Leu
            100                 105                 110

Gly Leu Ser Ser Tyr Leu Ile Pro Gln Cys Asp Gln Glu Ala Ser Val
        115                 120                 125

Leu Pro Asn Met Glu His Lys Arg Gln His Phe Leu Lys Glu Asn Ile
    130                 135                 140

Gly Lys Glu Asp Lys Asp Asn Ser Ser Leu Lys Arg Lys Tyr Ile Thr
145                 150                 155                 160

Cys Ser Lys Ser Ser Glu Lys Ala Ser Lys His Thr Ala Leu Glu Lys
                165                 170                 175

Asp Thr Asp Gly Thr Glu Ser Trp Pro Asn Ser Arg Asp Thr Arg Ala
            180                 185                 190

Leu Gly Glu Arg Leu Cys Asp Val Arg Tyr Leu Gly Asp Leu Ala Lys
        195                 200                 205

Ala Gln Leu Met Asp Ala Leu Lys Gln Ala Ala Leu Val Val Thr
    210                 215                 220

Leu Met Tyr Lys Asp Gly Ser Thr Gln Leu Ser Ala Lys Glu Ala Leu
225                 230                 235                 240

Thr Cys Thr Val Lys Gly Ile Val Val Leu Lys Ser His Val Gly
                245                 250                 255

Asn Ser Thr Leu Thr Leu Pro Ala His Gly Gly Ala Leu Glu Lys Asp
            260                 265                 270
```

-continued

```
Phe Ile Ser Glu Asp His Cys Val Tyr Ile His Thr Glu His Ser Pro
            275                 280                 285

Phe Trp Asp Pro Lys Gln Glu Ala His Ser Leu Phe Val Arg Asn Ile
290                 295                 300

Leu Phe Trp Thr Leu Arg Cys Lys Cys Pro Val Val Cys Phe Asn Ala
305                 310                 315                 320

Lys Asp Phe Val Arg Thr Val Leu Gln Leu Tyr Gly Glu Asp Gly Ser
                325                 330                 335

Trp Lys His Val Ala Asp Phe Val Gly Leu Asp Pro Arg Val Ala Ala
            340                 345                 350

Trp Leu Ile Asp Pro Ser Asp Thr Ala Pro Ser Phe Glu Asp Leu Val
        355                 360                 365

Ala Lys His Leu Glu Lys Ser Ile Thr Val Lys Pro Ser Ser Thr Phe
    370                 375                 380

Arg Glu Ala Ser Arg Asn Thr Leu Ser Gln Asn Val Phe Met Asn Leu
385                 390                 395                 400

Lys Ile Leu Tyr Asp Leu Thr Met Asp Leu Cys Ser Lys Leu Lys Ala
                405                 410                 415

Tyr Gly Leu Trp Gln Leu Phe Cys Thr Leu Glu Leu Pro Leu Ile Pro
            420                 425                 430

Ile Leu Ala Val Met Glu Asn His Lys Ile Pro Val Asp Lys Glu Glu
        435                 440                 445

Met Glu Arg Thr Ser Ala Leu Leu Gly Ala Arg Leu Lys Glu Leu Glu
    450                 455                 460

Gln Glu Ala His Phe Val Ala Gly Glu Gln Phe Leu Ile Met Ser Asn
465                 470                 475                 480

Asn Gln Leu Arg Glu Ile Leu Phe Gly Lys Leu Lys Leu His Leu Leu
                485                 490                 495

Ser Gln Arg Lys His Leu Pro Arg Thr Gly Leu Gln Asn Gln Leu Ser
            500                 505                 510

Thr Ser Glu Ala Met Leu Asn Ser Leu Gln Asp Leu His Pro Leu Pro
        515                 520                 525

Lys Leu Ile Leu Glu Tyr Arg Gln Val His Lys Ile Lys Ser Thr Phe
    530                 535                 540

Ile Asp Gly Leu Leu Ala Tyr Met Lys Lys Gly Ser Ile Ser Ser Thr
545                 550                 555                 560

Trp Asn Gln Thr Gly Thr Val Thr Gly Arg Leu Ser Ala Lys His Pro
                565                 570                 575

Asn Ile Gln Gly Ile Ser Lys His Pro Ile Lys Ile Ser Lys Pro Trp
            580                 585                 590

Asn Phe Lys Gly Lys Glu Glu Thr Val Thr Ile Ser Pro Arg Thr
        595                 600                 605

Leu Phe Val Ser Ser Glu Gly His Thr Phe Leu Ala Ala Asp Phe Ser
    610                 615                 620

Gln Ile Glu Leu Arg Ile Leu Ala His Leu Ser Gly Asp Pro Glu Leu
625                 630                 635                 640

Leu Lys Leu Phe Gln Glu Ser Glu Arg Asp Asp Val Phe Ser Thr Leu
                645                 650                 655

Thr Ser Gln Trp Lys Asp Ile Pro Ile Glu Arg Val Thr His Met Asp
            660                 665                 670

Arg Glu Gln Thr Lys Lys Val Val Tyr Ser Val Val Tyr Gly Ala Gly
        675                 680                 685

Lys Glu Arg Leu Ala Ala Cys Leu Gly Val Thr Val Leu Glu Ala Thr
```

```
            690                 695                 700
His Phe Leu Glu Arg Phe Leu Gln Lys Tyr Lys Ile Lys Asp Phe
705                 710                 715                 720

Ala Gln Thr Val Ile Gly Gln Cys His Ser Ala Gly Tyr Val Thr Ser
                725                 730                 735

Ile Leu Gly Arg Arg Pro Leu Pro Arg Ile Cys Ala Gln Asp Gln
                740                 745                 750

Gln Leu Arg Ala Gln Ala Glu Arg Gln Ala Val Asn Phe Val Val Gln
                755                 760                 765

Gly Ser Ala Ala Asp Leu Cys Lys Leu Ala Met Ile Arg Ile Ser Thr
770                 775                 780

Ala Val Ala Thr Ser Pro Thr Leu Thr Ala Arg Leu Val Ala Gln Ile
785                 790                 795                 800

His Asp Glu Leu Leu Phe Glu Val Glu Asp Thr Gln Val Pro Glu Phe
                805                 810                 815

Ala Ala Leu Val Arg Arg Ile Met Glu Ser Leu Gln Gln Val Gln Thr
                820                 825                 830

Leu Glu Leu Gln Leu Gln Val Pro Leu Lys Val Asn Leu Ser Val Gly
                835                 840                 845

Arg Ser Trp Gly His Leu Thr Pro Leu Gln Glu Ile Leu Gly Ser Ala
850                 855                 860
```

<210> SEQ ID NO 7
<211> LENGTH: 834
<212> TYPE: PRT
<213> ORGANISM: Thermus aquaticus

<400> SEQUENCE: 7

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
                100                 105                 110

Glu Val Pro Gly Tyr Glu Ala Asp Asp Val Leu Ala Thr Leu Ala Lys
                115                 120                 125

Lys Ala Glu Lys Glu Gly Tyr Glu Val Arg Ile Leu Thr Ala Asp Arg
        130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
                195                 200                 205
```

```
Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Arg Asp Val Ala Tyr Leu Gln Ala Leu Ser Leu Glu
    450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
```

```
625              630              635              640
His Thr Gln Thr Ala Ser Trp Met Phe Gly Val Pro Pro Glu Ala Val
                645              650              655
Asp Pro Leu Met Arg Arg Ala Ala Lys Thr Val Asn Phe Gly Val Leu
                660              665              670
Tyr Gly Met Ser Ala His Arg Leu Ser Gln Glu Leu Ala Ile Pro Tyr
                675              680              685
Glu Glu Ala Val Ala Phe Ile Glu Arg Tyr Phe Gln Ser Phe Pro Lys
                690              695              700
Val Arg Ala Trp Ile Glu Lys Thr Leu Glu Glu Gly Arg Lys Arg Gly
705              710              715              720
Tyr Val Glu Thr Leu Phe Gly Arg Arg Tyr Val Pro Asp Leu Asn
                725              730              735
Ala Arg Val Lys Ser Val Arg Glu Ala Ala Glu Arg Met Ala Phe Asn
                740              745              750
Met Pro Val Gln Gly Thr Ala Ala Asp Leu Met Lys Leu Ala Met Val
                755              760              765
Lys Leu Phe Pro Arg Leu Arg Glu Met Gly Ala Arg Met Leu Leu Gln
770              775              780
Val His Asp Glu Leu Leu Leu Glu Ala Pro Gln Ala Arg Ala Glu Glu
785              790              795              800
Val Ala Ala Leu Ala Lys Glu Ala Met Glu Lys Ala Tyr Pro Leu Ala
                805              810              815
Val Pro Leu Glu Val Glu Val Gly Met Gly Glu Asp Trp Leu Ser Ala
                820              825              830
Lys Gly

<210> SEQ ID NO 8
<211> LENGTH: 876
<212> TYPE: PRT
<213> ORGANISM: Geobacillus stearothermophilus

<400> SEQUENCE: 8

Met Lys Asn Lys Leu Val Leu Ile Asp Gly Asn Ser Val Ala Tyr Arg
1               5                   10                  15
Ala Phe Phe Ala Leu Pro Leu Leu His Asn Asp Lys Gly Ile His Thr
                20                  25                  30
Asn Ala Val Tyr Gly Phe Thr Met Met Leu Asn Lys Ile Leu Ala Glu
                35                  40                  45
Glu Gln Pro Thr His Ile Leu Val Ala Phe Asp Ala Gly Lys Thr Thr
                50                  55                  60
Phe Arg His Glu Thr Phe Gln Asp Tyr Lys Gly Gly Arg Gln Gln Thr
65              70                  75                  80
Pro Pro Glu Leu Ser Glu Gln Phe Pro Leu Leu Arg Glu Leu Leu Lys
                85                  90                  95
Ala Tyr Arg Ile Pro Ala Tyr Glu Leu Asp His Tyr Glu Ala Asp Asp
                100                 105                 110
Ile Ile Gly Thr Met Ala Ala Arg Ala Glu Arg Glu Gly Phe Ala Val
                115                 120                 125
Lys Val Ile Ser Gly Asp Arg Asp Leu Thr Gln Leu Ala Ser Pro Gln
                130                 135                 140
Val Thr Val Glu Ile Thr Lys Lys Gly Ile Thr Asp Ile Glu Ser Tyr
145             150                 155                 160
Thr Pro Glu Thr Val Val Glu Lys Tyr Gly Leu Thr Pro Glu Gln Ile
```

```
            165                 170                 175
Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Lys Gln Phe
            195                 200                 205

Gly Thr Val Glu Asn Val Leu Ala Ser Ile Asp Glu Ile Lys Gly Glu
            210                 215                 220

Lys Leu Lys Glu Asn Leu Arg Gln Tyr Arg Asp Leu Ala Leu Leu Ser
225                 230                 235                 240

Lys Gln Leu Ala Ala Ile Cys Arg Asp Ala Pro Val Glu Leu Thr Leu
                245                 250                 255

Asp Asp Ile Val Tyr Lys Gly Glu Asp Arg Glu Lys Val Val Ala Leu
                260                 265                 270

Phe Gln Glu Leu Gly Phe Gln Ser Phe Leu Asp Lys Met Ala Val Gln
            275                 280                 285

Thr Asp Glu Gly Glu Lys Pro Leu Ala Gly Met Asp Phe Ala Ile Ala
            290                 295                 300

Asp Ser Val Thr Asp Glu Met Leu Ala Asp Lys Ala Ala Leu Val Val
305                 310                 315                 320

Glu Val Val Gly Asp Asn Tyr His His Ala Pro Ile Val Gly Ile Ala
                325                 330                 335

Leu Ala Asn Glu Arg Gly Arg Phe Phe Leu Arg Pro Glu Thr Ala Leu
                340                 345                 350

Ala Asp Pro Lys Phe Leu Ala Trp Leu Gly Asp Glu Thr Lys Lys Lys
                355                 360                 365

Thr Met Phe Asp Ser Lys Arg Ala Ala Val Ala Leu Lys Trp Lys Gly
            370                 375                 380

Ile Glu Leu Arg Gly Val Val Phe Asp Leu Leu Leu Ala Ala Tyr Leu
385                 390                 395                 400

Leu Asp Pro Ala Gln Ala Ala Gly Asp Val Ala Ala Val Ala Lys Met
                405                 410                 415

His Gln Tyr Glu Ala Val Arg Ser Asp Glu Ala Val Tyr Gly Lys Gly
            420                 425                 430

Ala Lys Arg Thr Val Pro Asp Glu Pro Thr Leu Ala Glu His Leu Ala
            435                 440                 445

Arg Lys Ala Ala Ala Ile Trp Ala Leu Glu Glu Pro Leu Met Asp Glu
450                 455                 460

Leu Arg Arg Asn Glu Gln Asp Arg Leu Leu Thr Glu Leu Glu Gln Pro
465                 470                 475                 480

Leu Ala Gly Ile Leu Ala Asn Met Glu Phe Thr Gly Val Lys Val Asp
                485                 490                 495

Thr Lys Arg Leu Glu Gln Met Gly Ala Glu Leu Thr Glu Gln Leu Gln
            500                 505                 510

Ala Val Glu Arg Arg Ile Tyr Glu Leu Ala Gly Gln Glu Phe Asn Ile
            515                 520                 525

Asn Ser Pro Lys Gln Leu Gly Thr Val Leu Phe Asp Lys Leu Gln Leu
            530                 535                 540

Pro Val Leu Lys Lys Thr Lys Thr Gly Tyr Ser Thr Ser Ala Asp Val
545                 550                 555                 560

Leu Glu Lys Leu Ala Pro His Glu Ile Val Glu His Ile Leu His
                565                 570                 575

Tyr Arg Gln Leu Gly Lys Leu Gln Ser Thr Tyr Ile Glu Gly Leu Leu
            580                 585                 590
```

```
Lys Val Val His Pro Val Thr Gly Lys Val His Thr Met Phe Asn Gln
            595                 600                 605

Ala Leu Thr Gln Thr Gly Arg Leu Ser Ser Val Glu Pro Asn Leu Gln
        610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Glu Asp Asp Asn Leu Ile
            660                 665                 670

Glu Ala Phe Arg Arg Gly Leu Asp Ile His Thr Lys Thr Ala Met Asp
        675                 680                 685

Ile Phe His Val Ser Glu Glu Asp Val Thr Ala Asn Met Arg Arg Gln
        690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Asp Asn
            740                 745                 750

Ile Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Asn Val Arg
        770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ser Val Arg Leu Arg
                805                 810                 815

Glu Glu Arg Leu Gln Ala Arg Leu Leu Leu Gln Val His Asp Glu Leu
            820                 825                 830

Ile Leu Glu Ala Pro Lys Glu Glu Ile Glu Arg Leu Cys Arg Leu Val
        835                 840                 845

Pro Glu Val Met Glu Gln Ala Val Ala Leu Arg Val Pro Leu Lys Val
        850                 855                 860

Asp Tyr His Tyr Gly Pro Thr Trp Tyr Asp Ala Lys
865                 870                 875

<210> SEQ ID NO 9
<211> LENGTH: 605
<212> TYPE: PRT
<213> ORGANISM: Escherichia coli

<400> SEQUENCE: 9

Met Ile Ser Tyr Asp Asn Tyr Val Thr Ile Leu Asp Glu Glu Thr Leu
1               5                   10                  15

Lys Ala Trp Ile Ala Lys Leu Glu Lys Ala Pro Val Phe Ala Phe Ala
            20                  25                  30

Thr Ala Thr Asp Ser Leu Asp Asn Ile Ser Ala Asn Leu Val Gly Leu
        35                  40                  45

Ser Phe Ala Ile Glu Pro Gly Val Ala Ala Tyr Ile Pro Val Ala His
    50                  55                  60

Asp Tyr Leu Asp Ala Pro Asp Gln Ile Ser Arg Glu Arg Ala Leu Glu
65                  70                  75                  80

Leu Leu Lys Pro Leu Leu Glu Asp Glu Lys Ala Leu Lys Val Gly Gln
```

```
                85                  90                  95
Asn Leu Lys Tyr Asp Arg Gly Ile Leu Ala Asn Tyr Gly Ile Glu Leu
            100                 105                 110

Arg Gly Ile Ala Phe Asp Thr Met Leu Glu Ser Tyr Ile Leu Asn Ser
            115                 120                 125

Val Ala Gly Arg His Asp Met Asp Ser Leu Ala Glu Arg Trp Leu Lys
            130                 135                 140

His Lys Thr Ile Thr Phe Glu Glu Ile Ala Gly Lys Gly Lys Asn Gln
145                 150                 155                 160

Leu Thr Phe Asn Gln Ile Ala Leu Glu Ala Gly Arg Tyr Ala Ala
            165                 170                 175

Glu Asp Ala Asp Val Thr Leu Gln Leu His Leu Lys Met Trp Pro Asp
            180                 185                 190

Leu Gln Lys His Lys Gly Pro Leu Asn Val Phe Glu Asn Ile Glu Met
            195                 200                 205

Pro Leu Val Pro Val Leu Ser Arg Ile Glu Arg Asn Gly Val Lys Ile
            210                 215                 220

Asp Pro Lys Val Leu His Asn His Ser Glu Glu Leu Thr Leu Arg Leu
225                 230                 235                 240

Ala Glu Leu Glu Lys Lys Ala His Glu Ile Ala Gly Glu Glu Phe Asn
            245                 250                 255

Leu Ser Ser Thr Lys Gln Leu Gln Thr Ile Leu Phe Glu Lys Gln Gly
            260                 265                 270

Ile Lys Pro Leu Lys Lys Thr Pro Gly Gly Ala Pro Ser Thr Ser Glu
            275                 280                 285

Glu Val Leu Glu Glu Leu Ala Leu Asp Tyr Pro Leu Pro Lys Val Ile
            290                 295                 300

Leu Glu Tyr Arg Gly Leu Ala Lys Leu Lys Ser Thr Tyr Thr Asp Lys
305                 310                 315                 320

Leu Pro Leu Met Ile Asn Pro Lys Thr Gly Arg Val His Thr Ser Tyr
            325                 330                 335

His Gln Ala Val Thr Ala Thr Gly Arg Leu Ser Ser Thr Asp Pro Asn
            340                 345                 350

Leu Gln Asn Ile Pro Val Arg Asn Glu Glu Gly Arg Arg Ile Arg Gln
            355                 360                 365

Ala Phe Ile Ala Pro Glu Asp Tyr Val Ile Val Ser Ala Asp Tyr Ser
            370                 375                 380

Gln Ile Glu Leu Arg Ile Met Ala His Leu Ser Arg Asp Lys Gly Leu
385                 390                 395                 400

Leu Thr Ala Phe Ala Glu Gly Lys Asp Ile His Arg Ala Thr Ala Ala
            405                 410                 415

Glu Val Phe Gly Leu Pro Leu Glu Thr Val Thr Ser Glu Gln Arg Arg
            420                 425                 430

Ser Ala Lys Ala Ile Asn Phe Gly Leu Ile Tyr Gly Met Ser Ala Phe
            435                 440                 445

Gly Leu Ala Arg Gln Leu Asn Ile Pro Arg Lys Glu Ala Gln Lys Tyr
            450                 455                 460

Met Asp Leu Tyr Phe Glu Arg Tyr Pro Gly Val Leu Glu Tyr Met Glu
465                 470                 475                 480

Arg Thr Arg Ala Gln Ala Lys Glu Gln Gly Tyr Val Glu Thr Leu Asp
            485                 490                 495

Gly Arg Arg Leu Tyr Leu Pro Asp Ile Lys Ser Ser Asn Gly Ala Arg
            500                 505                 510
```

```
Arg Ala Ala Ala Glu Arg Ala Ala Ile Asn Ala Pro Met Gln Gly Thr
            515                 520                 525

Ala Ala Asp Ile Ile Lys Arg Ala Met Ile Ala Val Asp Ala Trp Leu
530                 535                 540

Gln Ala Glu Gln Pro Arg Val Arg Met Ile Met Gln Val His Asp Glu
545                 550                 555                 560

Leu Val Phe Glu Val His Lys Asp Asp Val Asp Ala Val Ala Lys Gln
                565                 570                 575

Ile His Gln Leu Met Glu Asn Cys Thr Arg Leu Asp Val Pro Leu Leu
            580                 585                 590

Val Glu Val Gly Ser Gly Glu Asn Trp Asp Gln Ala His
            595                 600                 605

<210> SEQ ID NO 10
<211> LENGTH: 928
<212> TYPE: PRT
<213> ORGANISM: Escherichia coli

<400> SEQUENCE: 10

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
                20                  25                  30

Gly Glu Pro Thr Gly Ala Met Tyr Gly Val Leu Asn Met Leu Arg Ser
            35                  40                  45

Leu Ile Met Gln Tyr Lys Pro Thr His Ala Ala Val Val Phe Asp Ala
50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175

Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
        195                 200                 205

Gly Gly Leu Asp Thr Leu Tyr Ala Glu Pro Glu Lys Ile Ala Gly Leu
210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

Glu Glu Leu Leu Gly Leu Phe Lys Lys Tyr Glu Phe Lys Arg Trp Thr
```

```
                275                 280                 285
Ala Asp Val Glu Ala Gly Lys Trp Leu Gln Ala Lys Gly Ala Lys Pro
290                 295                 300
Ala Ala Lys Pro Gln Glu Thr Ser Val Ala Asp Glu Ala Pro Glu Val
305                 310                 315                 320
Thr Ala Thr Val Ile Ser Tyr Asp Asn Tyr Val Thr Ile Leu Asp Glu
                325                 330                 335
Glu Thr Leu Lys Ala Trp Ile Ala Lys Leu Glu Lys Ala Pro Val Phe
                340                 345                 350
Ala Phe Asp Thr Glu Thr Asp Ser Leu Asp Asn Ile Ser Ala Asn Leu
                355                 360                 365
Val Gly Leu Ser Phe Ala Ile Glu Pro Gly Val Ala Ala Tyr Ile Pro
370                 375                 380
Val Ala His Asp Tyr Leu Asp Ala Pro Asp Gln Ile Ser Arg Glu Arg
385                 390                 395                 400
Ala Leu Glu Leu Leu Lys Pro Leu Leu Glu Asp Glu Lys Ala Leu Lys
                405                 410                 415
Val Gly Gln Asn Leu Lys Tyr Asp Arg Gly Ile Leu Ala Asn Tyr Gly
                420                 425                 430
Ile Glu Leu Arg Gly Ile Ala Phe Asp Thr Met Leu Glu Ser Tyr Ile
                435                 440                 445
Leu Asn Ser Val Ala Gly Arg His Asp Met Asp Ser Leu Ala Glu Arg
                450                 455                 460
Trp Leu Lys His Lys Thr Ile Thr Phe Glu Glu Ile Ala Gly Lys Gly
465                 470                 475                 480
Lys Asn Gln Leu Thr Phe Asn Gln Ile Ala Leu Glu Glu Ala Gly Arg
                485                 490                 495
Tyr Ala Ala Glu Asp Ala Asp Val Thr Leu Gln Leu His Leu Lys Met
                500                 505                 510
Trp Pro Asp Leu Gln Lys His Lys Gly Pro Leu Asn Val Phe Glu Asn
                515                 520                 525
Ile Glu Met Pro Leu Val Pro Val Leu Ser Arg Ile Glu Arg Asn Gly
                530                 535                 540
Val Lys Ile Asp Pro Lys Val Leu His Asn His Ser Glu Glu Leu Thr
545                 550                 555                 560
Leu Arg Leu Ala Glu Leu Glu Lys Lys Ala His Glu Ile Ala Gly Glu
                565                 570                 575
Glu Phe Asn Leu Ser Ser Thr Lys Gln Leu Gln Thr Ile Leu Phe Glu
                580                 585                 590
Lys Gln Gly Ile Lys Pro Leu Lys Lys Thr Pro Gly Gly Ala Pro Ser
                595                 600                 605
Thr Ser Glu Glu Val Leu Glu Glu Leu Ala Leu Asp Tyr Pro Leu Pro
                610                 615                 620
Lys Val Ile Leu Glu Tyr Arg Gly Leu Ala Lys Leu Lys Ser Thr Tyr
625                 630                 635                 640
Thr Asp Lys Leu Pro Leu Met Ile Asn Pro Lys Thr Gly Arg Val His
                645                 650                 655
Thr Ser Tyr His Gln Ala Val Thr Ala Thr Gly Arg Leu Ser Ser Thr
                660                 665                 670
Asp Pro Asn Leu Gln Asn Ile Pro Val Arg Asn Glu Glu Gly Arg Arg
                675                 680                 685
Ile Arg Gln Ala Phe Ile Ala Pro Glu Asp Tyr Val Ile Val Ser Ala
                690                 695                 700
```

-continued

```
Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
                725                 730                 735

Thr Ala Ala Glu Val Phe Gly Leu Pro Leu Glu Thr Val Thr Ser Glu
            740                 745                 750

Gln Arg Arg Ser Ala Lys Ala Ile Asn Phe Gly Leu Ile Tyr Gly Met
        755                 760                 765

Ser Ala Phe Gly Leu Ala Arg Gln Leu Asn Ile Pro Arg Lys Glu Ala
770                 775                 780

Gln Lys Tyr Met Asp Leu Tyr Phe Glu Arg Tyr Pro Gly Val Leu Glu
785                 790                 795                 800

Tyr Met Glu Arg Thr Arg Ala Gln Ala Lys Glu Gln Gly Tyr Val Glu
                805                 810                 815

Thr Leu Asp Gly Arg Arg Leu Tyr Leu Pro Asp Ile Lys Ser Ser Asn
            820                 825                 830

Gly Ala Arg Arg Ala Ala Ala Glu Arg Ala Ala Ile Asn Ala Pro Met
        835                 840                 845

Gln Gly Thr Ala Ala Asp Ile Ile Lys Arg Ala Met Ile Ala Val Asp
850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Asp Val Asp Ala Val
                885                 890                 895

Ala Lys Gln Ile His Gln Leu Met Glu Asn Cys Thr Arg Leu Asp Val
            900                 905                 910

Pro Leu Leu Val Glu Val Gly Ser Gly Glu Asn Trp Asp Gln Ala His
        915                 920                 925

<210> SEQ ID NO 11
<211> LENGTH: 17
<212> TYPE: PRT
<213> ORGANISM: artificial sequence
<220> FEATURE:
<223> OTHER INFORMATION: synthetic peptide

<400> SEQUENCE: 11

Leu Leu Val Ala Leu Asp Tyr Ser Gln Ile Glu Leu Arg Val Leu Ala
1               5                   10                  15

His

<210> SEQ ID NO 12
<211> LENGTH: 17
<212> TYPE: PRT
<213> ORGANISM: artificial sequence
<220> FEATURE:
<223> OTHER INFORMATION: synthetic peptide

<400> SEQUENCE: 12

Ser Ile Leu Ala Ala Asp Tyr Ser Gln Leu Glu Leu Arg Ile Leu Ala
1               5                   10                  15

His

<210> SEQ ID NO 13
<211> LENGTH: 14
<212> TYPE: DNA
<213> ORGANISM: artificial sequence
<220> FEATURE:
```

```
<223> OTHER INFORMATION: synthetic desoxynucleotide

<400> SEQUENCE: 13
tacgcattag cata                                                              14

<210> SEQ ID NO 14
<211> LENGTH: 15
<212> TYPE: RNA
<213> ORGANISM: artificial sequence
<220> FEATURE:
<223> OTHER INFORMATION: synthetic oligoribonucleotide

<400> SEQUENCE: 14
uacgcauuag caaug                                                             15

<210> SEQ ID NO 15
<211> LENGTH: 15
<212> TYPE: RNA
<213> ORGANISM: artificial sequence
<220> FEATURE:
<223> OTHER INFORMATION: synthetic oligoribonucleotide

<400> SEQUENCE: 15
uuaugcuaau guccc                                                             15

<210> SEQ ID NO 16
<211> LENGTH: 35
<212> TYPE: DNA
<213> ORGANISM: artificial sequence
<220> FEATURE:
<223> OTHER INFORMATION: synthetic oligonucleotide

<400> SEQUENCE: 16
tgactactct cagcttggac tgaggatctt ggctc                                       35

<210> SEQ ID NO 17
<211> LENGTH: 35
<212> TYPE: DNA
<213> ORGANISM: artificial sequence
<220> FEATURE:
<223> OTHER INFORMATION: synthetic oligonucleotide

<400> SEQUENCE: 17
gagccaagat cctcagtcca agctgagagt agtca                                       35

<210> SEQ ID NO 18
<211> LENGTH: 38
<212> TYPE: DNA
<213> ORGANISM: artificial sequence
<220> FEATURE:
<223> OTHER INFORMATION: synthetic oligonucleotide

<400> SEQUENCE: 18
catgcctttg tgcctttcgt aggtggttca atactggc                                    38

<210> SEQ ID NO 19
<211> LENGTH: 38
<212> TYPE: DNA
<213> ORGANISM: artificial sequence
<220> FEATURE:
<223> OTHER INFORMATION: synthetic oligonucleotide

<400> SEQUENCE: 19
gccagtattg aaccacctac gaaaggcaca aaggcatg                                    38
```

```
<210> SEQ ID NO 20
<211> LENGTH: 39
<212> TYPE: DNA
<213> ORGANISM: artificial sequence
<220> FEATURE:
<223> OTHER INFORMATION: synthetic oligonucleotide

<400> SEQUENCE: 20
gcagcaggca aaacagattt gctttgggat catttatgg                    39

<210> SEQ ID NO 21
<211> LENGTH: 39
<212> TYPE: DNA
<213> ORGANISM: artificial sequence
<220> FEATURE:
<223> OTHER INFORMATION: synthetic oligonucleotide

<400> SEQUENCE: 21
ccataaatga tcccaaagca aatctgtttt gcctgctgc                    39

<210> SEQ ID NO 22
<211> LENGTH: 43
<212> TYPE: DNA
<213> ORGANISM: artificial sequence
<220> FEATURE:
<223> OTHER INFORMATION: synthetic oligoonucleotide

<400> SEQUENCE: 22
ggctgctgac tactctcaga tgggactgag gatcttggct cat               43

<210> SEQ ID NO 23
<211> LENGTH: 43
<212> TYPE: DNA
<213> ORGANISM: artificial sequence
<220> FEATURE:
<223> OTHER INFORMATION: synthetic oligonucleotide

<400> SEQUENCE: 23
atgagccaag atcctcagtc ccatctgaga gtagtcagca gcc               43

<210> SEQ ID NO 24
<211> LENGTH: 35
<212> TYPE: DNA
<213> ORGANISM: artificial sequence
<220> FEATURE:
<223> OTHER INFORMATION: synthetic oligonucleotide

<400> SEQUENCE: 24
aggtggttca atactggttg ctgactactc tcacg                        35

<210> SEQ ID NO 25
<211> LENGTH: 35
<212> TYPE: DNA
<213> ORGANISM: artificial sequence
<220> FEATURE:
<223> OTHER INFORMATION: synthetic oligonucleotide

<400> SEQUENCE: 25
gctgagagta gtcagcaacc agtattgaac cacct                        35

<210> SEQ ID NO 26
<211> LENGTH: 15
<212> TYPE: RNA
<213> ORGANISM: artificial sequence
<220> FEATURE:
<223> OTHER INFORMATION: synthetic oligonucleotide
```

```
<400> SEQUENCE: 26
gggacauuag cauaa                                                              15
```

DNA POLYMERASE THETA MUTANTS, METHODS OF PRODUCING THESE MUTANTS, AND THEIR USES

BACKGROUND OF THE INVENTION

In the field of therapeutic biotechnologies, nucleic acids have proved to be a useful tool for the regulation of gene expression, medical diagnostics, biological route modulation, molecular recognition strategies or drug design. Key strategies have been developed and have proved their efficiency for several years such as antisense nucleic acids[1,2], ribozymes and riboswitches[3,4] and aptamers[5,6]. However, some innovative breakthrough in the generation of aptamer-based molecules remains needed to compete with medicinal chemistry and/or biological antibodies.

Nucleic acid aptamers consist of single-stranded DNA (ssDNA) or RNA that present defined 3D structures due to their propensity to form complementary base pairs. Their ability to fold into various secondary and tertiary structures' opens the possibility to design different conformations that are capable of specific molecular recognition of their cognate targets. RNA aptamers are prone to generate more complex 3D structures than DNA aptamers and usually display a higher binding affinity and specificity[6]. Triple base-pairs, hydrophobic and electrostatic interactions, van der Waals forces, shape complementarity and base stacking all combine to generate folded structures and shielded active sites that determine their binding affinity and specificity. For all of these purposes, aptamers are listed among the most important classes of drug molecules and their development is facilitated by Systematic Evolution of Ligands by EXponential enrichment (SELEX) strategies[8,9]. This efficient method of producing high-affinity of aptamers relies on the generation of a combinatorial library of oligonucleotides (around $10^{15}$). These libraries must contain a huge pool of random-sequence oligonucleotides to maximize the chances to select good candidates. As an alternative to the chemical synthesis of random oligonucleotides at the first step of aptamer selection, the engineering of DNA polymerases designed to synthesize nucleic acids (RNA and DNA) in a random fashion may become the cutting edge of SELEX.

In vivo, DNA polymerases are crucial to the DNA replication and the maintenance of the genome and therefore their role is critical for the propagation of the genetic information. All DNA polymerases found in eukaryotes, prokaryotes, archaea and viruses have been classified into subfamilies according to their structure and primary sequence similarity[10,11]. By their inherent role, replicative DNA polymerases copy the template DNA with high fidelity and consequently their native activity is of limited use for applications in modern synthetic biology, which seeks to build novel and versatile nucleic acid polymers. Indeed, DNA polymerases have an active site that is configured to incorporate the four canonical deoxyribonucleotides and to exclude 'altered' or modified nucleotides during cellular metabolism.

Representative members of family A with a known crystal structure are E. coli DNA Pol I[11] and T. aquaticus DNA pol I[12] in prokaryotes, and phage T7[13] DNA pol in viruses; in eukaryotes, Pol theta (Pol θ) takes part in the repair of DNA double-strand-breaks (DSB) in the so-called Non-Homologous End Joining (NHEJ) process)[14–16], pol nu (pol v) in the repair of DNA crosslinks occurring during homologous recombination (HR) and Pol gamma (Pol γ) is involved in mitochondrial DNA replication[17]. Very recently, human Pol theta has been described to display a robust terminal transferase activity that is apparent when it switches between three different mechanisms during alternative end-joining (alt-EJ)[18,19]. Indeed, human Pol theta is able to perform non-templated DNA extension, as well as instructed replication that is templated in cis or in trans of the DSB. The same study revealed that the non-templated transferase activity is enhanced in the presence of manganese divalent ions and can be randomly combined with templated extension on the 3'-end of a nucleic acid primer.

The other family of DNA polymerases which has some significant nucleotidyltransferase activity is the pol X family, especially in eukaryotes (Pol beta (Pol β), Pol lambda (Pol γ), Pol mu (Pol μ), and TdT)[20,21]. This activity is usually enhanced in the presence of transition metal ions. Among them, TdT (Terminal deoxynucleotidyl Transferase) is described to catalyze non-templated, random nucleotide addition at the V(D)J junctions to increase the antigen receptor diversity[18,22,23]. On top of this property, previous studies revealed that TdT indiscriminately incorporates ribonucleotides (NTPs) and deoxyribonucleotides (dNTPs)[24,25] but then fails to extend it beyond 4-5 nucleotides because the primer is no longer a DNA but an RNA. This observation is compatible with the known crystal structure of murine TdT where none of the protein residues seemed to act as steric barrier close to the 2' or the 3' position of the ddATP sugar[25]. However, engineering TdT to make it accept an RNA primer seems quite a challenge, given the conformation of the primer in the structure of the tertiary complex, where the conformation of the primer strand is a B-DNA, contrary to what would be expected for an RNA primer (A-DNA).

NTPs differ from dNTPs only by the presence of an additional hydroxyl group in the 2'-position of the ribose. It was shown that human Pol theta incorporated the NTPs better than TdT[18] and enabled the synthesis of long polymers of RNAs, although with low yields. The joint predisposition of such DNA polymerases (Pol theta and TdT), to i) perform random nucleotides incorporation in a template-free manner and ii) the possibility to tolerate both NTPs and dNTPs and other modified nucleotides, opens the way to create a novel nucleic acid synthetic machine. This suggests that random RNA library could be enzymatically generated much easier without the need of the reverse-transcription step of DNA fragments during SELEX.

There is a need in the art for some DNA Polymerase theta mutants capable of incorporating a large diversity of nucleic analogs and generating long polymers of, nucleic acids analogs, capable of increasing the sampling as well as improving the stability, the affinity and the specificity of functional nucleic acids such as RNA aptamers.

BRIEF SUMMARY OF THE INVENTION

The invention relates to mutant DNA polymerases of the Pol theta subfamily capable of performing non-templated nucleic acid extension, or of a functional fragment of such a polymerase, methods of producing these mutant DNA polymerases, and uses and methods of using these mutant DNA polymerases.

In various embodiments, the mutant DNA polymerase theta (Pol theta) or a functional fragment thereof comprises at least one amino acid substitution at a position selected from the group consisting of: 2322, 2328, 2334, 2335, 2384, 2387 and 2391, the indicated positions being determined by alignment with SEQ ID NO: 1. In various embodiments, the mutant DNA polymerase theta (Pol theta) or a functional fragment thereof comprises at least one amino acid substitution selected from the group consisting of: a Proline (P) to an aliphatic amino acid or a polar amino acid substitution at position 2322, an Alanine (A) to an aliphatic amino acid or a polar amino acid substitution at position 2328, a Leucine (L) to an aliphatic amino acid substitution at position 2334, a Glutamic acid (E) to an aliphatic amino acid or a polar amino acid substitution at position 2335, a Glutamine (Q) to an aliphatic amino acid or a polar amino acid substitution at position 2384, a Tyrosine (Y) to an aromatic amino acid or an aliphatic amino acid substitution at position 2387, and a Tyrosine (Y) to an aromatic amino acid or an aliphatic amino acid substitution at position 2391, the indicated positions being determined by alignment with SEQ ID NO: 1.

In various embodiments, the mutant DNA polymerase theta (Pol theta) or a functional fragment thereof comprises at least one amino acid substitution at position 2322, wherein the amino acid at position 2322 is substituted by an aliphatic amino acid selected from the group consisting of: Valine (V) and Alanine (A), the indicated position being determined by alignment with SEQ ID NO: 1.

In various embodiments, the mutant DNA polymerase theta (Pol theta) or a functional fragment thereof comprises at least one amino acid substitution at position 2322, wherein the amino acid at position 2322 is substituted by a polar amino acid selected from the group consisting of: Threonine (T) and Serine (S), the indicated position being determined by alignment with SEQ ID NO: 1.

In various embodiments, the mutant DNA polymerase theta (Pol theta) or a functional fragment thereof comprises at least one amino acid substitution at position 2328, wherein the amino acid at position 2328 is substituted by an aliphatic amino acid selected from the group consisting of: Valine (V) and Glycine (G), the indicated position being determined by alignment with SEQ ID NO: 1.

In various embodiments, the mutant DNA polymerase theta (Pol theta) or a functional fragment thereof comprises at least one amino acid substitution at position 2328, wherein the amino acid at position 2328 is substituted by a polar amino acid selected from the group consisting of: Threonine (T) and Serine (S), the indicated position being determined by alignment with SEQ ID NO: 1.

In various embodiments, the mutant DNA polymerase theta (Pol theta) or a functional fragment thereof comprises at least one amino acid substitution at position 2334, wherein the amino acid at position 2334 is substituted by an aliphatic amino acid selected from the group consisting of: Methionine (M), Isoleucine (I) and Alanine (A), the indicated position being determined by alignment with SEQ ID NO: 1.

In various embodiments, the mutant DNA polymerase theta (Pol theta) or a functional fragment thereof comprises at least one amino acid substitution at position 2335, wherein the amino acid at position 2335 is substituted by an aliphatic amino acid selected from the group consisting of: Glycine (G) and Alanine (A), the indicated position being determined by alignment with SEQ ID NO: 1.

In various embodiments, the mutant DNA polymerase theta (Pol theta) or a functional fragment thereof comprises at least one amino acid substitution at position 2335, wherein the amino acid at position 2335 is substituted by a polar amino acid selected from the group consisting of: Threonine (T) and Serine (S), the indicated position being determined by alignment with SEQ ID NO: 1.

In various embodiments, the mutant DNA polymerase theta (Pol theta) or a functional fragment thereof comprises at least one amino acid substitution at position 2384, wherein the amino acid at position 2384 is substituted by an Alanine (A), the indicated position being determined by alignment with SEQ ID NO: 1.

In various embodiments, the mutant DNA polymerase theta (Pol theta) or a functional fragment thereof comprises at least one amino acid substitution at position 2384, wherein the amino acid at position 2384 is substituted by a polar amino acid selected from the group consisting of: Asparagine (N), Serine (S) and Threonine (T), the indicated position being determined by alignment with SEQ ID NO: 1

In various embodiments, the mutant DNA polymerase theta (Pol theta) or a functional fragment thereof comprises at least one amino acid substitution at position 2387, wherein the amino acid at position 2387 is substituted by an aromatic amino acid selected from the group consisting of: Phenylalanine (F) and Tryptophan (W), the indicated position being determined by alignment with SEQ ID NO: 1.

In various embodiments, the mutant DNA polymerase theta (Pol theta) or a functional fragment thereof comprises at least one amino acid substitution at position 2387, wherein the amino acid at position 2387 is substituted by an aliphatic amino acid selected from the group consisting of: Alanine (A) and Valine (V), the indicated position being determined by alignment with SEQ ID NO: 1.

In various embodiments, the mutant DNA polymerase theta (Pol theta) or a functional fragment thereof comprises at least one amino acid substitution at position 2391, wherein the amino acid at position 2391 is substituted by an aromatic amino acid selected from the group consisting of: Phenylalanine (F) and Tryptophan (W), the indicated position being determined by alignment with SEQ ID NO: 1.

In various embodiments, the mutant DNA polymerase theta (Pol theta) or a functional fragment thereof comprises at least one amino acid substitution at position 2391, wherein the amino acid at position 2391 is substituted by an aliphatic amino acid selected from the group consisting of: Alanine (A) and Valine (V), the indicated position being determined by alignment with SEQ ID NO: 1.

In various embodiments, the mutant DNA polymerase theta (Pol theta) or a functional fragment thereof comprises at least one amino acid substitution selected from the group consisting of: P to V substitution at position 2322 (P2322V), A to V substitution at position 2328 (A2328V), L to M substitution at position 2334 (L2334M), E to G substitution at position 2335 (E2335G), Q to N at position 2384 (Q2384N), Y to F substitution at position 2387 (Y2387F); and Y to F substitution at position 2391 (Y2391 F), the indicated positions being determined by alignment with SEQ ID NO: 1.

In various embodiments, the mutant DNA polymerase theta (Pol theta) or a functional fragment thereof comprises at least one amino acid substitution selected from the group consisting of: P to V substitution at position 2322 (P2322V), A to V substitution at position 2328 (A2328V), L to M substitution at position 2334 (L2334M), E to G substitution at position 2335 (E2335G), and Y to F substitution at position 2387 (Y2387F), the indicated positions being determined by alignment with SEQ ID NO: 1.

In various embodiments, the mutant DNA polymerase theta (Pol theta) or a functional fragment thereof comprises at least two amino acid substitutions at positions 2334 and 2335, the indicated position being determined by alignment with SEQ ID NO: 1. In various embodiments, the amino acid at position 2334 is substituted by an amino acid selected from the group consisting of: Methionine (M), Isoleucine (I) and Alanine (A), and preferably by a Methionine (M). In some embodiments, the amino acid at position 2335 is substituted by an amino acid selected from the group consisting of: Glycine (G), Alanine (A), Threonine (T) and Serine (S), and preferably by a Glycine (G).

In various embodiments, the mutant DNA polymerase theta (Pol theta) or a functional fragment thereof comprises a double amino acid substitution L2334M and E2335G, the indicated positions being determined by alignment with SEQ ID NO: 1.

In various embodiments, the invention encompasses nucleic acids comprising a nucleotide sequence encoding the mutant DNA polymerase or a functional fragment thereof, a DNA vector comprising these nucleic acids, and a host cell comprising these vectors.

In various embodiments, the invention encompasses a method for generating a mutant DNA polymerase of the Pol theta subfamily or a functional fragment thereof, comprising substituting at least one amino acid in a DNA polymerase of the Pol theta subfamily at a position selected from the group consisting of: 2322, 2328, 2334, 2335, 2384, 2387 and 2391, the indicated positions being determined by alignment with SEQ ID NO: 1.

In various embodiments, the invention encompasses the use of the nucleic acids, vectors, and host cells of the invention for producing a mutant DNA polymerase or a functional fragment thereof.

In various embodiments, the invention encompasses a method for producing a mutant DNA polymerase culturing the host cell of the invention under culture conditions allowing expression of the polynucleotide encoding said mutant, and optionally recovering said mutant thus expressed from the medium culture or host cells.

In one embodiment, the invention encompasses a method for incorporating nucleotides in a template-free manner comprising incubating the mutant DNA polymerase of the invention or a functional fragment thereof with nucleotide triphosphates under conditions that allow nucleotide incorporation in the absence of a template.

In one embodiment, the invention encompasses the use the mutant DNA polymerase of the invention or a functional fragment thereof, for incorporating nucleotides in a template-free manner.

In various embodiments, the invention encompasses a method for producing degenerate or random nucleotide sequences comprising incubating the mutant DNA polymerase of the invention or a functional fragment thereof with nucleotide triphosphates under conditions that allow degenerate or random nucleotide incorporation to produce degenerate or random nucleotide sequences. In some embodiments, a fixed nucleotide sequence can be added to the 3' end of the degenerate or random nucleotide sequences. In some embodiments, the degenerate or random nucleotide sequences can be amplified. In some embodiments, the amplified sequences can be cloned into a vector to generate a library of degenerate or random nucleotide sequences.

In one embodiment, the invention encompasses use the mutant DNA polymerase of the invention or a functional fragment thereof for generating an aptamer library.

In various embodiments, the invention encompasses a kit for generating an aptamer library comprising the mutant DNA polymerase of the invention or a functional fragment thereof. In some embodiments, the kit comprises reagents for degenerate or random nucleotide incorporation. In some embodiments, the kit comprises a vector for generating a library of degenerate or random nucleotide sequences.

BRIEF DESCRIPTION OF THE DRAWINGS

FIG. 1A-B. Sequence alignment of the Finger subdomain (residues 2333-2474) of Pol theta (Pol θ) and the related A family polymerases.

(a) Strictly conserved residues are highlighted and the conserved motifs are boxed rectangle. Stars indicate the strictly conserved catalytic aspartate (D2330 and D2540) and glutamate (E2541) of the palm subdomain that coordinate divalent cation in human pol theta (pol θ) (Zahn et al. 2015). Triangles indicate the conserved residues that were mutated in this study and those that are potentially mutable to confer nucleotidyltransferase activity to the human pol theta (pol θ). Secondary structures based on the PDB id. (4X0P) of the human pol theta (pol θ) are depicted on the top of the multiple alignment. Human pol theta (UniProtKB/Swiss-Prot accession number O75417.2; SEQ ID NO: 1); Mouse pol theta (UniProtKB/Swiss-Prot accession number Q8CGS6.2; SEQ ID NO: 2); Zebrafish pol theta (NCBI accession number XP_021329106.1; SEQ ID NO: 3); Fruit fly mus308 pol theta 'UniProtKB/Swiss-Prot: O18475.1; SEQ ID NO: 4); Human pol nu (UniProtKB/Swiss-Prot accession number Q7Z5Q5.2; SEQ ID NO: 5); Mouse pol nu (UniProtKB/Swiss-Prot accession number Q7TQ07.2; SEQ ID NO: 6); Taq pol I (GenBank accession number BAA06033.1; SEQ ID NO: 7); Geobacillus stearothermophilus DNA pol I (GenBank: AAC37139.1; SEQ ID NO: 8); E. coli DNA pol Klenow fragment (PDB accession number 1D8Y_A; SEQ ID NO: 9); E. coli DNA pol (UniProtKB/Swiss-Prot accession number P00582.1; SEQ ID NO: 10).

(b) Sequence comparison of the motif A of Taq pol I and human pol theta (pol θ), the immutable residue D610 is mentioned while the residues that tolerate a wide spectrum of substitution are displayed according to the nature of amino acid that they accept. Taq pol I motif A (LLVALDYSQIELRVLAH; SEQ ID NO: 11). Human pol theta motif A (SILAADYSQLELRILAH; SEQ ID NO: 12).

FIG. 2A-C. Structure of human pol theta (pol θ) polymerase domain (residues 1792-2590).

(a) Surface representation of human pol theta (pol θ) (PDB 4X0P) showing the folding pattern of a right hand with the three subdomains: the fingers, the palm and the thumb. A DNA primer is inserted between the palm and the fingers and where it will be elongated in the catalytic site. The N-terminal exo-like domain is also displayed.

(b) Superposition of Taq pol I (1QSY) and human pol theta (polθ) (4X0P) where both enzymes are shown in stick models. A zoom-in stereo view of the fingers subdomain displays the residues E615 (1QSY) compared to E2335 (4X0P) in the closed proximity of the incoming nucleotide (ddATP) facing the DNA primers (for 4X0P and for 1QSY).

(c) Ribbon diagram of the ddATP-$Ca^{2+}$ structure of the finger subdomain around the catalytic site. The strictly conserved carboxylates (D2330, D2540 and E2541) coordinating metal cations, the mutable residues (L2334, E2335, Q2384, Y2387 and Y2391) are displayed as sticks. The incoming ddATP is showed in ball-and-stick models and the ssDNA primer (3'-end) is showed.

Figure 3:
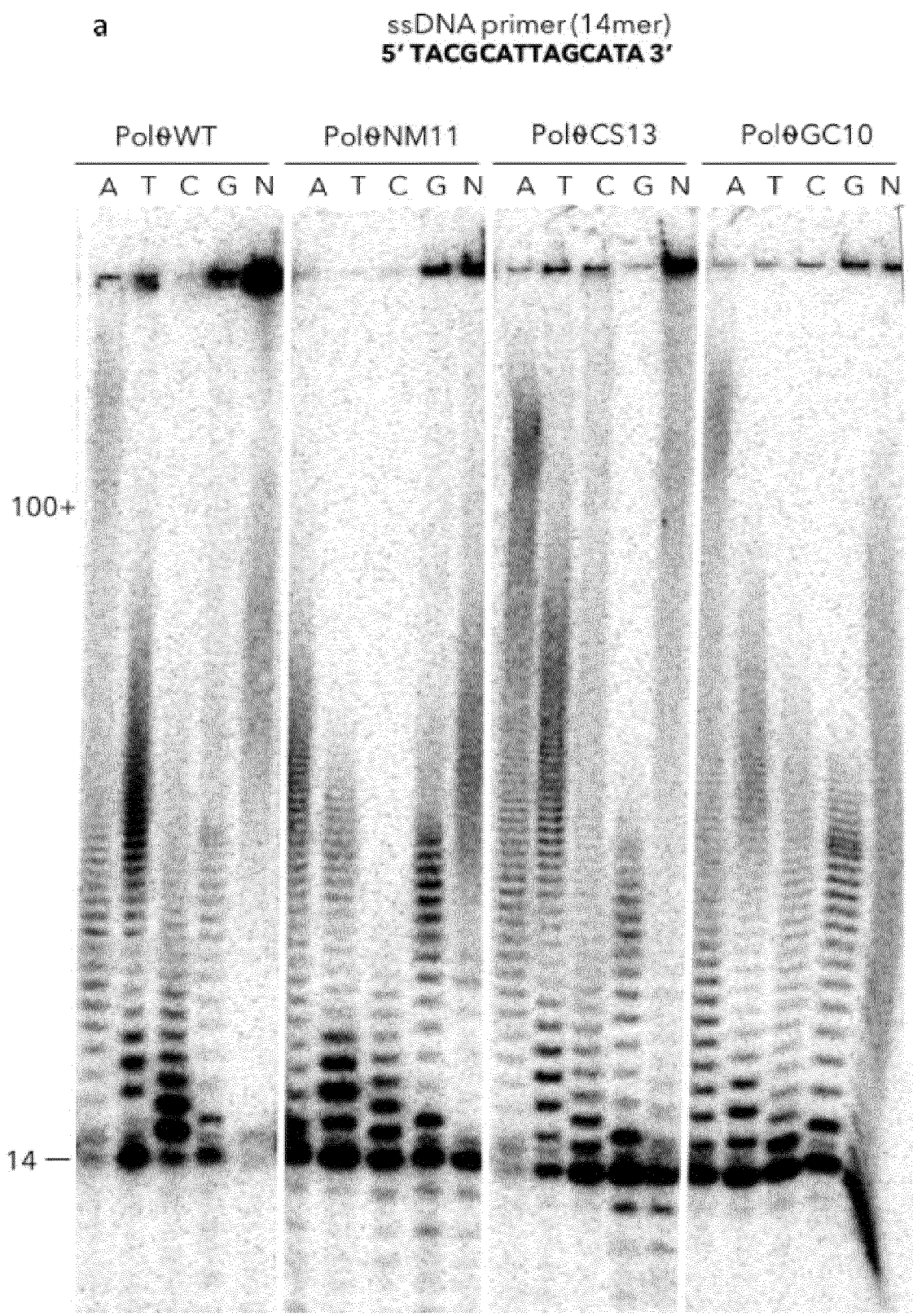

FIG. 3. Deoxynucleotidyltransferase activity of human pol theta (pol θ) WT and its respective mutants. Denaturing gel showing pol θ variants presence of $Mn^{2+}$ cations and each of the four dNTPs (A, T, C, G) and the mix (N). A 14-mer ssDNA (5'TACGCATTAGCATA; SEQ ID NO: 13) serves as a primer being extended and forming long homo- or heteropolymers that reach up to 150-200 nt. The primer extension of three mutants (NM11, CS13 and GC10) are also displayed in the same conditions as the pol theta (pol θ) WT. Reactions were stopped after 30 min of incubation.

FIG. 4A-D. Ribonucleotidyltransferase activity of human pol theta (pol θ) WT and its respective mutants.

(a) and (c) Denaturing gel showing pol θ variants presence of $Mn^{2+}$ cations and each of the four NTPs (A, U, C, G at 0.5 mM each) and the mix (N, at 0.5 mM each). A 14-mer ssDNA (5'TACGCATTAGCATA; SEQ ID NO: 13) serves as a primer being extended and forming long homo- or heteropolymers that reach up to 150-200 nt. The primer extension of four mutants: NM11, CS13, GC10 and DW9 (a) or five mutants: NM11, CS13, GC10, DW9 and MC15 (c) are also displayed in the same conditions as the pol θ WT. Reactions were stopped after 30 min of incubation.

(b) and (d) Time-course of a 14-mer ssDNA primer (5'TACGCATTAGCATA; SEQ ID NO: 13) by CS13 mutant in the presence of a stoichiometric mix of the four NTPs (0.5 mM each). At each indicated time: 0 s to 30 min (b) or 0 s to 60 min (d), the reaction was stopped by the addition of formamide blue.

FIG. 5A-C. Ribbon representations of the nucleotide binding pocket of the human pol theta (pol θ) polymerase domain (4X0P).

(a) ddATP-$Ca^{2+}$-pol theta (pol θ) WT structure showing the position of E2335 towards the incoming nucleotide.

(b) Theoretical model of ATP-$Mn^{2+}$-pol theta (pol θ) WT structure depicting the steric hindrance between E2335 residue and the sugar moiety of the nucleotide.

(c) Theoretical model of ATP-$Mn^{2+}$-pol theta (polθ) E2335G structure showing the spacing of the nucleotide binding pocket when the glutamate residue is substituted by a glycine residue.

FIG. 6A-J. HPLC fragmentation of the ribonucleosides obtained after enzymatic hydrolysis of synthetic RNAs.

(a) and (f) Chromatogram of the standards solutions of the four ribonucleosides (adenosine, guanosine, uridine and cytidine at concentrations of 0.1 mM (a) or 0.25 mM (f) in digestion buffer), the retention times and the base corresponding to each peak are displayed on top of each peak.

(b) and (i) RNA hydrolysate obtained from an equimolar mix of ATP and CTP.

(c) and (j) RNA hydrolysate obtained from an equimolar mix of GTP and UTP.

(d) and (g) RNA hydrolysate obtained from an equimolar mix of the four NTPs.

(e) and (h) RNA hydrolysate obtained from a mix containing ATP/CTP/GTP/UTP at a molar ratio of 1:1:1:10.

FIG. 7A-D. TruSeq statistical analysis 1: Occurrences of the reads in each synthesis condition illustrated by a log-log scatter plot chart.

(a) Condition 'N', mix of four nucleotides at a ratio of 1:1:1:1 (500 μM each).

(b) Condition '10U' with 500 μM of ATP, CTP and GTP, and 5 mM of UTP (ratio of 1:1:1:10).

(c) Condition '5U5C' with 500 μM of ATP and GTP and 2.5 mM of CTP and UTP (ratio of 1:1:5:5).

(d) Condition '5U' with 500 μM of ATP, CTP and GTP and 2.5 mM of UTP (ratio of 1:1:1:5).

FIG. 8A-D. TruSeq statistical analysis 2: Nucleotide frequency per read represented by a box plot chart.

(a) Condition 'N', mix of four nucleotides at a ratio of 1:1:1:1 (500 μM each).

(b) Condition '10U' with 500 μM of ATP, CTP and GTP, and 5 mM of UTP (ratio of 1:1:1:10).

(c) Condition '5U5C' with 500 μM of ATP and GTP and 2.5 mM of CTP and UTP (ratio of 1:1:5:5).

(d) Condition '5U' with 500 μM of ATP, CTP and GTP and 2.5 mM of UTP (ratio of 1:1:1:5).

FIG. 9A-D. TruSeq statistical analysis 3: Nucleotide proportion per incorporation cycle illustrated by a stacked bars chart.

(a) Condition 'N', mix of four nucleotides at a ratio of 1:1:1:1 (500 μM each).

(b) Condition '10U' with 500 μM of ATP, CTP and GTP, and 5 mM of UTP (ratio of 1:1:1:10).

(c) Condition '5U5C' with 500 μM of ATP and GTP and 2.5 mM of CTP and UTP (ratio of 1:1:5:5).

(d) Condition '5U' with 500 μM of ATP, CTP and GTP and 2.5 mM of UTP (ratio of 1:1:1:5).

FIG. 10A-D. TruSeq statistical analysis 4: Nucleotide transition matrix illustrating the proportion of A/C/G/U added after a given nucleotide, horizontal stacked bars chart.

(a) Condition 'N', mix of four nucleotides at a ratio of 1:1:1:1 (500 μM each).

(b) Condition '10U' with 500 μM of ATP, CTP and GTP, and 5 mM of UTP (ratio of 1:1:1:10).

(c) Condition '5U5C' with 500 μM of ATP and GTP and 2.5 mM of CTP and UTP (ratio of 1:1:5:5).

(d) Condition '5U' with 500 μM of ATP, CTP and GTP and 2.5 mM of UTP (ratio of 1:1:1:5).

Figure 11:
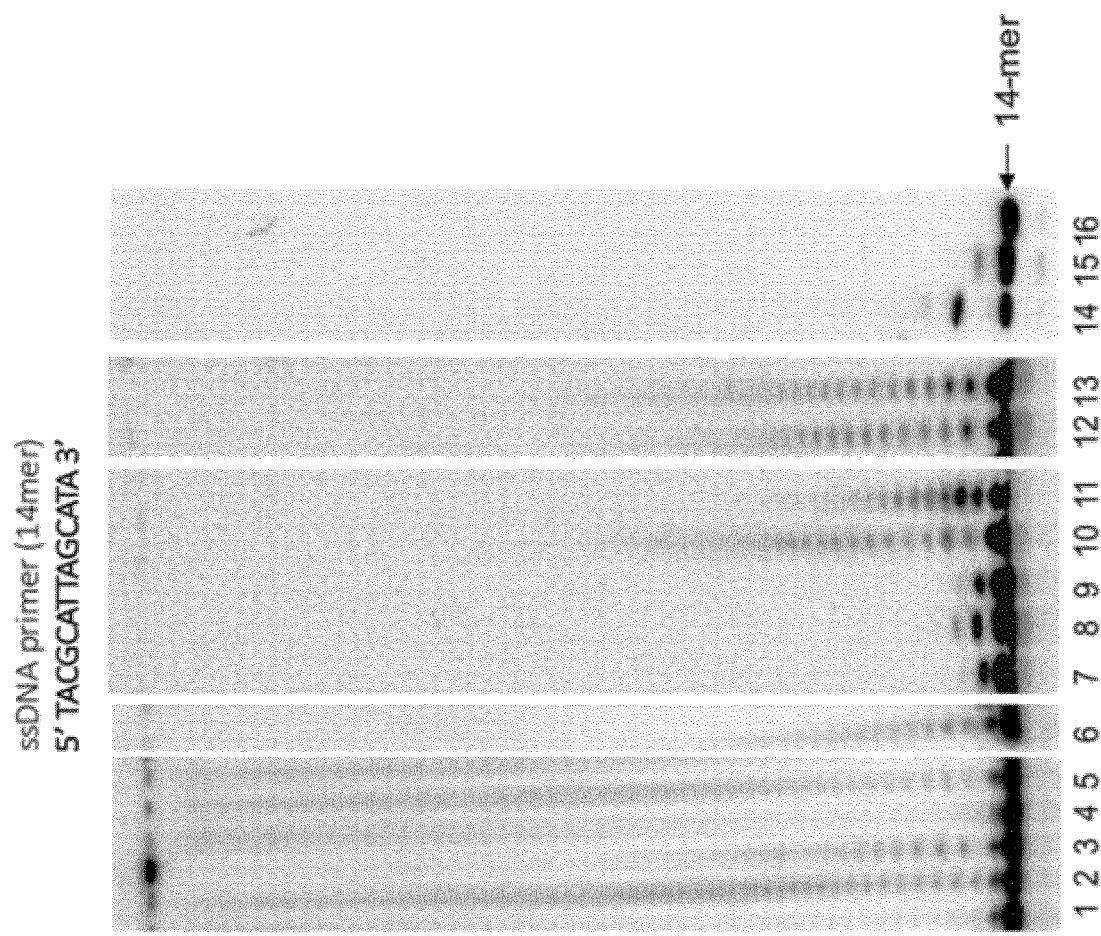

FIG. 11. Incorporation of modified nucleotides by pol theta (pol θ) CS13. The following analogs were successfully accepted and can be decomposed in two classes; those that made polymers: (1) 2'-Fluoro-dUTP, (2) 2'-Fluoro-dATP, (3) 2'-Fluoro-dCTP, (4) 2'-Fluoro-dGTP, (5) 2'-Fluoro-dTTP, (6) 2'-Amino-dATP, (7) 5-methyl-UTP, (8) Ara-ATP (Vidarabine triphosphate), (9) Ara-CTP (Cytarabine triphosphate), (10) 2'-O-methyl-ATP, (11) 2'-O-methyl-CTP, (12) epsilon (ε)-ATP, (13) 2-Aminopurine, (14) FANA, (15) 5EUTP, (16) Control without NTP; and those that stopped after one incorporation (because of the lack of a 3'OH and/or the presence of a modified or blocked 3' group): (17) O—CH3-ddTTP, (18) 2'-Amino-dTTP, (19) 3'-Amino-ddGTP, (20) N3-ddGTP, (21) N3-ddTTP, (22) 3'-deoxy-ATP, (23) 3'-deoxy-UTP, (24) 3'-deoxy-CTP, (25) 3'-deoxy-GTP, (26) 3'-deoxy-NTP. The reactions were performed in the same conditions as with the natural NTPs in presence of $Mn^{2+}$ using a 14-mer ssDNA primer (5'TACGCATTAGCATA; SEQ ID NO: 13).

Figure 12:
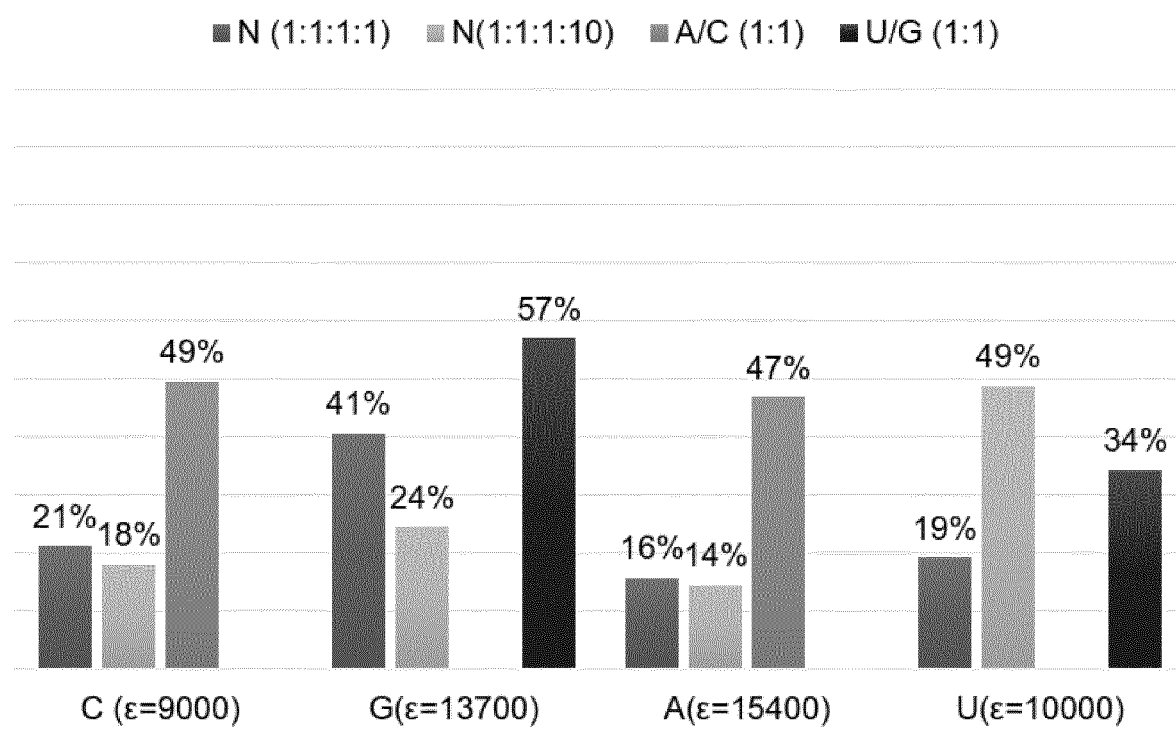

FIG. 12. Distribution of the ribonucleoside as function of the composition of ribonucleotide substrate added to CS13 mutant.

Figure 13:
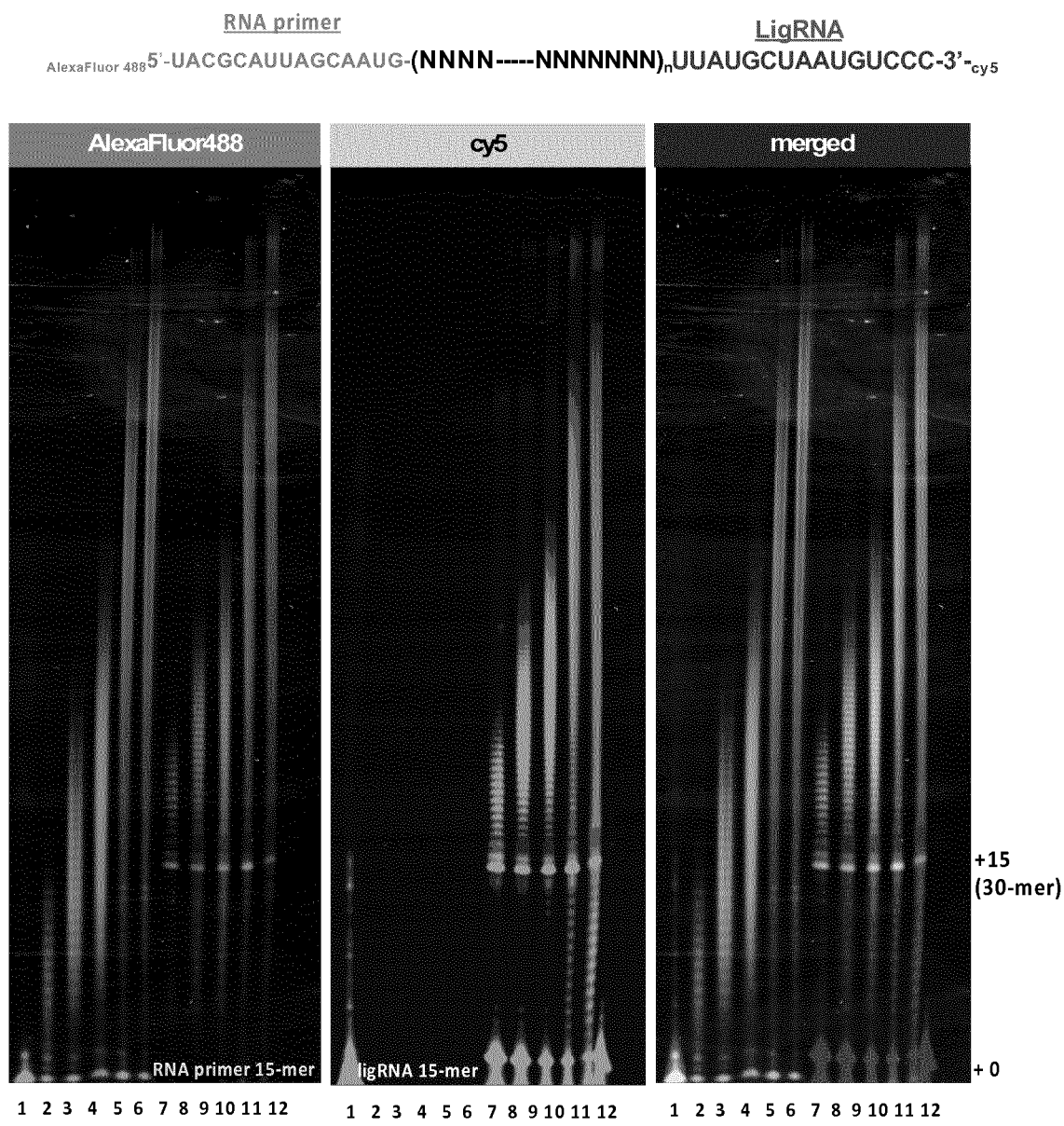

FIG. 13. Ligation of a constant region to the 3'-end of the RNA pool synthesized by pol θ-DW9 mutant and by using T4 RNA ligase. Time-course of the elongation of a 15-mer ssRNA primer by DW9 mutant in the presence of a stoichiometric mix of the four NTPs (0.5 mM each) and separated in a denaturing 8% acrylamide gel. At each indicated time (5 s, 30 s, 1 min, 5 min and 15 min), the reaction was stopped by the addition of formamide blue. (1) Control: RNA primer+ligRNA without enzyme. (2) Elongation control after 5 sec. (3) Elongation control after 30 sec. (4) Elongation control after 1 min. (5) Elongation control after 5 min. (6) Elongation control after 15 min. (7) Ligation after 5 sec-elongation (+15). (8) Ligation after 30 secDoubli-elongation (+15). (9). Ligation after 1 min-elongation (+15). (10). Ligation after 5 minDoubli-elongation (+15). (11). Ligation after 15 minDoubli-elongation (+15). (12) Autoligation control.

(AlexaFluor488) The fluorescence signal displays the presence and the elongation of all the RNA fragments containing the 5'Alexa-fluor-labelled RNA primer (AlexaFluor488-UACGCAUUAGCAAUG; SEQ ID NO: 14).

(CY5) The fluorescence signal displays the fragments that have been ligated with the constant region (oligonucleotide ligRNA-Cy5 5'P-UUAUGCUAAUGUCCC-3'-CY5; SEQ ID NO: 15) at 3'-end by T4 RNA ligase.

(Merged) The Alexa fluor and CY5 signals have been merged to better evaluate the quality of the reactions (elongation+ligation).

Figure 14:
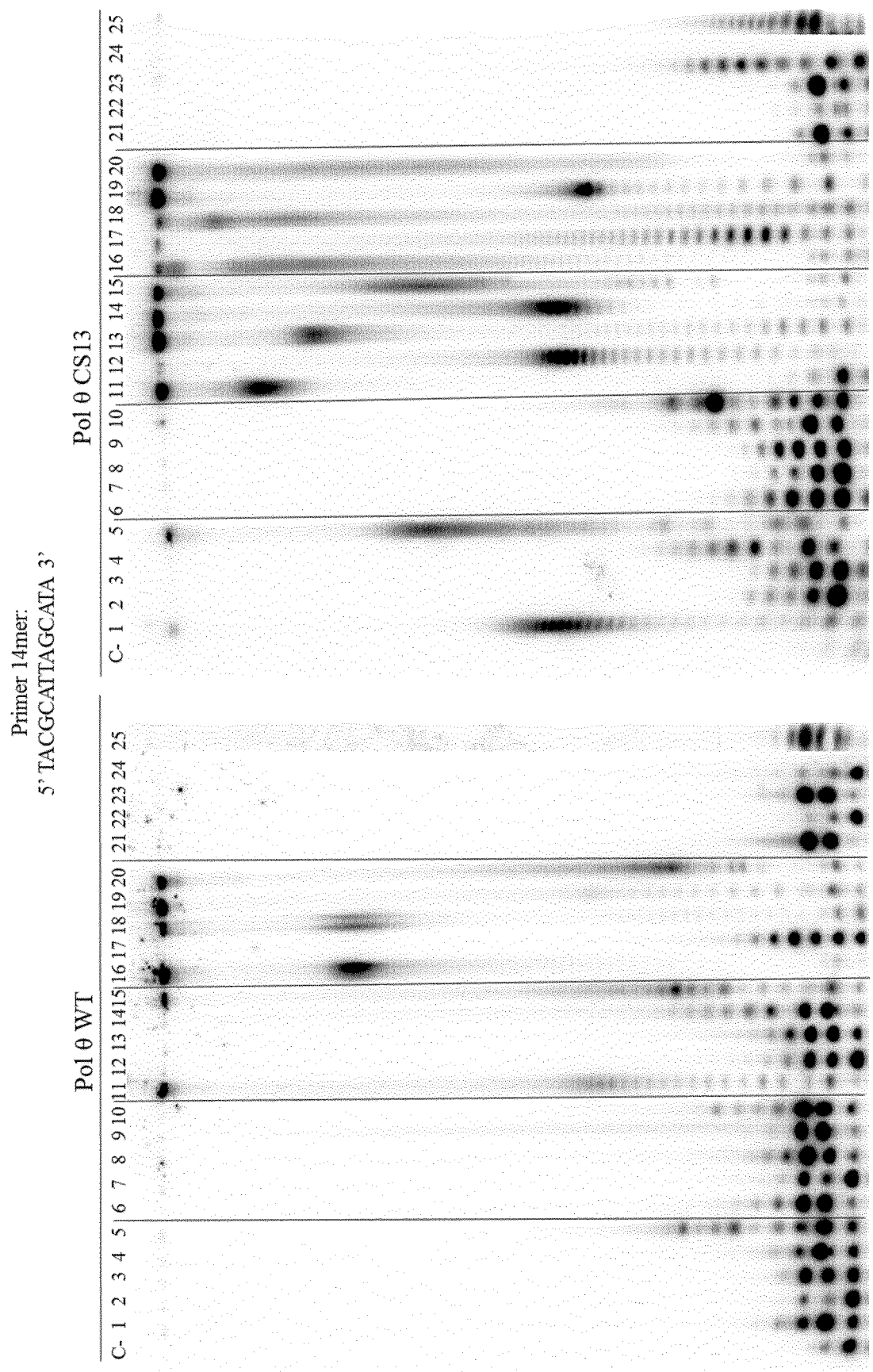

FIG. 14. Incorporation of modified nucleotides by pol theta (pol θ) WT in comparison with the pol θ CS13. The following analogs were tested for the elongation of the ssDNA primer (5'TACGCATTAGCATA; SEQ ID NO: 13) by pol θ CS13 compared to pol θ. (1) 2'-Amino-dATP, (2) 2'-Amino-dUTP, (3) 2'-Amino-dCTP, (4) 2'-Amino-dGTP, (5) mix of 2'-Amino-dATP/dUTP/dCTP/dGTP, (6) 2'-O-methyl-dATP, (7) 2'-O-methyl-dUTP, (8) 2'-O-methyl-dCTP, (9) 2'-O-methyl-dGTP, (10) mix of 2'-O-methyl-dATP/dUTP/dCTP/dGTP, (11) 2'-azido-2'-dATP (12) 2'-azido-2'-dUTP, (13) 2'-azido-2'-dCTP, (14) 2'-azido-2'-dGTP, (15) mix of 2'-azido-2'-dATP/dUTP/dCTP/dGTP, (16) 2'-fluoro-dATP, (17) 2'-Fluoro-dUTP (18) 2'-fluoro-dCTP, (19) 2'-Fluoro-dGTP, (20) 2'-fluoro-dTTP, (21) mix of 2'-fluoro-dATP/dUTP/dCTP/dGTP (22) Ara-ATP (Vidarabine triphosphate), (23) Ara-CTP (Cytarabine triphosphate), (24) mix of Ara-ATP and Ara-CTP (25) epsilon(ε)-ATP (26) 2-Aminopurine riboside triphosphate. The reactions were performed in the same conditions as with the natural NTPs in presence of $Mn^{2+}$.

Figure 15:
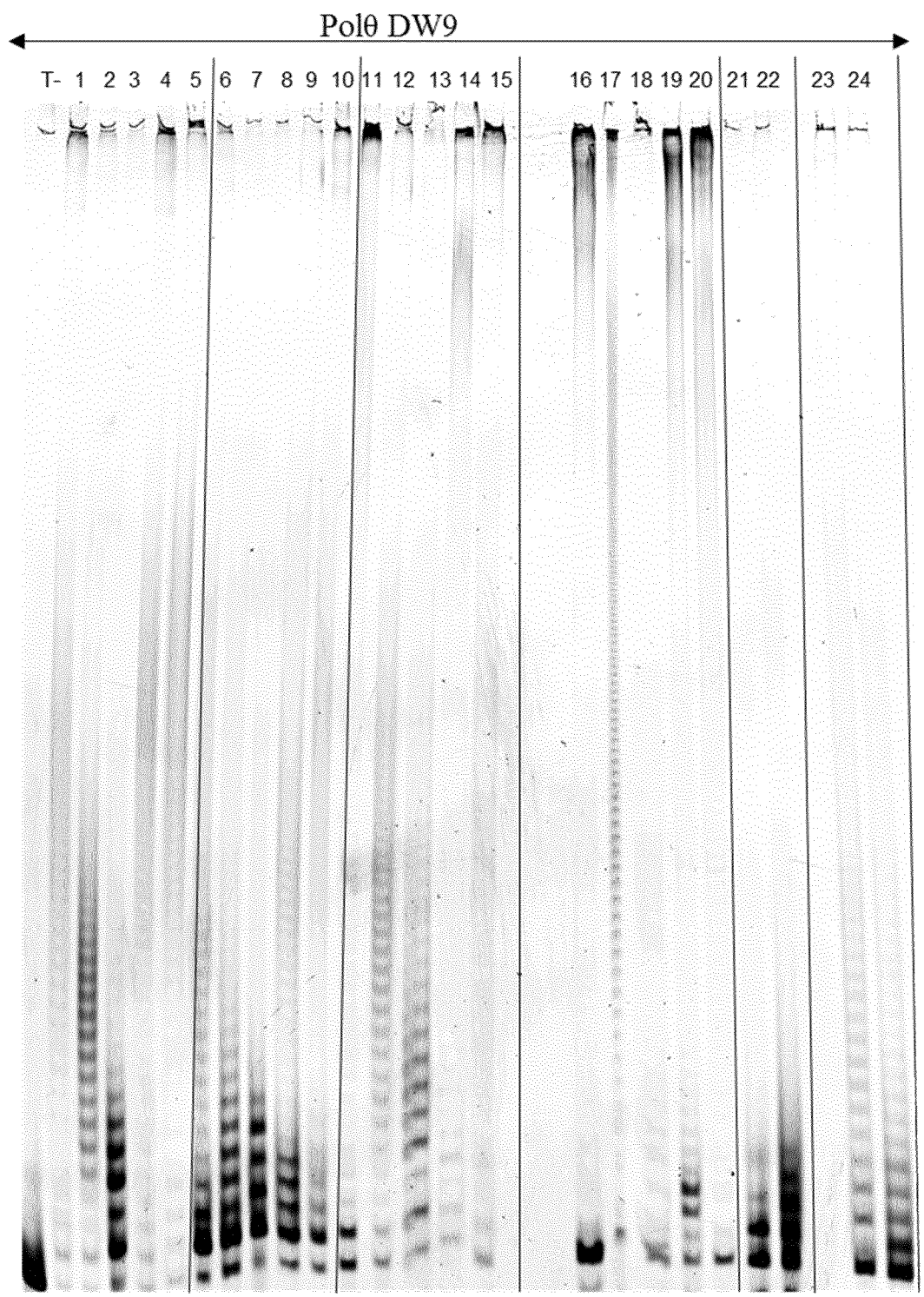

FIG. 15. Incorporation of modified nucleotides by pol θ DW9. The following analogs were tested for the elongation of the ssDNA primer (5'TACGCATTAGCATA; SEQ ID NO: 13) by pol θ DW9 compared to pol θ. (1) 2'-Amino-dATP, (2) 2'-Amino-dUTP, (3) 2'-Amino-dCTP, (4) 2'-Amino-dGTP, (5) mix of 2'-Amino-dATP/dUTP/dCTP/dGTP, (6) 2'-O-methyl-dATP, (7) 2'-O-methyl-dUTP, (8) 2'-O-methyl-dCTP, (9) 2'-O-methyl-dGTP, (10) mix of 2'-O-methyl-dATP/dUTP/dCTP/dGTP, (11) 2'-azido-2'-dATP (12) 2'-azido-2'-dUTP, (13) 2'-azido-2'-dCTP, (14) 2'-azido-2'-dGTP, (15) mix of 2'-azido-2'-dATP/dUTP/dCTP/dGTP, (16) 2'-fluoro-dATP, (17) 2'-Fluoro-dUTP (18) 2'-fluoro-dCTP, (19) 2'-Fluoro-dGTP, (20) 2'-fluoro-dTTP, (21) Ara-ATP (Vidarabine triphosphate), (22) Ara-CTP (Cytarabine triphosphate), (23) epsilon(ε)-ATP (24) 2,6-diaminopurine riboside triphosphate. The reactions were performed in the same conditions as with the natural NTPs in presence of $Mn^{2+}$.

DETAILED DESCRIPTION OF THE INVENTION

The application relates to the subject-matter as defined in the claims as filed and as herein described. In the application, unless specified otherwise or unless a context dictates otherwise, all the terms have their ordinary meaning in the relevant field(s).

Functional nucleic acids, in particular nucleic acid aptamers, can exhibit valuable advantages and properties compared to protein therapeutics in terms of size, synthetic accessibility, affinity and specificity. As these molecules can be selected from pools of random-sequence oligonucleotides, the engineering of DNA or RNA polymerases remains the basis of the successful enzymatic synthesis of functional nucleic acids analogs.

The present invention provides A-family DNA polymerase mutants that can efficiently incorporate natural or modified nucleotides, particularly, ribonucleotides at the 3' end of a nucleic acid, resulting in long polymers that could serve as a library for the selection of functional nucleic acids, in particular aptamers or ribozymes. Five mutants of DNA polymerase (named CS13, DW9, MC15, NM11 and GC10) were generated and the mutations were focused on the residues located in close proximity of the catalytic site.

The functional characterization of each mutant has been performed and two promising candidates (CS13 and DW9) were able to display an enhanced efficiency to incorporate the four natural ribonucleotides (ATP, UTP, CTP and GTP) compared to the wild-type.

As a result, long homo- or heteropolymers of ribonucleotides were obtained whose length is highly variable (20-300 nt) and can be controlled by the time-length of the reaction, which necessitate $Mn^{2+}$ ions. HPLC analysis of the resulting ribonucleosides obtained after enzymatic digestion of the newly synthesized RNA also showed the equal probability of incorporation of the four ribonucleotides and the randomness of the sequences was confirmed after RNA-sequencing. Moreover, the incorporation of modified deoxy- and ribonucleotides has been also investigated. The following analogs were successfully accepted by at least one promising mutant: 2'-Fluoro-dNTP (2'-Fluoro-dATP, 2'-Fluoro-dUTP, 2'-Fluoro-dCTP, 2'-Fluoro-dGTP, 2'-Fluoro-dTTP, and mixtures thereof); 2'-Amino-dNTP (2'-Amino-dATP, 2'-Amino-dUTP, 2'-Amino-dTTP; 2'-Amino-dCTP, 2'-Amino-dGTP, and mixtures thereof); 2'-O-methyl-dNTP (2'-O-methyl-dATP, 2'-O-methyl-dUTP, 2'-O-methyl-dCTP, 2'-O-methyl-dGTP, and mixtures thereof), 2'-$N_3$-dNTP (2'-azido-2'-dATP, 2'-azido-2'-dUTP, 2'-azido-2'-dCTP, 2'-azido-2'-dGTP, and mixtures thereof); O—CH3-ddTTP, 3'-Amino-ddGTP, N3-ddGTP, N3-ddTTP, Ara-ATP (Vidarabine triphosphate), Ara-CTP (Cytarabine triphosphate), 2'-O-methyl-ATP, 2'-O-methyl-CTP, 3'-deoxy-ATP, 3'-deoxy-UTP, 3'-deoxy-CTP, 3'-deoxy-GTP, 3'-deoxy-NTP, epsilon(ε)-ATP, 2-Aminopurine riboside triphosphate, FANA (9-(2'-Fluoro-2'-deoxy-β-D-arabinofuranosyl) adenine), 5-ethynyl-UTP, and 5-methyl-UTP. These properties of DNA polymerase will contribute to broaden the applicability of chemically modified nucleic acids in RNA biology, medical diagnosis, and molecular recognition strategies. By this work, a versatile toolbox for RNA and DNA functionalization and for aptamer design may come into being.

Pol Theta Mutants With New Properties

Figure 1A:
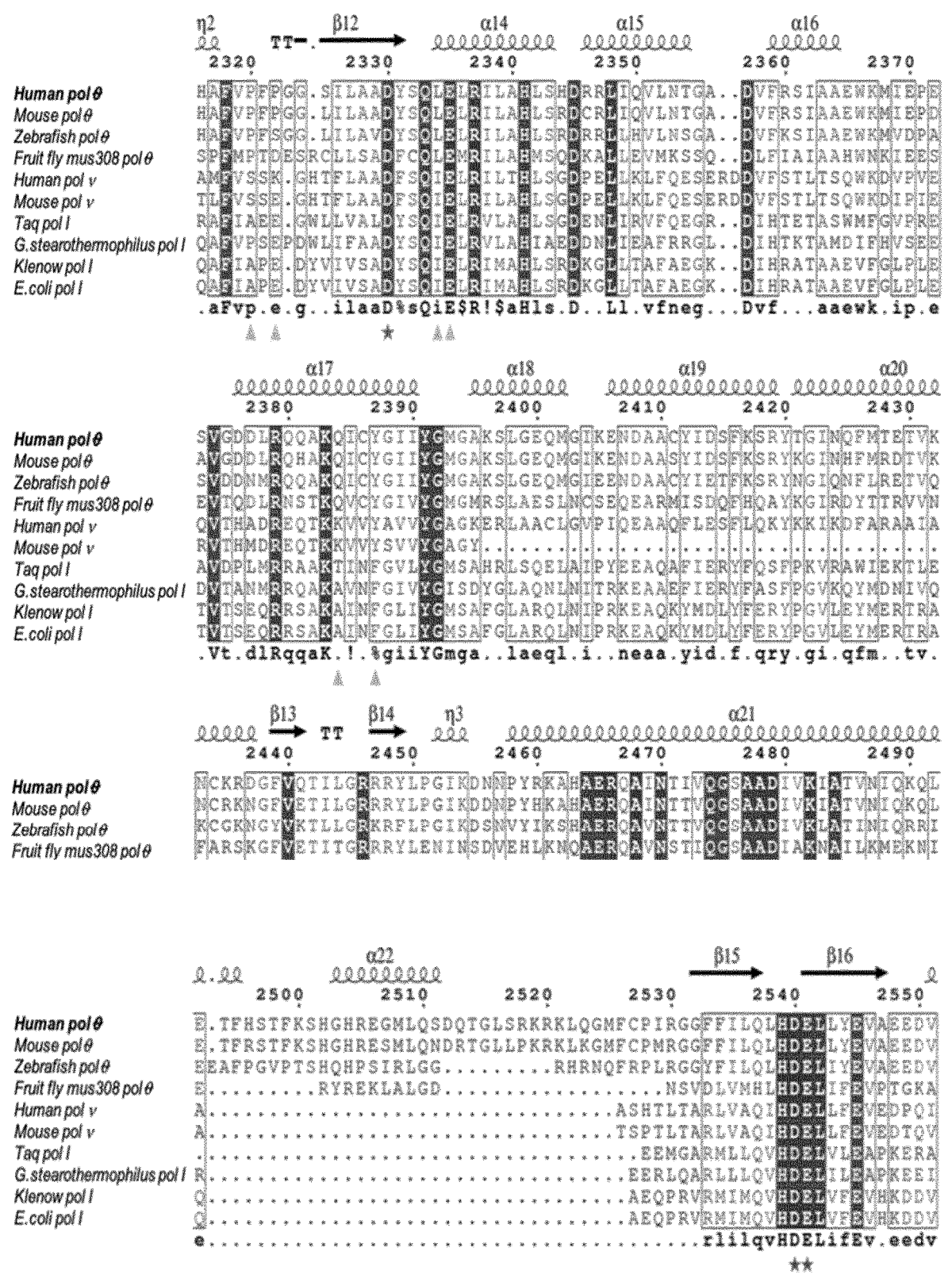
Figure 1B:
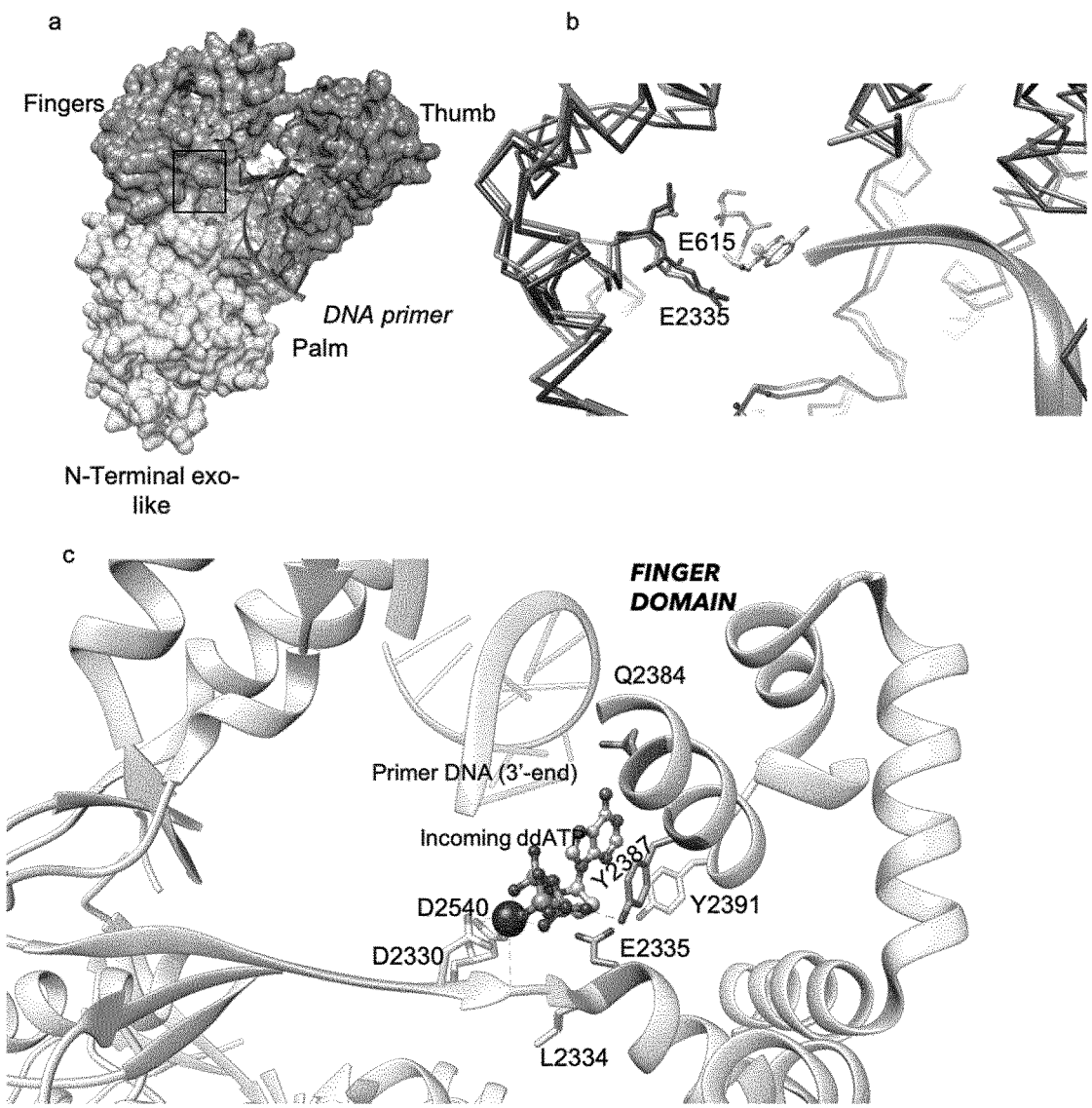

DNA polymerases contain an active site with highly conserved motifs that are structurally superimposable within each family. Several studies showed that most DNA polymerases share two conserved regions, motifs A and C, that are located in the palm subdomain[28]. Motif A contains a strictly conserved aspartate at the junction of a beta(β)-strand and alpha(α)-helix, while motif C contains two carboxylate residues (Asp or Glu) at a beta-turn-beta structural motif[10]. In the case of human pol theta (pol θ) the strictly catalytic conserved aspartate (D2330) is located between beta12 (β12) and alpha9 (α9) and is part of a strictly conserved motif (DYSQLELR) in the different pol theta (pol θ) (FIG. 1a). This catalytic aspartate corresponds to D610 in Taq DNA polymerase I which interacts with the incoming dNTP and stabilizes the transition state that leads to phosphodiester bond formation[29]. This sequence motif (DYSQLELR) is exceptionally well conserved in A-family polymerases and within the Pol I family[13] as described in the FIG. 1 for pol theta (pol θ), pol nu (pol v) and bacterial pol I. Previous studies showed that mutation of the catalytic aspartate (D610) completely altered the polymerase activity and was immutable while systematic mutations of the other 13 residues (605 to 617) including the most conserved region (DYSQLELR) of the motif A of Taq DNA pol I showed that some positions tolerated a wide spectrum of substitutions (L605, L606, V607, A608, L609, S612, I614, R617). Otherwise, the remaining residues tolerated mainly conservative substitutions (Y611, Q613, E615 and L617). The residue S612 was highly mutable and accepted substitutions that are diverse in size, and hydrophobicity while keeping WT-like activity[28]. Alignment of human pol theta (pol θ) and Taq pol 1 sequences (FIG. 1b) illustrates the conservation of the DYSQLELR and displays the main residues corresponding to pol theta (pol θ) sequence (D610 corresponds to D2330, D615 to D2335). The same authors described that the residues Y611, Q613, E615 and L617 were involved in dNTP binding, and especially E615 that forms a hydrogen bond with Y671 (a residue located in helix O within the finger motif and stacks with the base moiety of the incoming dNTPs). The inventors follow this line of reasoning for human pol theta (pol θ) with the aim of widening its substrate specificity to accept natural and modified NTPs. Indeed, good candidates for site-directed mutations are L2334, E2335, A2328 within the motif A and also residue Y2387 in motif B (corresponding to Y671 in Taq pol I).

The crystal structure of the polymerase domain of pol theta (pol θ) (residues 1792-2590; PDB 4X0P)[15,26] reveals the same right hand-like topology seen in the bacterial and phage homologs. The surface representation of pol theta (pol θ) (FIG. 2a) illustrates the three subdomains (fingers, palm and thumb) and a N-terminal exonuclease subdomain. The DNA strand slides into the catalytic site between the fingers and the palm where the motif A residues make the junction between the two parts. When pol theta (pol θ) is superimposed with Taq pol I (1QSY) (FIG. 2b), both structures displayed a closed overall conformation. The residues E615 (1QSY) and E2335 (4X0P) are oriented in similar manner towards the incoming nucleotide and can interact with the sugar moiety of the nucleotide. Taq pol I has been extensively studied and diversified to increase its ability to incorporate NTPs and modified nucleotides[30]. Taq pol I libraries were generated by diversifying the residues 611-617 that include the nucleotide binding pocket and the steric gate residue E615. Among the different Taq pol I mutants, I614K and a multiple-site mutant SFR3 (A597T, W604R, L605Q, I614K, E615G) showed the ability to incorporate NTPs after short-patch compartimentalized self-replication (spCSR) selection[30] while no detectable primer extension by wt-Taq pol I was observed. However, the best mutant was able to incorporate up to 6 NTPs in the presence of $Mg^{2+}$ and up to 14 NTPs when $Mn^{2+}$ is used instead of $Mg^{++}$.

In light of the close similarity of the described region of Taq pol I and human pol theta (pol θ) (FIG. 1b), the inventors focused on the corresponding steric gate residue E2335 and the immediately close residue L2334. The inventors then also analyzed the residues located in the proximal region of the nucleotide binding pocket (P2322, A2328, Q2384, Y2387 and Y2391). The ribbon representation of human pol theta (pol θ) (FIG. 2c) depicts the spatial organization of the catalytic site with the strictly conserved carboxylates (D2330, D2540 and E2541) that chelate the metal ion. In the immediate proximity of the catalytic triad the residues E2335 is facing the incoming nucleotide where its carboxylate group is susceptible to interact with the C2' of the ribose of the nucleotide (ddATP) and to form also a hydrogen bond with the residue Y2387 and/or Y2391. The role of E2335 as a steric gate may lie in the fact that a steric constrain would exist if the C2' of the ribose holds a hydroxyl group (FIG. 5). In addition, the polar property of E2335 may play a role in the formation of a salt bridge. Otherwise, the residue Y2387 has been described to interact with the beta (β)-phosphate of the incoming nucleotide[15] and the aromatic cycle is stacked alongside to the nucleotide base.

NTPs Incorporation of the Designed Mutants: the Pivotal Role of the Steric Gate Residue Human pol theta (pol θ) WT has been already described to have the ability to incorporate NTPs[18] in a template-free manner from the 3'-end of a ssDNA or ssRNA primer, albeit with a low yield. However, it is already apparent that human pol theta (pol θ) shows an enhanced nucleotidyltransferase activity compared to Terminal deoxynucleotidyltranferase (TdT) in presence of NTPs, which stopped the elongation after 5-6 additions.

With the aim of selecting the best human pol theta (pol θ) mutant with an enhanced incorporation of NTPs, the inventors proceeded to evaluate the ability to elongate a ssDNA primer through a nucleotidyltransferase assay. One or two-site directed mutagenesis were performed and led to generate the following mutants: NM11 (Y2387F), CS13 (E2335G), GC10 (P2322V), DW9 (L2334M-E2335G) and MC15 (A2328V).

Bacteria containing these mutants was deposited at the Collection Nationale de Cultures de Microorganismes (CNCM) at the Institut Pasteur, 25, Rue du Docteur Roux, 75724 Paris, FR, on Sep. 14, 2017, under the deposit numbers CNCM I-5238 (E. coli Δ1-1791_CS13); CNCM I-5239 (E. coli Δ1-1791_DW9); CNCM I-5240 (E. coli Δ1-1791_MC15); and CNCM I-5241 (E. coli Δ1-1791_NM11).

Figure 4C:
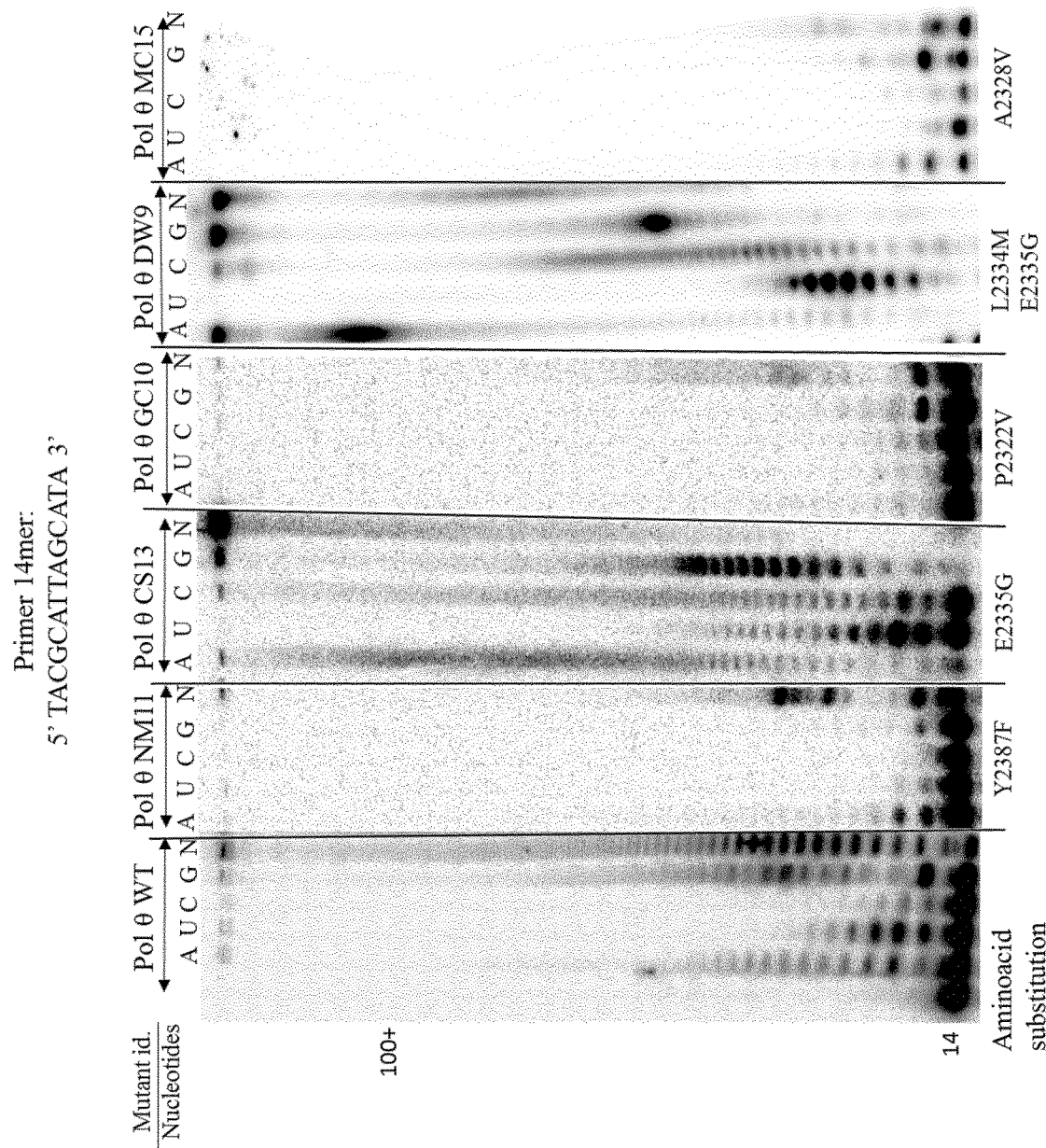

The wt-like activity was first tested with dNTPs (FIG. 3) and all the mutants tested retained the native activity as they incorporated the four natural dNTPs and generated fragments of length of up to 200 nt like the pol theta (pol θ) WT in the presence of 5 mM of $Mn^{2+}$. When dNTPs were replaced by each NTP (ATP, UTP, CTP, GTP) the pol theta (pol θ) WT showed similar results as previously described[18]. ATP and GTP (purine bases) are well tolerated by pol θ WT and medium-length homopolymers of A and G (up to 50-70 nt) were obtained. UTP and CTP were incorporated but the elongation stopped after a few additions. The mutants NM11 and GC10 were unable to incorporate more than 3 or 4 NTPs. Surprisingly, the mutant CS13 was particularly efficient as more than 50 of each ribonucleotide were readily incorporated, except for UTP that formed homopolymers of U whose length reached only up to 15 nt, still longer than the pol θ WT would add. Furthermore, when the four NTPs were mixed together the elongation was clearly enhanced compared to the wild-type enzyme, in that 100% of the primer were extended and the synthesized heteropolymers reached more than 200 nt in 30 min (FIGS. 4a and 4c). Mutants DW9 and MC15 were also tested for their incorporation rate of NTP: MC15 did not show better efficiency than the wild-type (FIG. 4c) while DW9 showed an efficiency comparable to CS13 mutant (FIGS. 4a and 4c). Overall the best mutants are CS13 and DW9 which both carry the E2335G mutation, with a significantly altered substrate specificity towards ribonucleotides and with an enhanced processivity of RNA molecule extension compared to the pol θ WT. It also opens the way to investigate the incorporation of modified nucleotides by the same mutants.

Figure 4D:
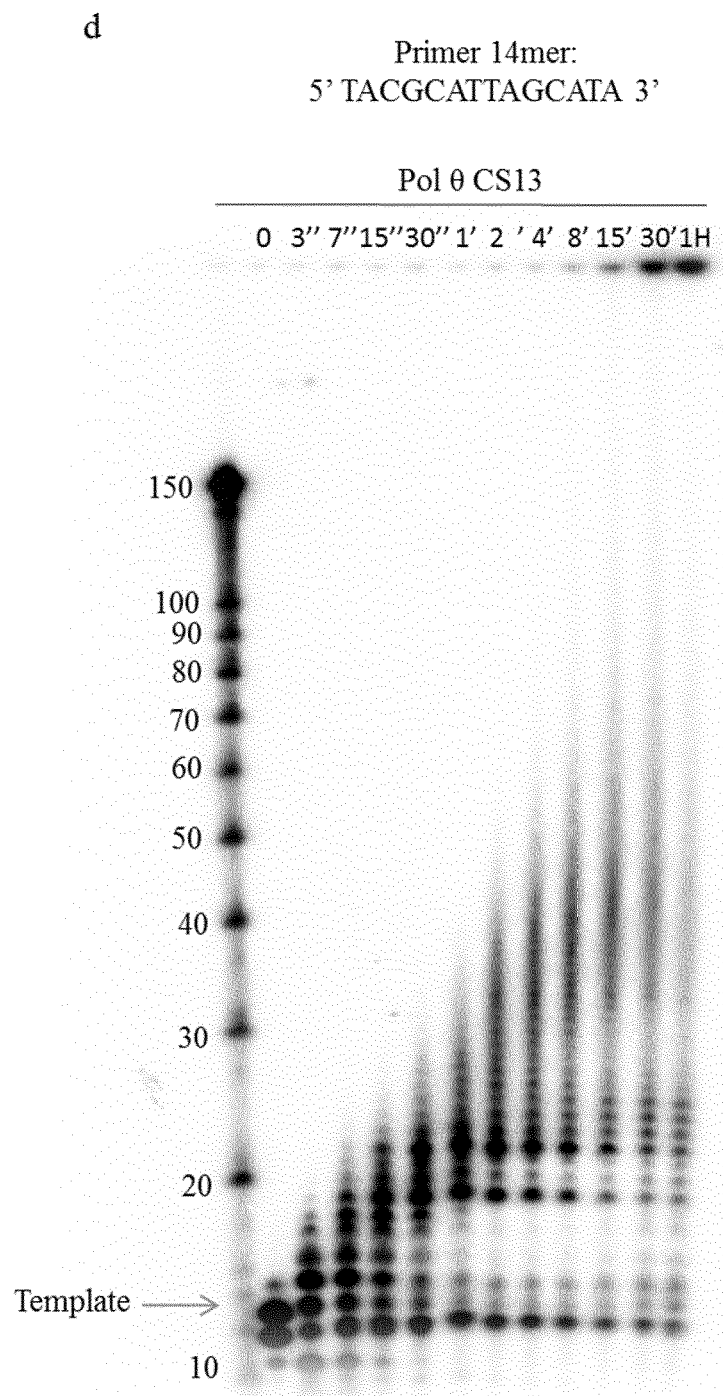

In the perspective of generating a library of random sequences of RNA with controlled fragment lengths the kinetics of primer extension was performed in the same conditions and allowed to monitor the length of the products as a function of the reaction time. In the case of 20-30 nt RNA fragments, 1 min-reaction is sufficient to complete the synthesis, which shortens significantly the SELEX process of aptamer assembly (FIGS. 4b and 4d).

Structural Model of Incorporation of Ribonucleotide by CS13 Mutant

CS13 mutant exhibited an efficient (ribo)nucleotidyltransferase activity by extending a 14-mer ssDNA primer in the presence of $Mn^{2+}$. This novel attribute is provided by the substitution of the charged glutamate residue E2335 by the small and flexible glycine residue. The steric gate residue E2335 is located in close proximity of the sugar moiety of the incoming nucleotide. In the case of ddATP-pol theta (pol θ) structure (4X0P PDB code) the carboxylate group of the glutamate does not interfere with the positioning of the nucleotide (FIG. 5a). In the case of NTP, the presence of the hydroxyl group at the C2' position creates both steric hindrance and electrostatic constraints between the sugar moiety and the pocket shaped by the residues E2335, Y2387 and Y2391 (FIGS. 2c and 5b). The mutation E2335G obviously enlarges the nucleotide binding pocket and is indeed compatible with an increased ability to incorporate a ribonucleotide into the 3'-end of the ssDNA primer (FIG. 5c). Similar observations were described for *E. coli* phage T7 DNA polymerase, the ribose moiety of the incoming nucleotide is lodged between the aromatic ring of the residue Y526 and the aliphatic carbons of the E480 side chain, which itself is hydrogen-bonded to the hydroxyl of the strictly conserved Y530[13]. The spatial orientation of these residues forms a hydrophobic pocket at the C2' position of the ribose that might exclude ribonucleotides from the active site, thus providing a structural basis for the strong discrimination against ribonucleotide incorporation by DNA polymerases[13].

CS13 Mutant Incorporates Equally the Four Ribonucleotides and Generates a Random-Sequence Library of ssRNA.

The success of a SELEX method relies on the quality of the initial nucleic acids library. Therefore, the possibility to access to a large collection of random-sequence RNA or DNA fragments is essential. The CS13 mutant demonstrated an outstanding ability to elongate DNA primer with ribonucleotides. In order to confirm its added value, the incorporation rate of the four NTPs has been evaluated by HPLC analysis of the overall base composition of the newly synthesized RNAs. The RNAs were completely digested into ribonucleosides according to a published protocol[27] before HPLC separation. The chromatogram of the standards solutions of the four ribonucleosides (adenosine, guanosine, uridine and cytidine at concentrations of 0.1 mM or 0.25 mM in the digestion buffer) indicated four peaks eluted at 5.55-5.60 min, 6.36-6.39 min, 7.82-7.90 min, 9.74-9.75 min respectively for cytidine, uridine, guanosine and finally adenosine (FIGS. 6a and 6f). The inventors were interested in determining whether the composition of the initial ribonucleotide substrates NTP in the elongation reaction mix had an effect on the propensity of the polymerase to incorporate one ribonucleotide at the expense of another. The denaturing gels of the products generated by the CS13 mutant (FIGS. 4a and 4c) indicated that in presence of an equal proportion of the four NTPs (1:1:1:1 at 0.5 mM each), long polymers of RNA were synthesised but they give no indication on the distribution of each NTP along the sequence. However, the incorporation of each of the four NTPs displayed different trends when used at 0.1 mM each as the UTP seemed to be less integrated by the enzyme. These differences were not observed any more when using the four nucleotides at 0.25 mM each. Thus, the reaction products from NTPs (1:1:1:1) were cleaned up and hydrolysed, and the resulting ribonucleosides were analysed by HPLC (FIGS. 6d and 6g). In addition, another synthesis condition has been prepared containing tenfold UTP (1:1:1:10) and analysed in the same way (FIGS. 6e and 6h). For both conditions, four peaks were observed, corresponding to the retention time of the four nucleosides, but the calculated peak areas of each component revealed different distributions (Table I, FIG. 1). The initial mix of 1:1:1:1 NTPs resulted in a global scattering of $21\%_{mol}$ C, $41\%_{mol}$ G, $16\%_{mol}$ A and $19\%_{mol}$ U (FIGS. 6d) or $24.8\%_{mol}$ C, $24.6\%_{mol}$ G, $22.1\%_{mol}$ A and $28.6\%_{mol}$ U (FIG. 6g), whereas the initial mix of 1:1:1:10 NTPs gave $18\%_{mol}$ C, $24\%_{mol}$ G, $14\%_{mol}$ A and $49\%_{mol}$ U (FIGS. 6e) or $7.6\%_{mol}$ C, $9.0\%_{mol}$ G, $7.6\%_{mol}$ A and $75.9\%_{mol}$ U (FIG. 6h). This result highlighted the possibility to modify the initial substrate composition to modulate or favour the incorporation of one or several specified nucleotide(s) in the final products. Moreover, it is worth noting that the equimolar combination of only two NTPs (A/C; FIGS. 6b and 6i and U/G; FIGS. 6c and 6j) exhibited an equal probability of incorporation of both substrates (approximately $49\%_{mol}$ C, $47\%_{mol}$ A and $57\%_{mol}$ G, $34\%_{mol}$ U (FIG. 6c); approximately $55.8\%_{mol}$ C, $44.2\%_{mol}$ A and $51.9\%_{mol}$ G, $48.1\%_{mol}$ U (FIG. 6j).

In summary HPLC analyses helped to confirm that the CS13 mutant accepts roughly equally the four natural NTPs, ensuring the randomness of the sequence of each synthesized fragment.

Figure 7A:
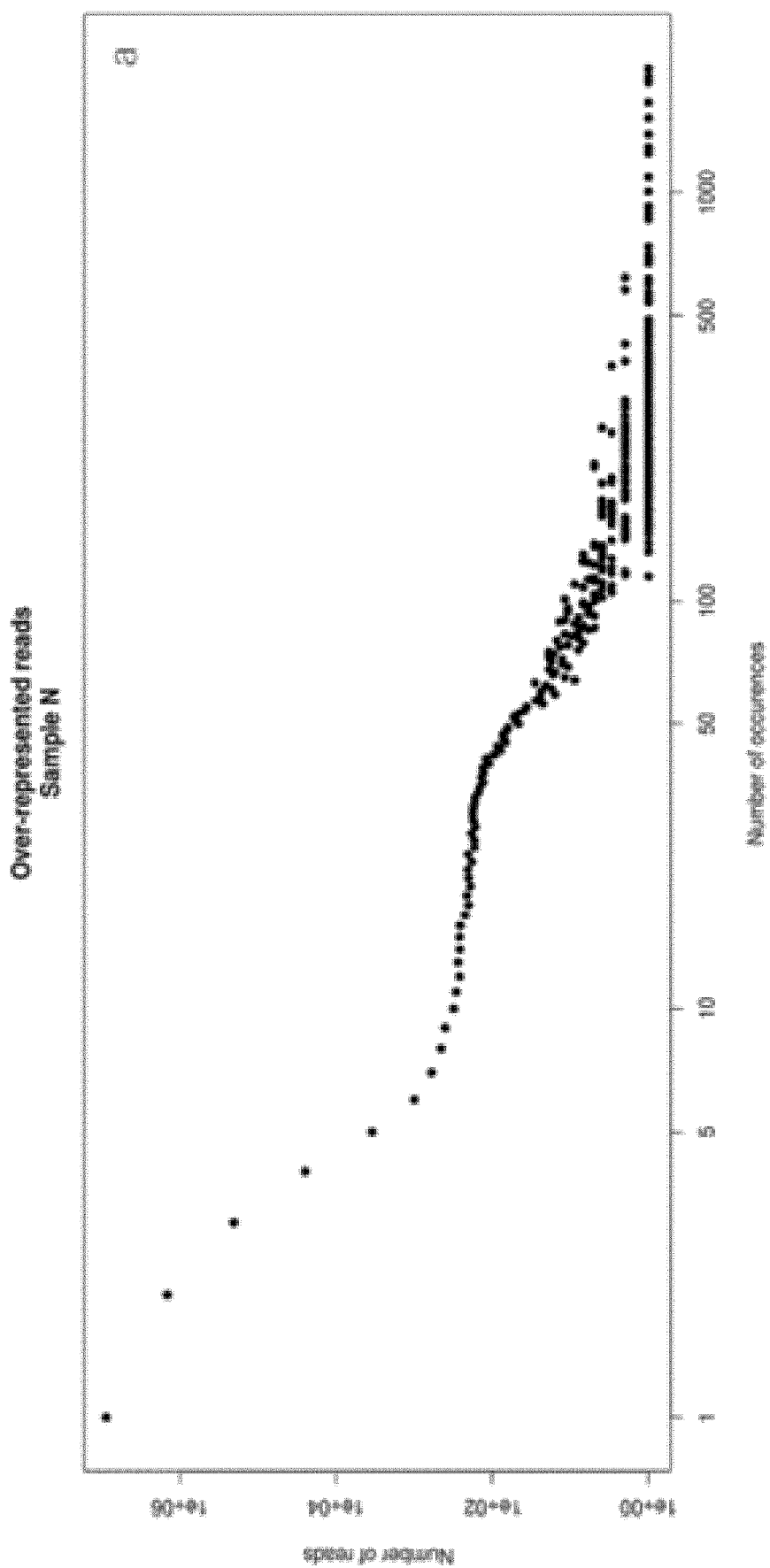
Figure 7B:
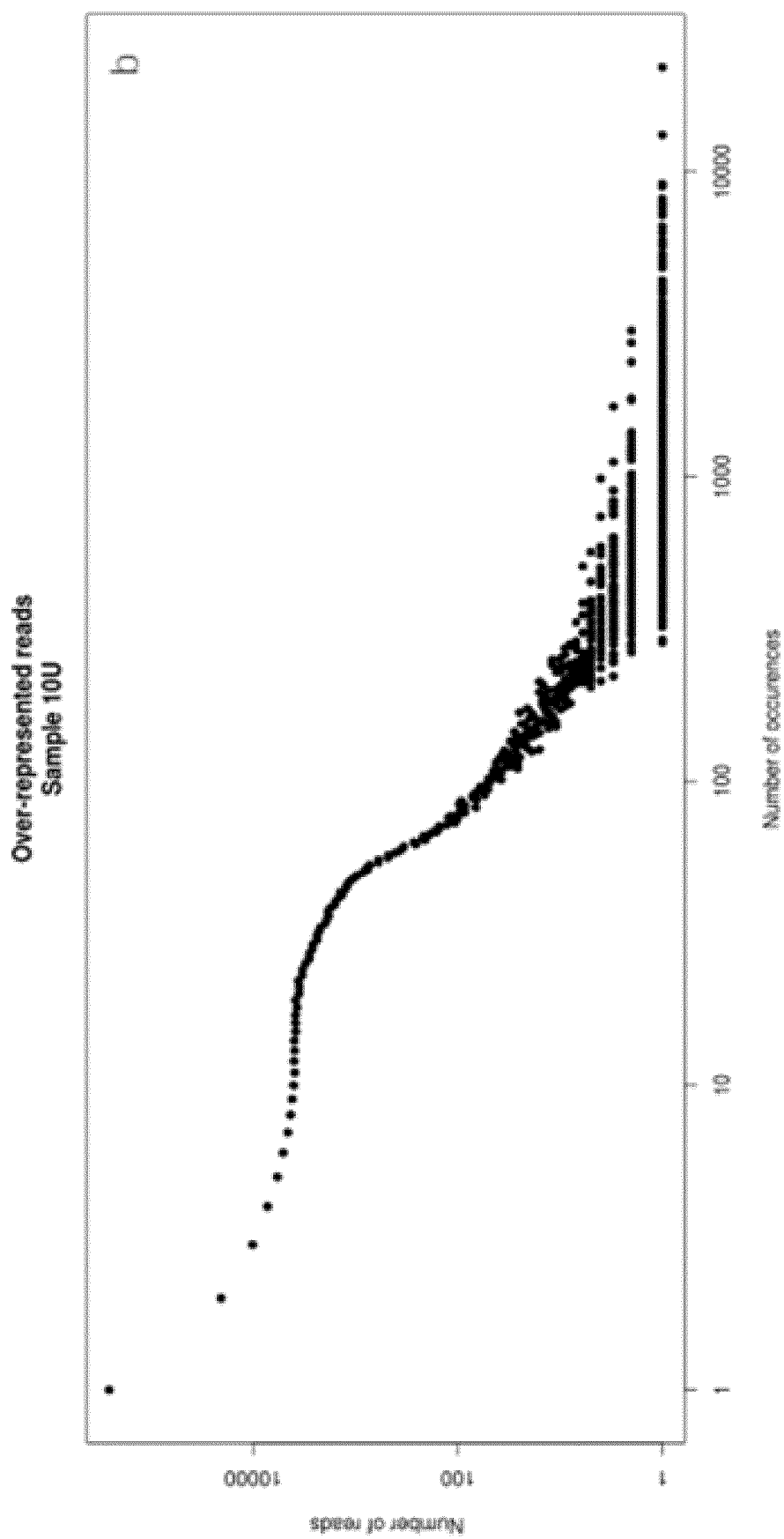
Figure 7C:
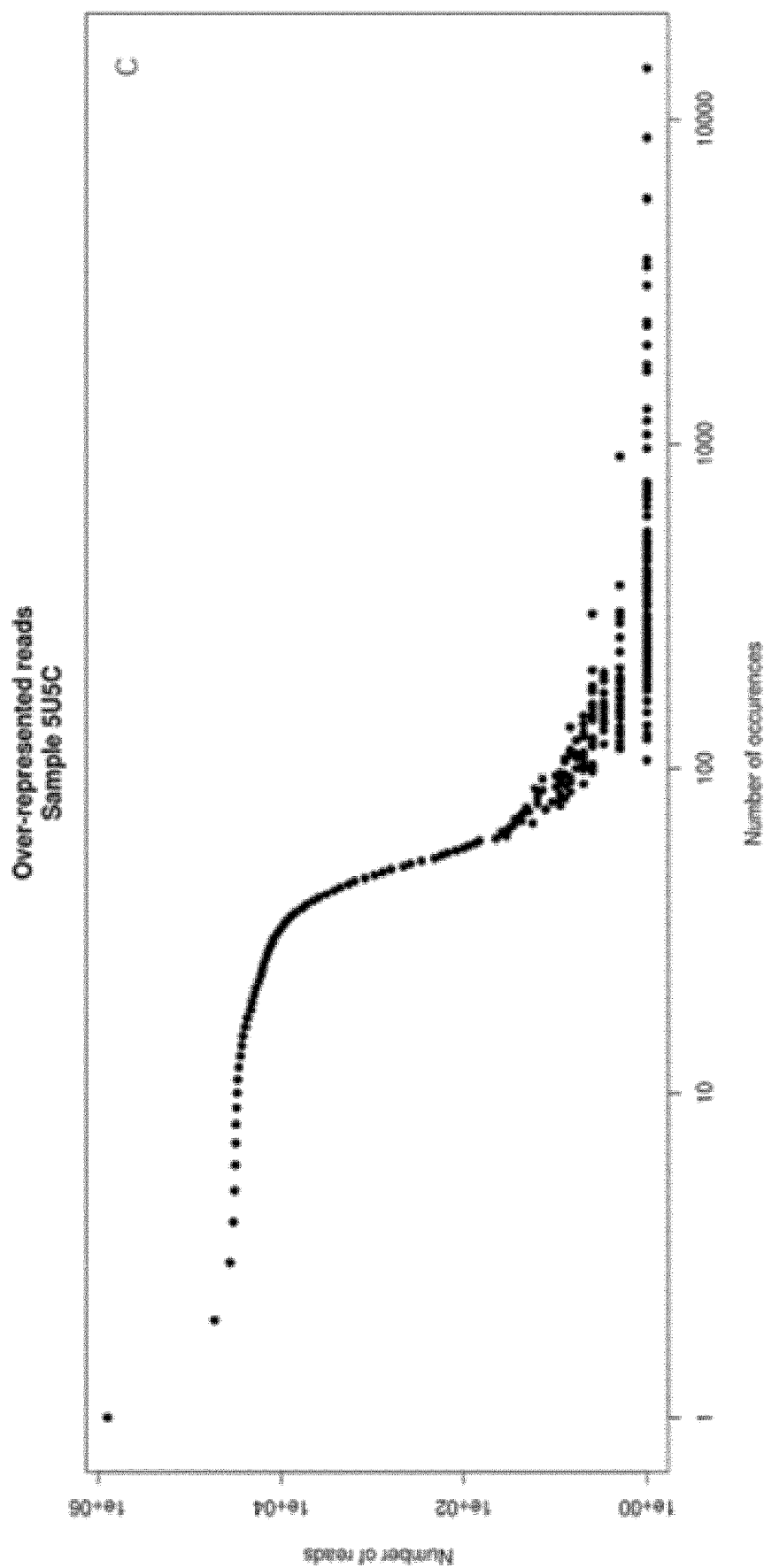
Figure 7D:
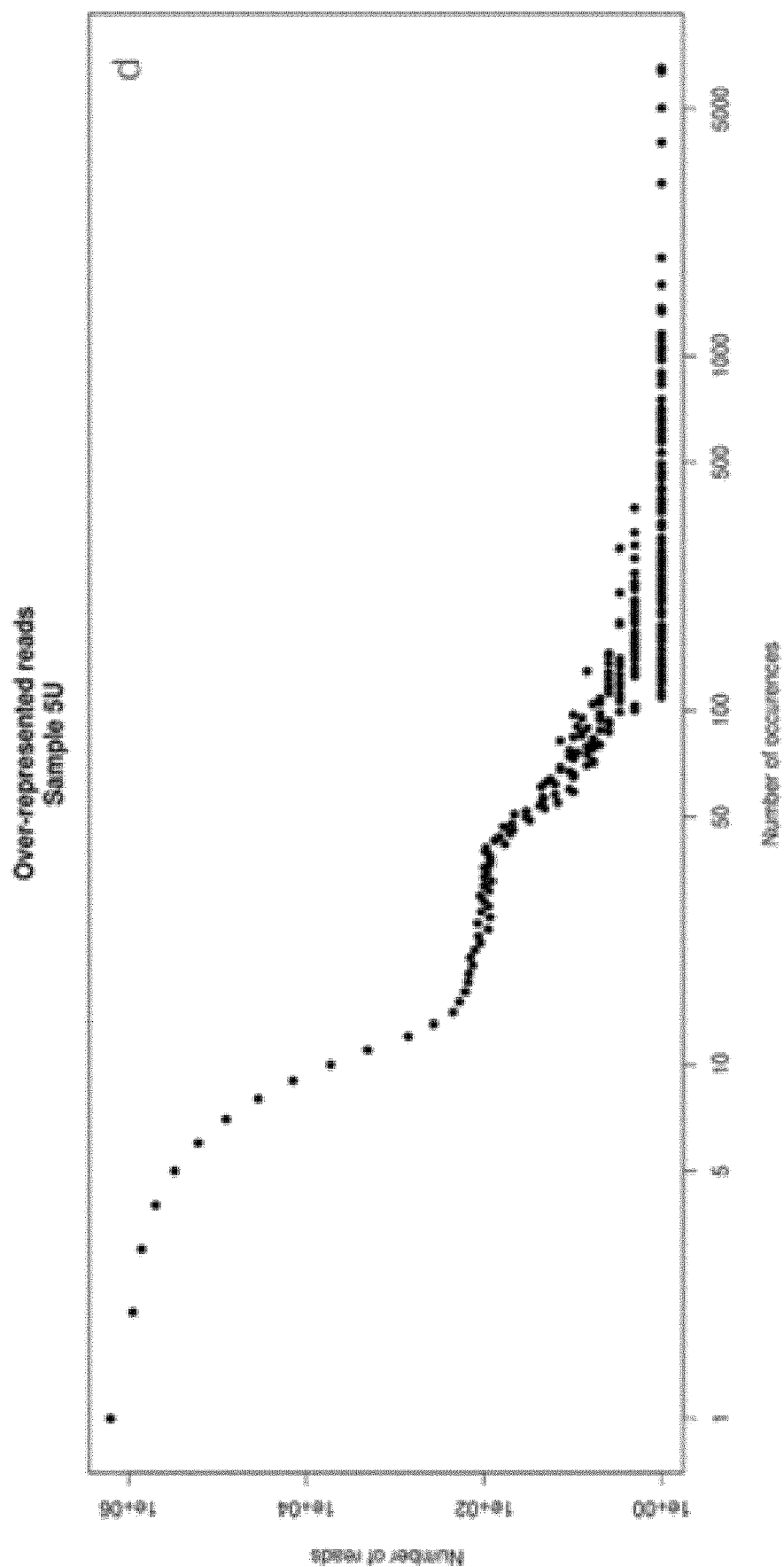
Figure 8A:
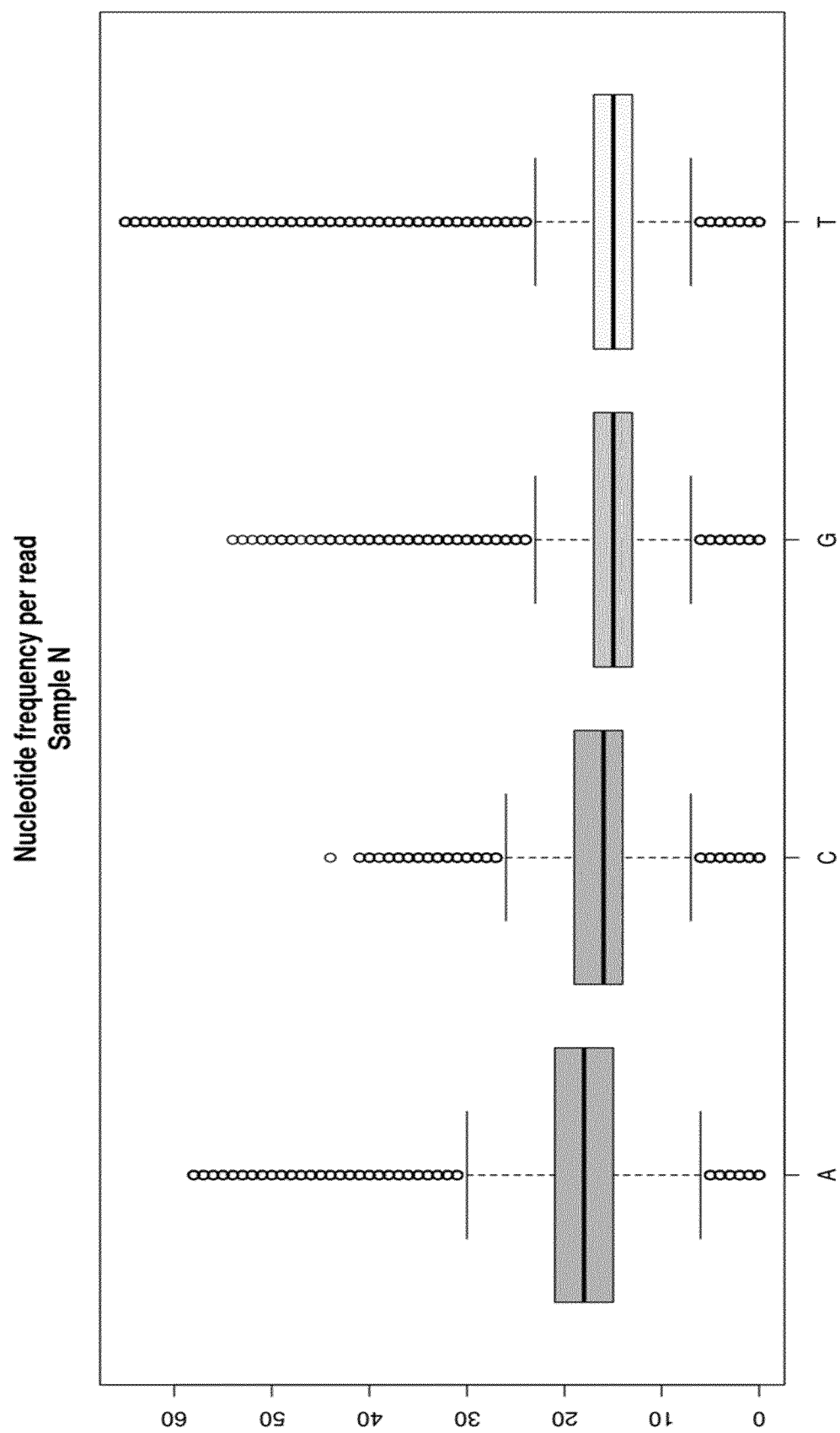
Figure 8B:
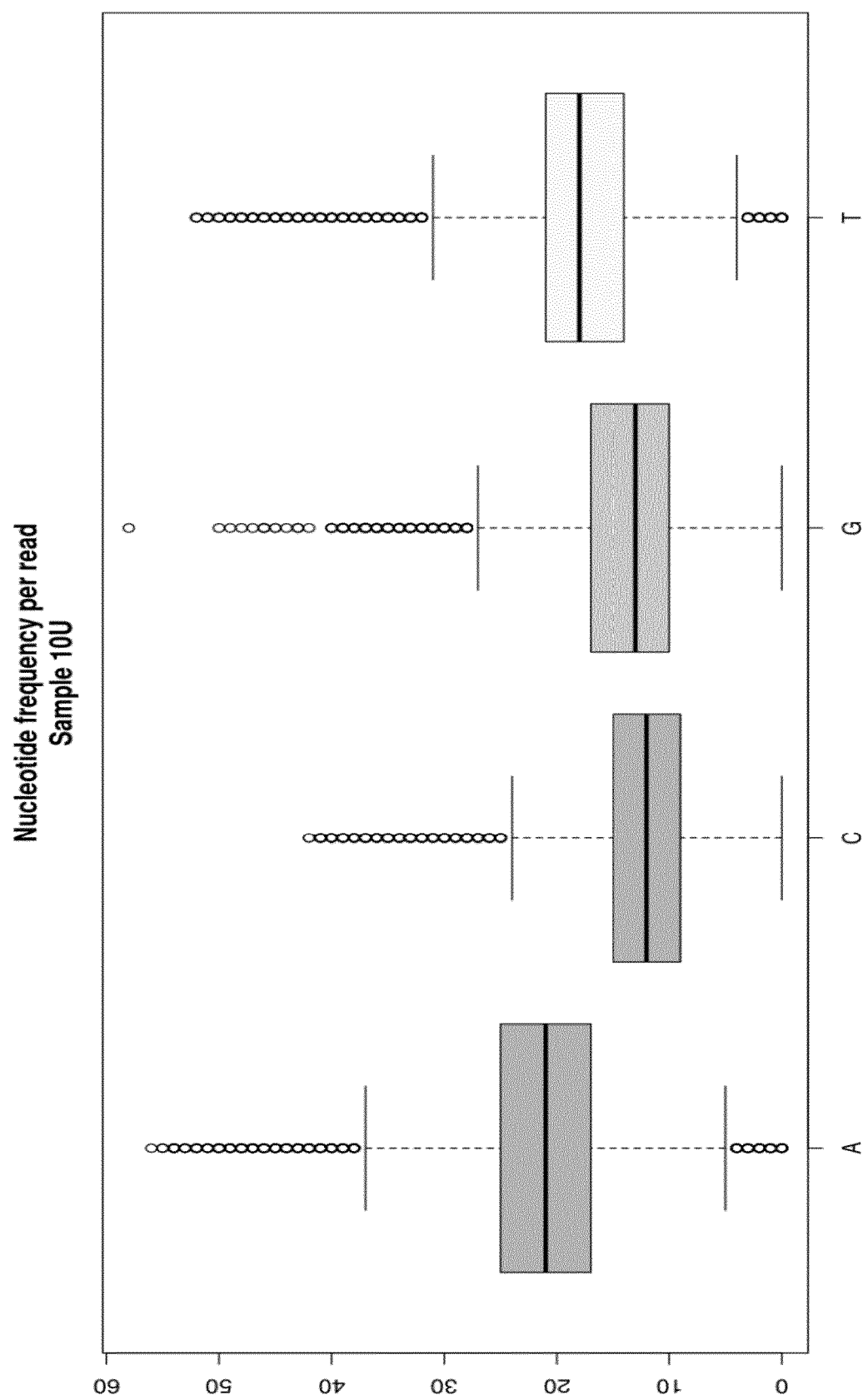
Figure 8C:
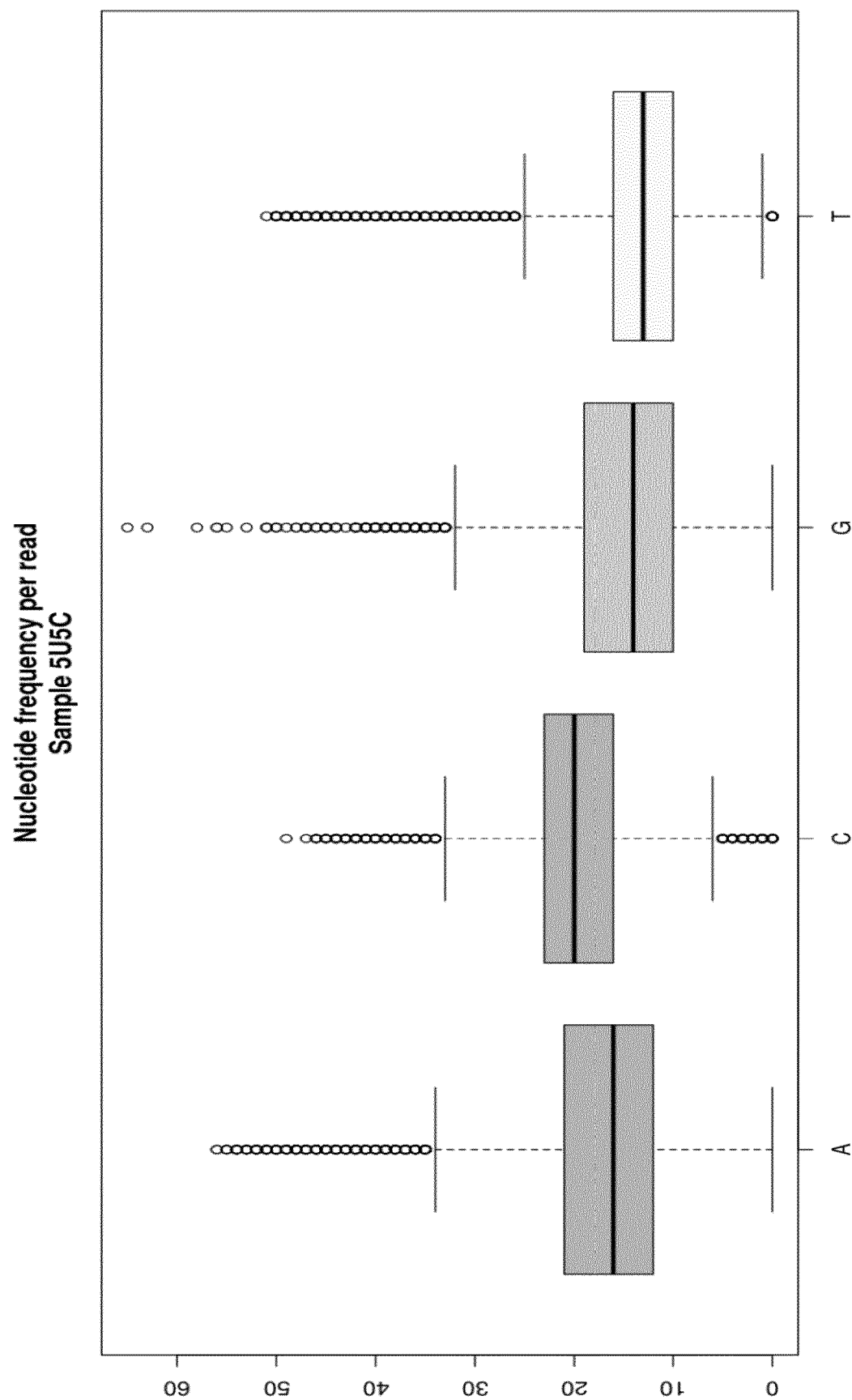
Figure 8D:
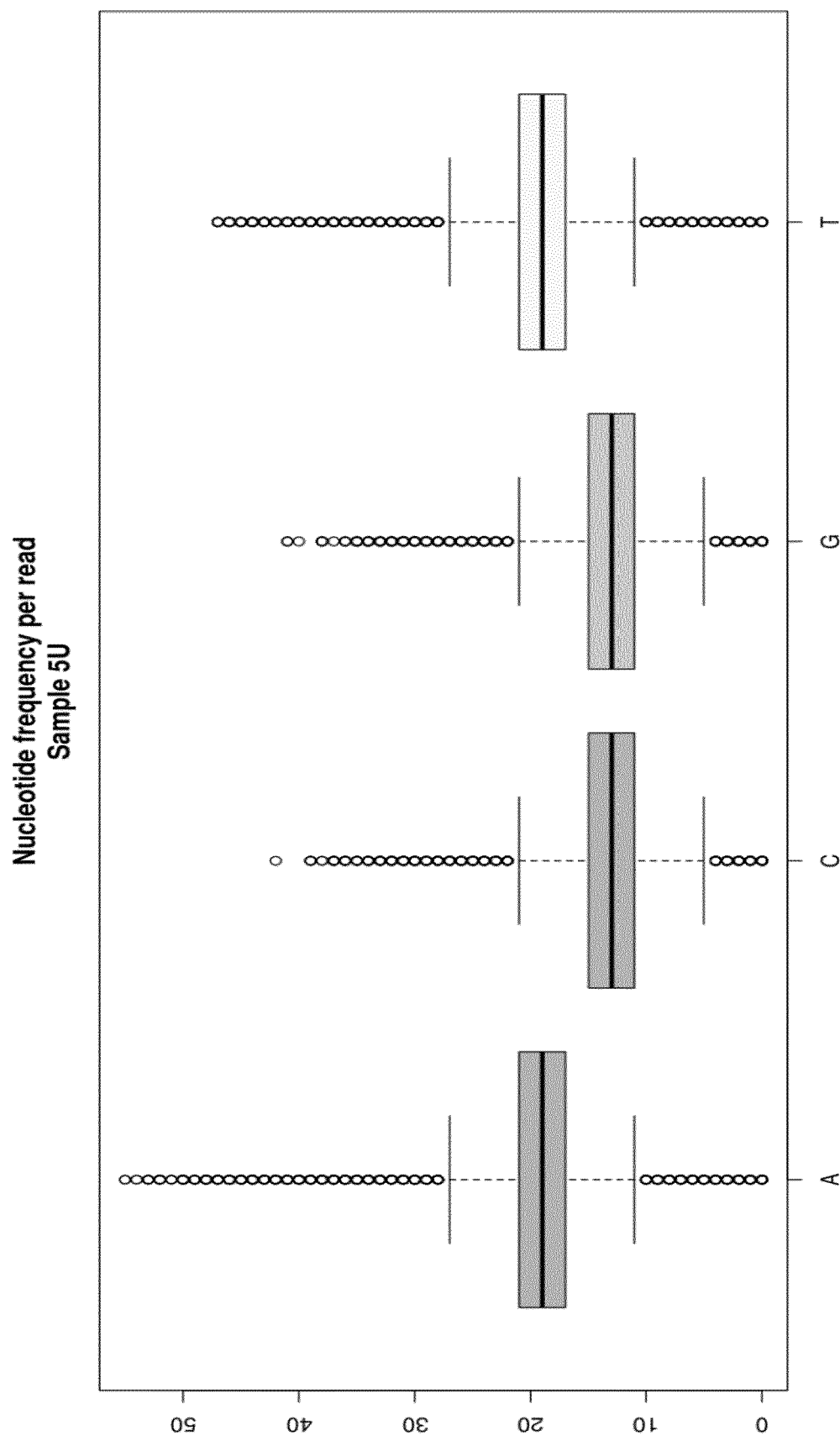
Figure 9A:
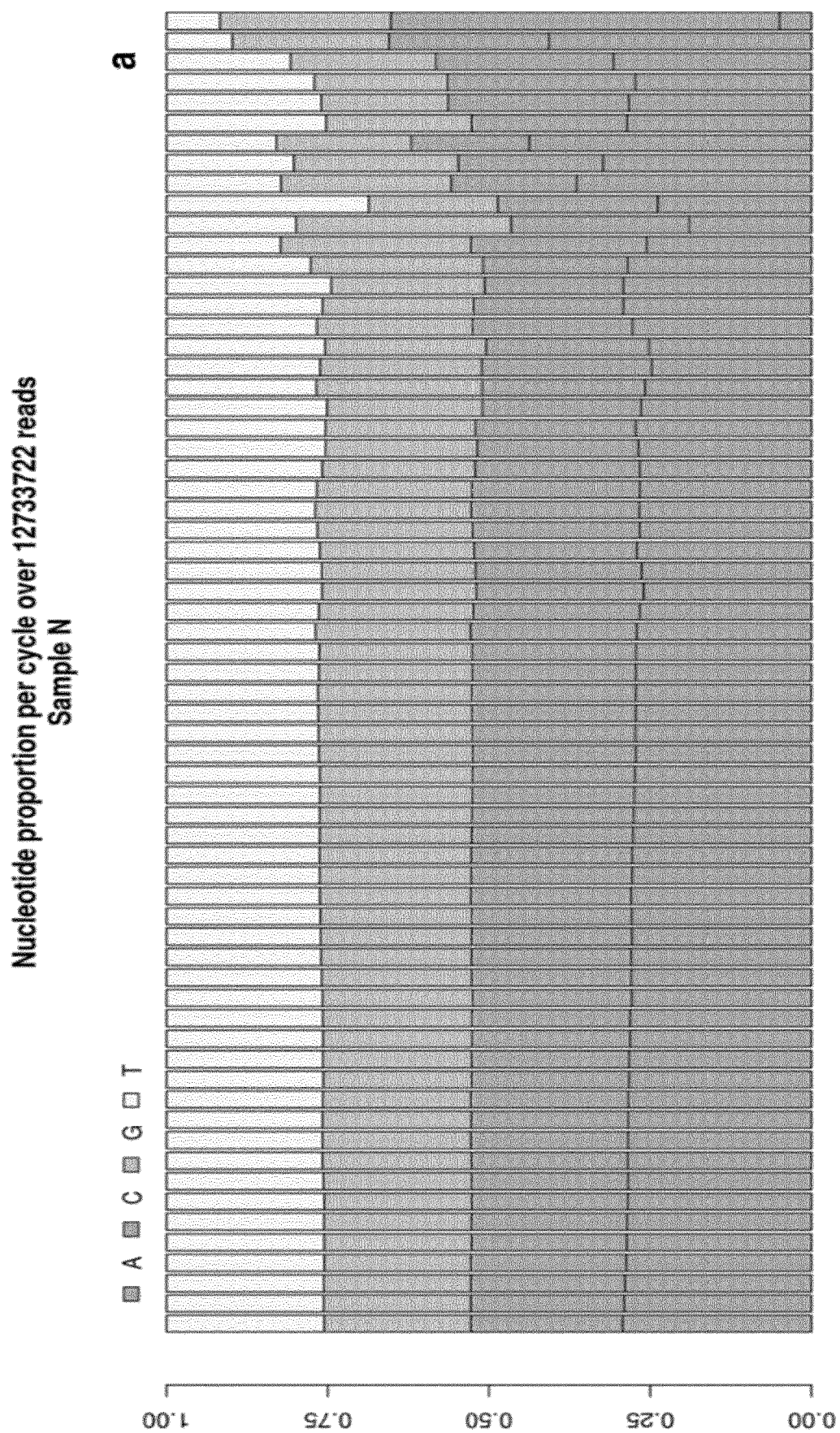
Figure 9B:
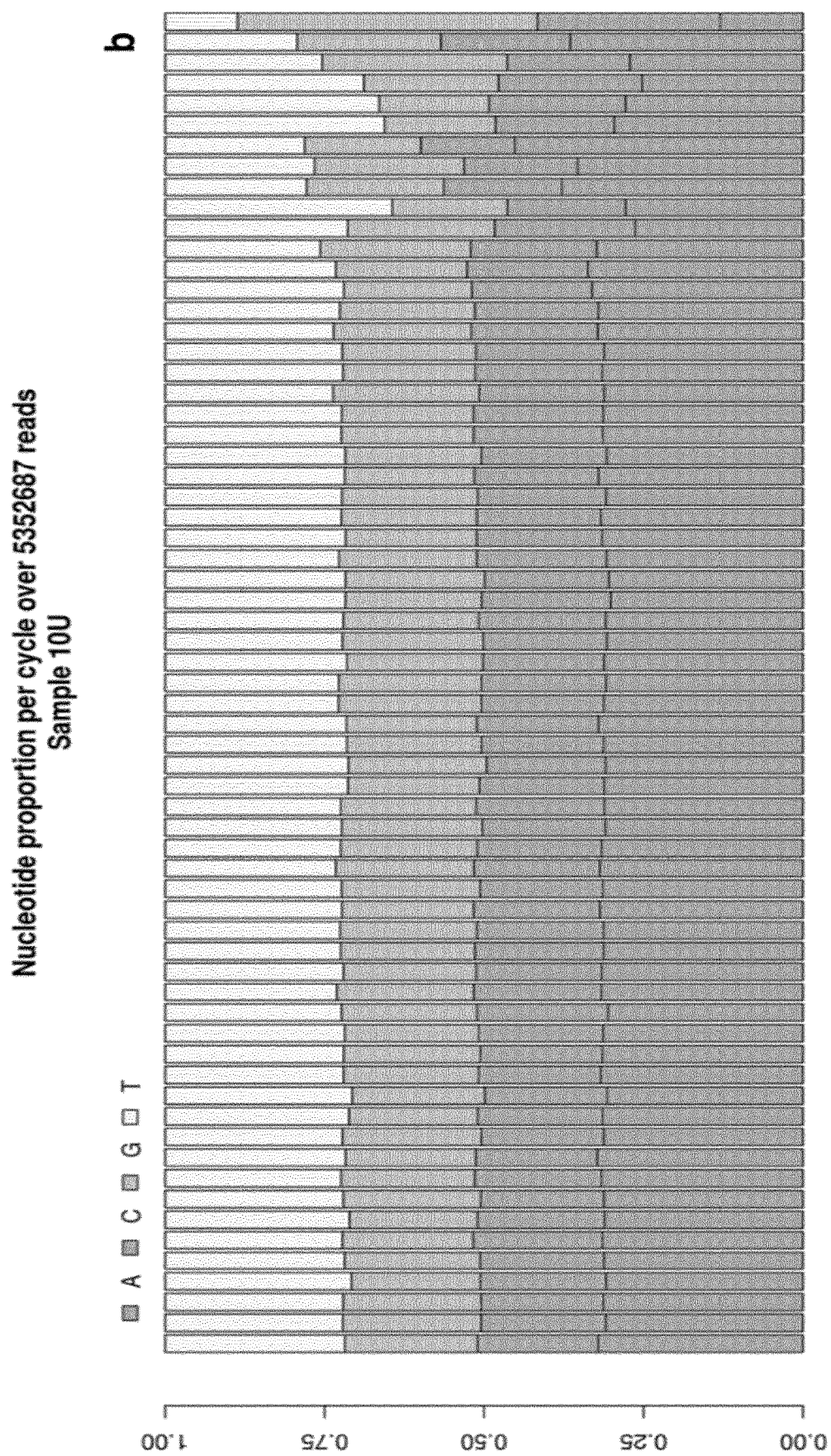
Figure 9C:
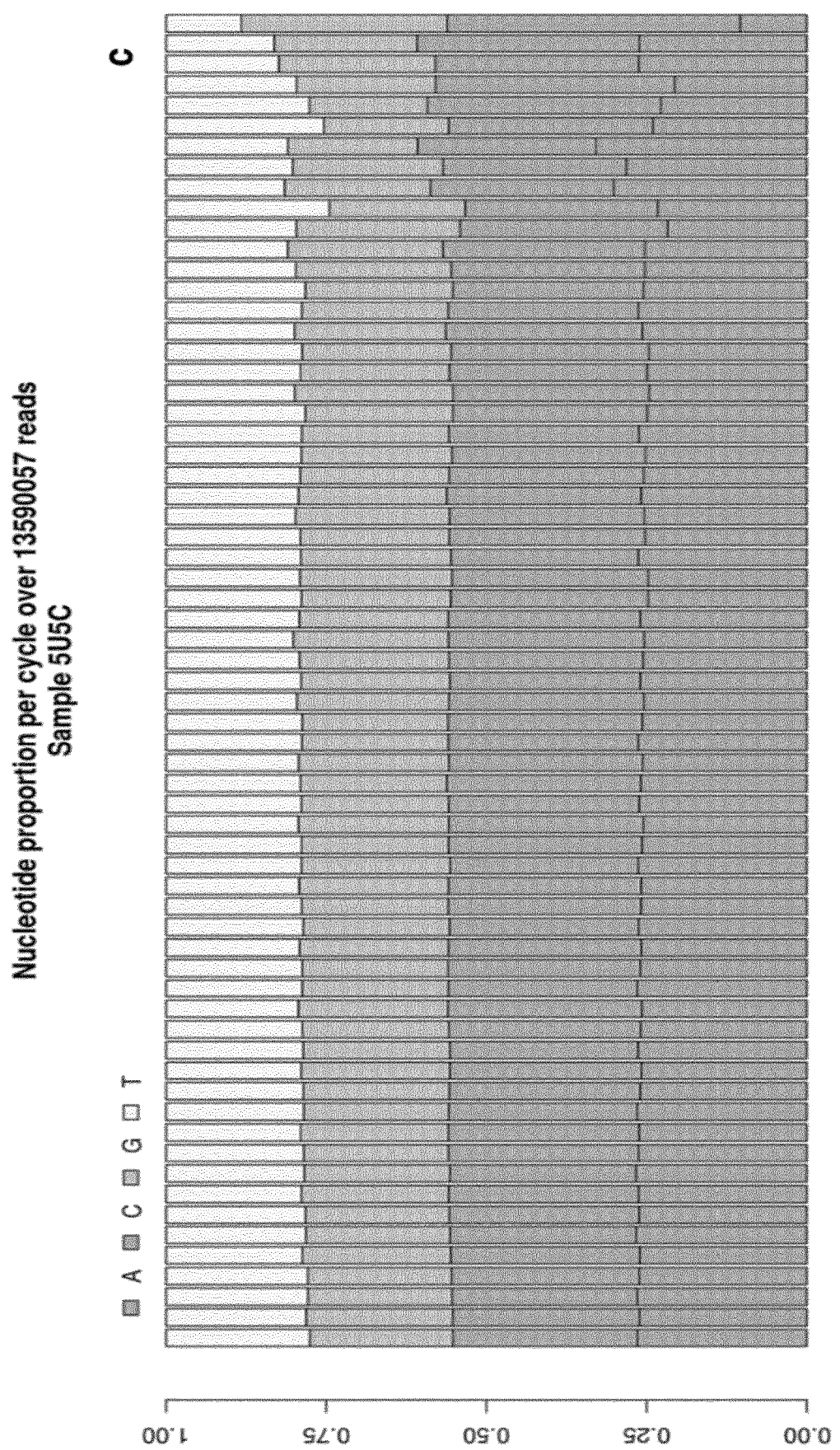
Figure 9D:
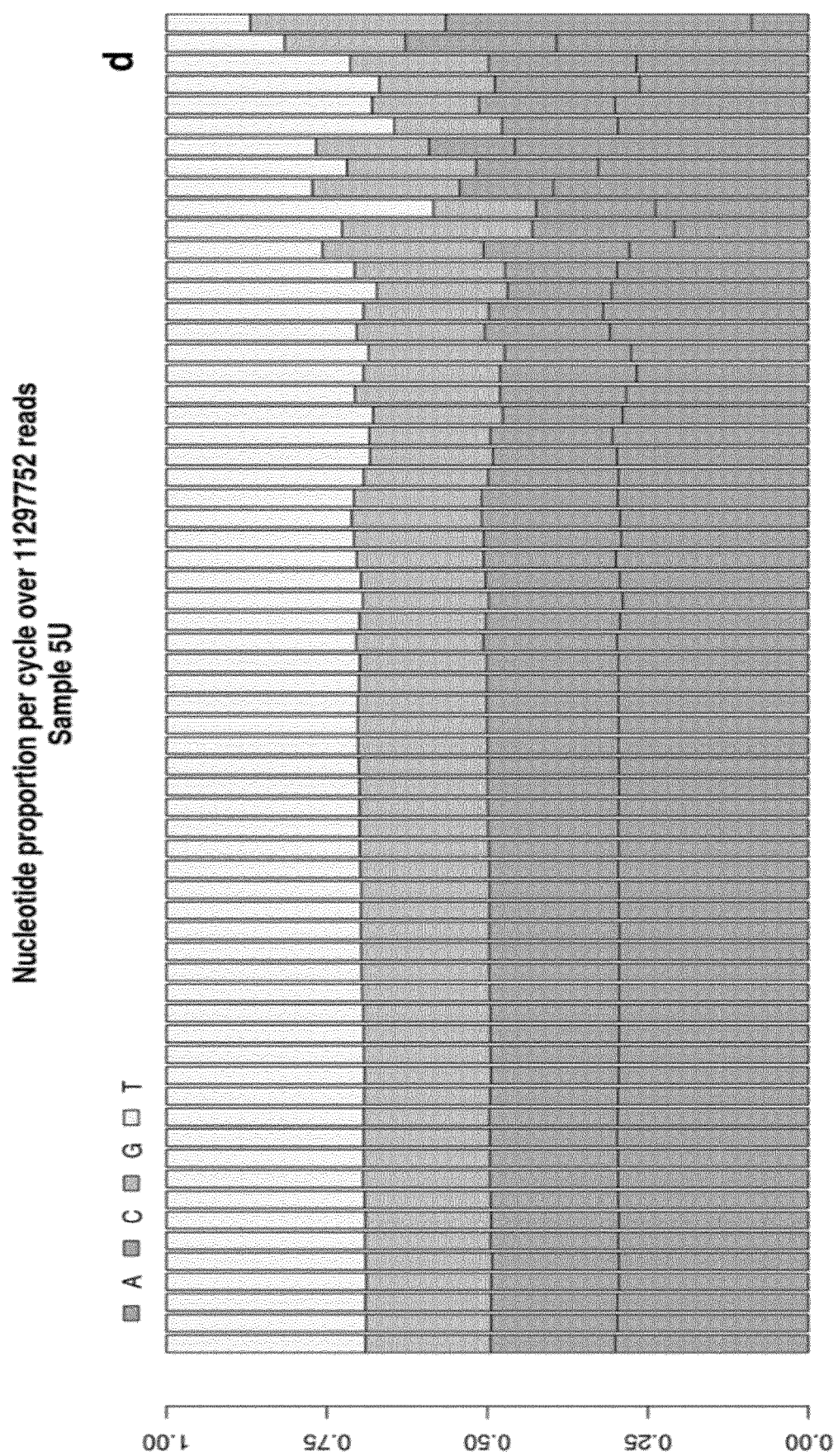

The sequencing of RNA products revealed more details about the ribonucleotides incorporation behaviour of the mutant CS13. For the different conditions tested the RNA library displayed between 5 to 14 millions of reads. For the whole library, the occurrence of the different sequences was estimated and was plotted as illustrated in the FIG. 7. Among 12,733,722 reads in the sample 'N', 8,766,652 reads had unique sequence (occurrence=1), representing almost 70% of the total reads in the library (FIG. 7a). The rest being dispersed between 2 (1,441,628 other reads with sequences repeated twice) and 2000 occurences (1 sequence). When the ratio of UTP has been increased in the synthesis mix (samples '10U', '5U' and '5C5U') the number of unique reads drastically decreased, multiplying the number of repeated reads. Anyway, the majority of the reads had a moderate number of occurrences ranged between 2 to 100 for the three conditions (FIGS. 7b, 7c and 7d). These results demonstrated the randomness of each RNA pool and insured a starting library size of $10^6$-$10^7$, that represents the typical size used for SELEX[31]. Another statistical parameter that has been evaluated is the frequency of each ribonucleotide per read and per incorporation cycle (FIGS. 8 and 9). Globally, the four synthesis conditions indicated a slightly equivalent frequency (20-25% each; 26.7% A, 25% C, 24% G et 24.3% U) for the four nucleotides. Within the 65 cycles, the global proportion of added nucleotide remained constant with an increased value for UTP when an excess of UTP has been added ('10U' and '5U') to the detriment of CTP incorporation (FIGS. 9b and 9c). When CTP is 5-fold concentrated ('5C5U'), the amount of CTP incorporation has been also increased.

Figure 10A:
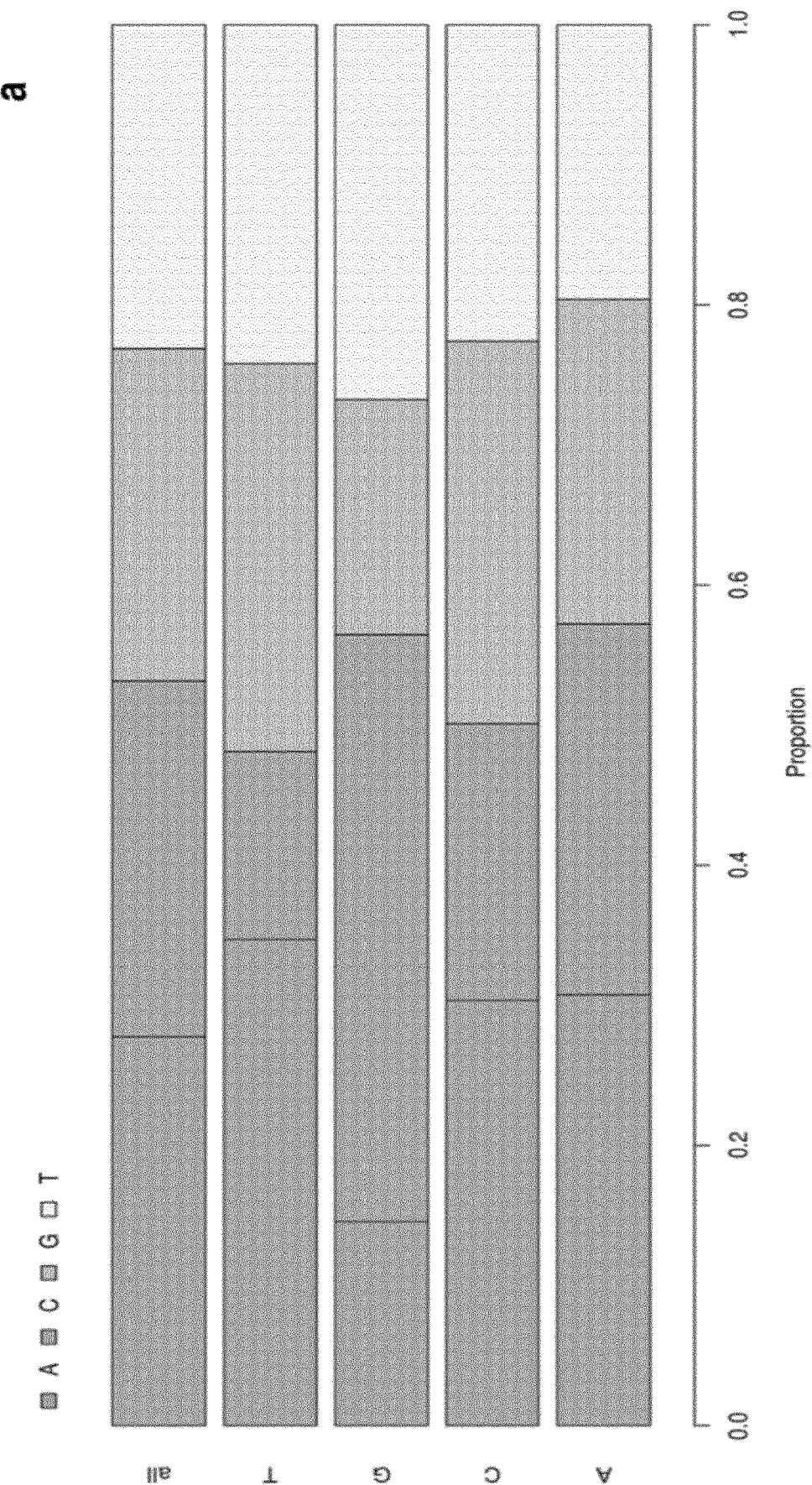
Figure 10B:
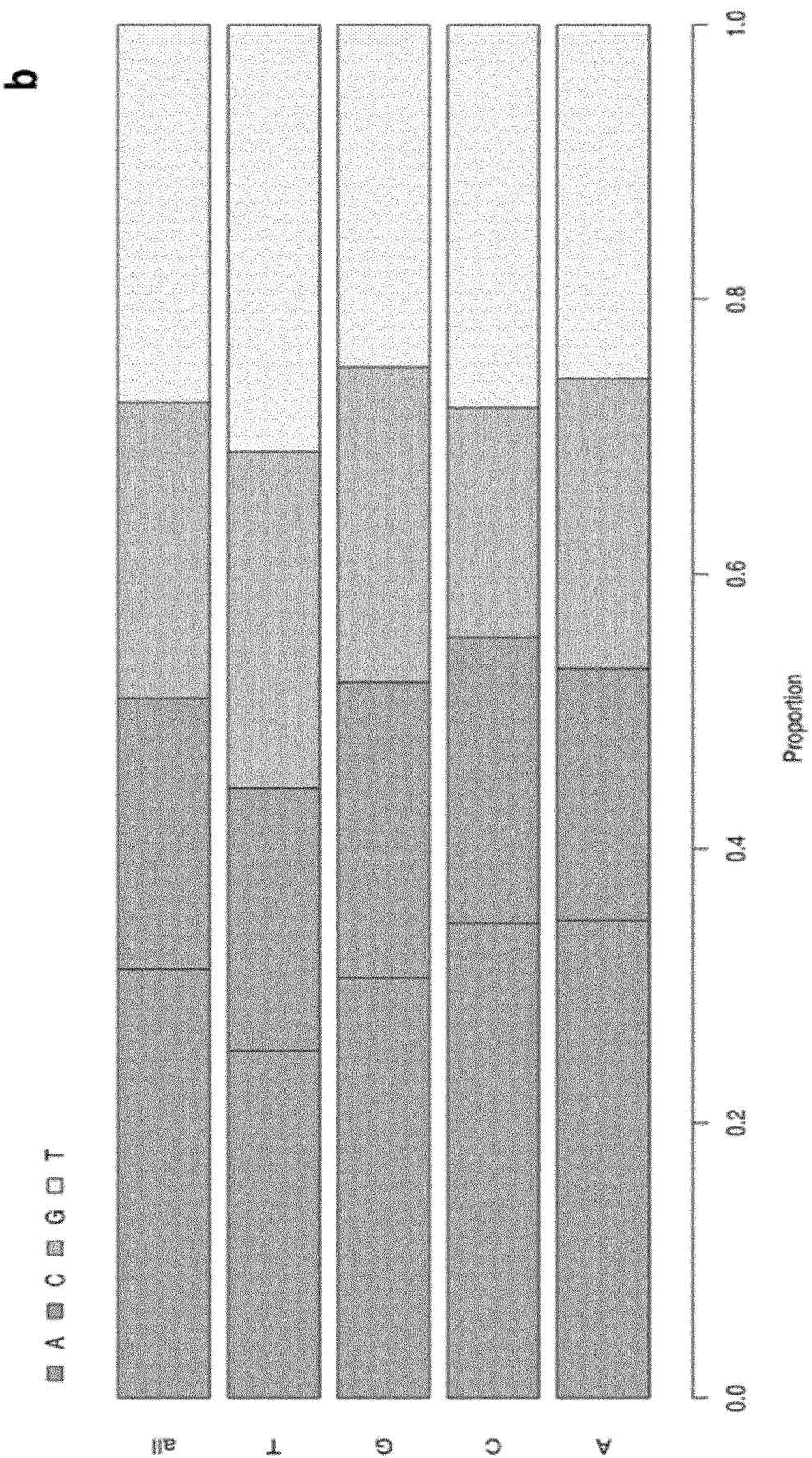
Figure 10C:
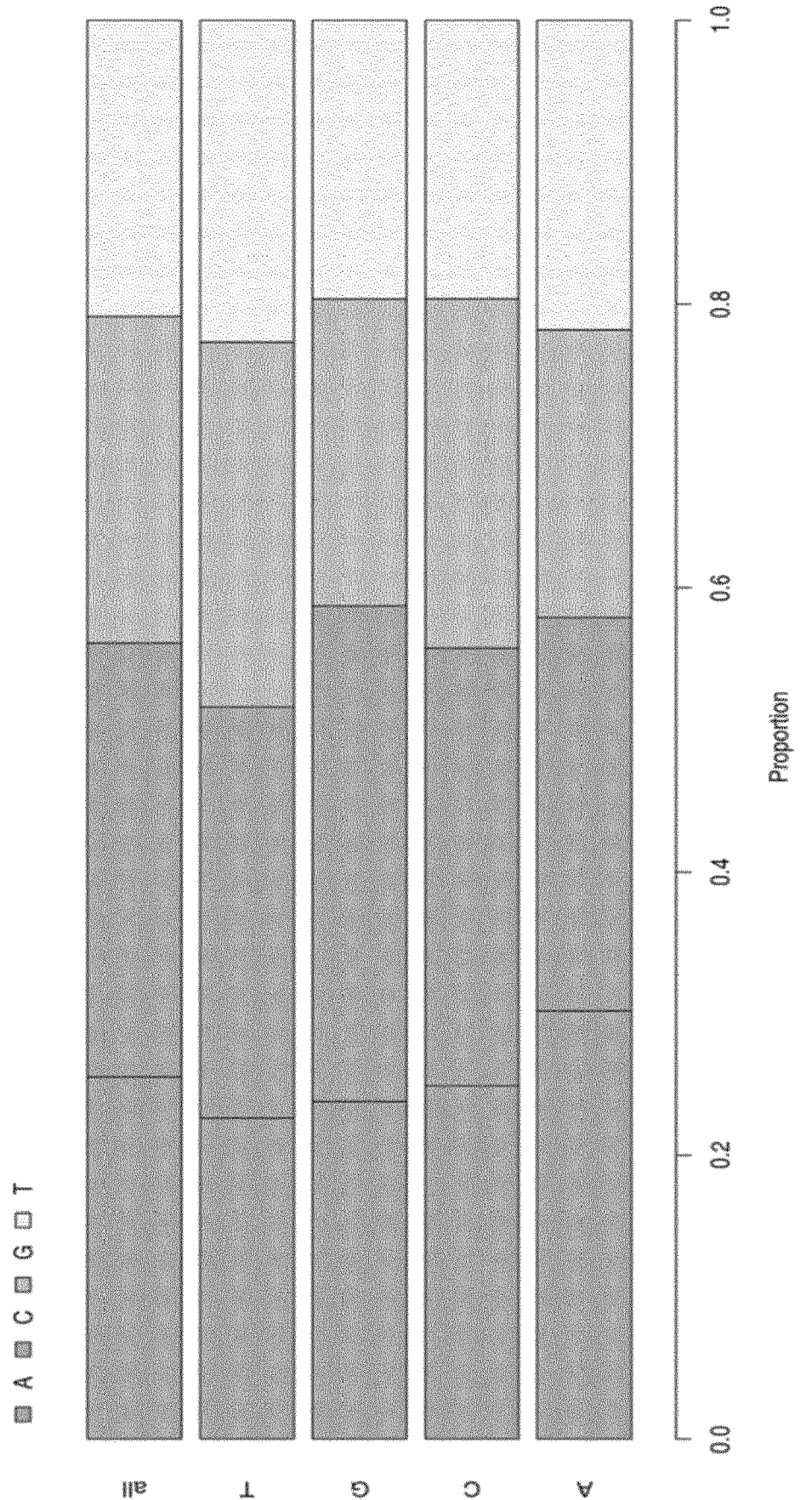
Figure 10D:
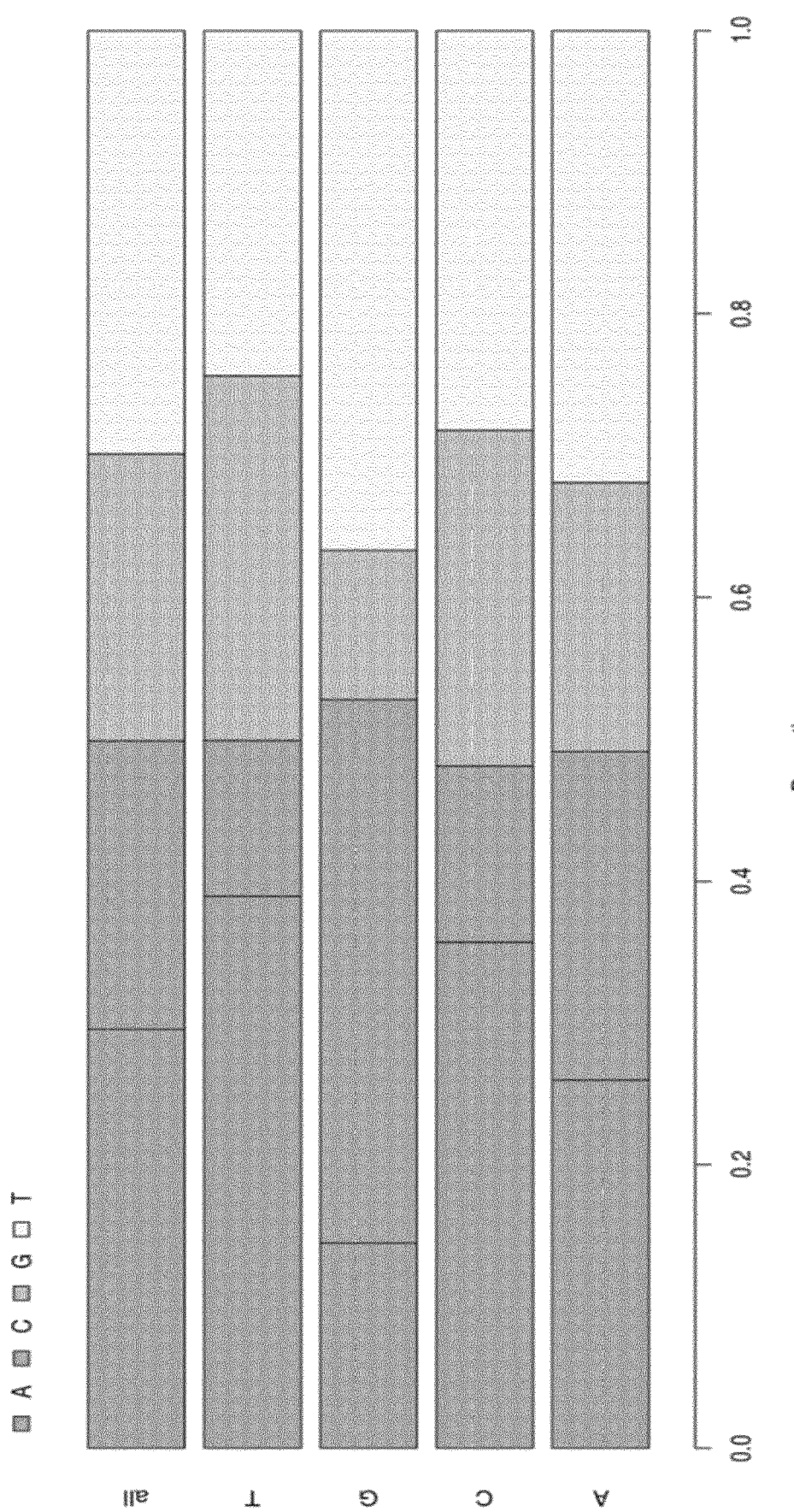

Finally, the probability of adding one (A/C/G/U) nucleotide in position N after a given nucleotide in position N-1 has been estimated for the four same conditions. This parameter might indicate the frequency of forming dinucleotides in each sequence. Among the 16 possible dinucleotides, GC seemed to be the most plausible when an equimolar ratio of ribonucleotides is present, to the opposite, it is less probable to form UC and GG dinucleotides in the same case (FIG. 10a). The increase of UTP amount in the other conditions seemed to increase the probability of incorporation of U after a U (UU dinucleotide) only when it is present in a 10-fold excess (FIG. 10b). When UTP and CTP were present in 5-fold excess (FIG. 10c), an equilibrium of the transition behaviour took place for all the nucleotides (every scenario is possible). Lastly, a 5-fold increase of UTP amount (FIG. 10d) appeared to promote the formation of GU dinucleotide compared to the condition 'N'.

Put together, these results proved the randomness of the RNA pool synthesis and the suitable size of the generated libraries, which validates their use for SELEX procedures.

Modified Nucleotides Incorporation by the CS13 and DW9 Mutants

The major drawback of aptamers is their relative instability and sensitivity to hydrolysis in biological fluids. The solution to bypass this point is to produce nuclease-resistant RNA molecules by different approaches[32-34]. Modifications can be attempted on the nucleotide sugar moiety, the phosphodiester covalent link or on the base.

The incorporation of modified deoxy- and ribonucleotides has been also investigated in this study. The following analogs were successfully accepted and resulted in long polymers: 2'-Fluoro-dNTP (2'-Fluoro-dUTP, 2'-Fluoro-dATP, 2'-Fluoro-dCTP, 2'-Fluoro-dGTP, 2'-Fluoro-dTTP, and mixtures thereof), 2'-Amino-dNTP (2'-Amino-dATP, 2'-Amino-dCTP, 2'-Amino-dGTP, 2'-Amino-dUTP, 2'-Amino-dTTP, and mixtures thereof), 2'-O-methyl-dNTP (2'-O-methyl-dATP, 2'-O-methyl-dUTP, 2'-O-methyl-dCTP, 2'-O-methyl-dGTP, and mixtures thereof), 2'-azido-2'-dNTP (2'-azido-2'-dATP, 2'-azido-2'-dUTP, 2'-azido-2'-dCTP, 2'-azido-2'-dGTP, and mixtures thereof), 5-methyl-UTP, Ara-ATP (Vidarabine triphosphate), Ara-CTP (Cytarabine triphosphate), 2'-O-methyl-ATP, 2'-O-methyl-CTP, epsilon (ε)-ATP, 2-Aminopurine, FANA, 5-ethynyl-UTP.

All the 2'-fluoro (FIG. 11, lanes 1-5; FIG. 14, lanes 16 to 21) and 2'-amino modified nucleotides (FIG. 11, lane 9; FIG. 14, lanes 1 to 15) were efficiently incorporated (FIG. 11 and FIG. 14). It has been described that the incorporation rate of fluoro-modified ribonucleotides by T7 RNA polymerase was ten-fold lower than that of the natural substrates[33]. CS13 mutant depicted a high tolerance for these modified substrates as long homopolymers (up to 200 nt) were synthesized in the same experimental conditions as the primer extension by natural NTPs or dNTPs, with a much greater efficiency than pol θ WT. This modification is suitable for ribozyme development and aptamers selection as the fluoro-modified oligonucleotides have better ribonucleases resistance[35,36]. The incorporation of 2'-fluoro modified nucleotides by DNA polymerases were already assessed in several studies[37] and the incorporation rate of modified nucleotides by enzymatic synthesis remains relatively limited compared to the chemical synthesis. In that way, many efforts are still being focused on the substrate specificity of DNA polymerases to benefit from the attractive properties of different types of modified oligonucleotides.

The CS13 mutant failed to elongate the ssDNA primer in presence of 2' O-Methyl modified nucleotides further than just a few nucleotides (FIG. 11, lanes 13 and 14; FIG. 14, lanes 6 to 10). 2'-O-methyl-modified RNA display better stability against base hydrolysis and ribonucleases as well as increased Tm values. This attribute may be useful to preserve the 3D conformation and to widen the diversity of a functional aptamers[38].

The incorporation of 2'-amino dATP and 2'-amino dGTP (FIG. 14, lanes 1-5) appeared to be qui efficient with the CS13 mutant, more than the 2'-amino dUTP and 2'-amino dCTP. For 2'-N$_3$ (azido) dNTP, the incorporation was very good with the mutant CS13, almost as good as the 2'-F derivatives, allowing the possibility to form click chemistry experiments with compounds containing an alkyne group (FIG. 14, lanes 11-15).

Etheno-ATP (FIG. 11, lane 15; FIG. 14, lane 25) formed also long polymers with CS13 mutant. This base-modified nucleotide is fluorescent in solution and is often used in fluorescence-quenching application or FRET-studies on conformational changes.

Otherwise, FANA (FIG. 11, lane 17) (2-deoxy-2-fluoro-arabinonucleotide) seemed to be accepted by CS13 mutant but it failed to elongate primers into long polymers. It has been described that FANA-aptamers showed greater thermal stability, nuclease resistance and a stronger binding into their targets such as thrombin or, HIV-1 reverse transcriptase[39] for which the binding affinity is in the picomolar range and demonstrated an efficient activity in vitro. Two fluorescent analogues of adenine nucleotides were tested: etheno-adenine (FIG. 14, lane 25; FIG. 11, lane 12) and 2-aminopurine (FIG. 14, lane 26; FIG. 11, lane 13). Both were incorporated in CS13 mutant but formed only short polymers.

For the modified nucleotides that were weakly incorporated by CS13 mutants (FANA, 5-ethynyl-UTP, 5-methyl-UTP, Ara-NTP) different reaction conditions (buffer, metal ions, pH) and other mutants like Y2387F (NM11) can be tested that can widen substrate specificity depending on their modifications. DW9 mutant (L2334M-E2335G) has been already tested with the same panel of modified nucleotides but showed the same behavior as CS13 mutant. Moreover, hypotheses of inventors explaining how CS13 mutant accept well ribonucleotides and some modified nucleotides are based on a structural model where ddATP was replaced by ATP and the glutamate residue was just replaced by glycine. To corroborate this model, the crystal structure of the mutant CS13 can be performed so to visualize the spatial rearrangements of the nucleotide binding pocket.

Similar results were observed for the DW9 mutant for the 2'-Amino, 2'-Fluoro and 2'-Azido nucleotides as longs polymers were formed (FIG. 15; respectively lanes 1-5, lanes 11-15 and lanes 16-20). Otherwise, an enhanced incorporation of 2'-O-methyl was observed with the DW9 mutant compared to CS13 mutant (FIG. 15; lanes 6-10). In addition, a better incorporation of epsilon-ATP (FIG. 15; lane 23), can be noticed compared to CS13 mutant while DW9 failed to incorporate Ara-ATP and Ara-CTP nucleotides (lanes 21 and 22).

Building RNA Aptamer Libraries For SELEX

Human pol theta (pol θ)-CS13 and DW9 mutants demonstrated reliable ability to perform RNA random synthesis and to incorporate a large panel of modified nucleotides. The processivity and the randomness of its activity have been assessed quantitatively and this new enzymatic machinery should be useful for therapeutics applications. In that way, the continuous quest for ultra-effective, selective and non-toxic nucleic acids-based drugs remains the driving force of aptamer design strategies. This work offers a viable biological alternative to the generation of RNA random sequences by chemical synthesis and library design. By establishing an efficient enzymatic SELEX procedure, the assay costs will be reduced at the same time as the duration of the selection cycle. The resulted pool of RNAs obtained with CS13 and DW9 mutants served as starting candidates for aptamer library. For that purpose, a fixed fragment of RNA was added to the end of each synthesized RNA. This fragment can serve as matrix strand to amplify the selected aptamer after each cycle of SELEX. The inventors decided to implement a ligation of the fixed fragment to each synthesized RNA by exploiting T4 RNA ligase I activity. The results show that the ligation of these fixed oligonucleotides occurs (FIG. 13), thus demonstrating that it is possible to add a constant region to the synthetic RNA pool and that the RNA library can hence be screened or amplified for different applications, in particular for aptamer selection.

Mutant DNA Polymerases of the Pol Theta Family

The invention relates to mutant DNA polymerases of the Pol theta subfamily capable of performing non-templated nucleic acid extension, or of a functional (i.e., capable of performing non-templated nucleic acid extension) fragment of such a polymerase, methods of producing these mutant DNA polymerases, and uses and methods of using these mutant DNA polymerases.

The term "DNA polymerase theta" or "pol theta" or "pol θ" refers to a protein encoded by the POLQ gene in mammalian genome. This low-fidelity DNA polymerase is involved in a DSB (Double Strand Breaks) repair pathway termed "alternative End-joining" (alt-EJ) of "Theta-mediated end-joining". This pathway is characterized by the joining of the 3' single-stranded DNA tails which occurs when a DNA break cannot be efficiently repaired by Ku-dependent non-homologous end joining[40]. The polymerase is able to efficiently replicate through an abasic site by functioning both as a mispair inserter and as a mispair extender[41]. DNA polymerase theta has a characteristic C-terminal DNA polymerase domain linked via a central region to a N-terminal DNA-helicase-like domain[28,42]. Pol theta has the ability to switch templates and prime from homologies but also it can extent some single-stranded DNA substrates[43,44]. When manganese cations ($Mn^{2+}$) are present is physiological concentrations pol theta does not have template-independent terminal transferase activity[28] whereas with high ratios of $Mn^{2+}$ aver $Mg^{2+}$ the polymerase appears to trigger template-independent extension. $Mn^{2+}$ ions have been shown to relax template specificity in many polymerases[45]. Representative examples of pol theta include without limitation, human (Gene ID.10721), rat (Gene ID. 288079), chicken (Gene ID.418326), canine (Gene ID.488003), Zebrafish (Gene ID. 566079), Fruit fly mus308 (Gene ID. 41571) and mouse (Gene ID. 77782) forms.

In various embodiments, the mutant DNA polymerase theta (Pol theta) or a functional fragment thereof comprises at least one amino acid substitution at a position selected from the group consisting of: 2322, 2328, 2334, 2335, 2384, 2387 and 2391, the indicated positions being determined by alignment with SEQ ID NO: 1.

In various embodiments, the mutant DNA polymerase theta (Pol theta) or a functional fragment thereof comprises at least one amino acid substitution selected from the group consisting of: a Proline (P) to an aliphatic amino acid or a polar amino acid substitution at position 2322, an Alanine (A) to an aliphatic amino acid or a polar amino acid substitution at position 2328, a Leucine (L) to an aliphatic amino acid substitution at position 2334, a Glutamic acid (E) to an aliphatic amino acid or a polar amino acid substitution at position 2335, a Glutamine (Q) to an aliphatic amino acid or a polar amino acid substitution at position 2384, a Tyrosine (Y) to an aromatic amino acid or an aliphatic amino acid substitution at position 2387, and a Tyrosine (Y) to an aromatic amino acid or an aliphatic amino acid substitution at position 2391, the indicated positions being determined by alignment with SEQ ID NO: 1.

In various embodiments, the mutant DNA polymerase theta (Pol theta) or a functional fragment thereof comprises at least one amino acid substitution at position 2322, wherein the amino acid at position 2322 is substituted by an aliphatic amino acid selected from the group consisting of: Valine (V) and Alanine (A), the indicated position being determined by alignment with SEQ ID NO: 1.

In various embodiments, the mutant DNA polymerase theta (Pol theta) or a functional fragment thereof comprises at least one amino acid substitution at position 2322, wherein the amino acid at position 2322 is substituted by a polar amino acid selected from the group consisting of: Threonine (T) and Serine (S), the indicated position being determined by alignment with SEQ ID NO: 1.

In various embodiments, the mutant DNA polymerase theta (Pol theta) or a functional fragment thereof comprises at least one amino acid substitution at position 2328, wherein the amino acid at position 2328 is substituted by an aliphatic amino acid selected from the group consisting of: Valine (V) and Glycine (G), the indicated position being determined by alignment with SEQ ID NO: 1.

In various embodiments, the mutant DNA polymerase theta (Pol theta) or a functional fragment thereof comprises at least one amino acid substitution at position 2328, wherein the amino acid at position 2328 is substituted by a polar amino acid selected from the group consisting of: Threonine (T) and Serine (S), the indicated position being determined by alignment with SEQ ID NO: 1.

In various embodiments, the mutant DNA polymerase theta (Pol theta) or a functional fragment thereof comprises at least one amino acid substitution at position 2334, wherein the amino acid at position 2334 is substituted by an aliphatic amino acid selected from the group consisting of: Methionine (M), Isoleucine (I) and Alanine (A), the indicated position being determined by alignment with SEQ ID NO: 1.

In various embodiments, the mutant DNA polymerase theta (Pol theta) or a functional fragment thereof comprises at least one amino acid substitution at position 2335, wherein the amino acid at position 2335 is substituted by an aliphatic amino acid selected from the group consisting of: Glycine (G) and Alanine (A), the indicated position being determined by alignment with SEQ ID NO: 1.

In various embodiments, the mutant DNA polymerase theta (Pol theta) or a functional fragment thereof comprises at least one amino acid substitution at position 2335, wherein the amino acid at position 2335 is substituted by a polar amino acid selected from the group consisting of: Threonine (T) and Serine (S), the indicated position being determined by alignment with SEQ ID NO: 1.

In various embodiments, the mutant DNA polymerase theta (Pol theta) or a functional fragment thereof comprises at least two amino acid substitutions at positions 2334 and 2335, the indicated position being determined by alignment with SEQ ID NO: 1. In various embodiments, the amino acid at position 2334 is substituted by an amino acid selected from the group consisting of: Methionine (M), Isoleucine (I) and Alanine (A), and preferably by a Methionine (M). In some embodiments, the amino acid at position 2335 is substituted by an amino acid selected from the group consisting of: Glycine (G), Alanine (A), Threonine (T) and Serine (S), and preferably by a Glycine (G).

In various embodiments, the mutant DNA polymerase theta (Pol theta) or a functional fragment thereof comprises at least one amino acid substitution at position 2384, wherein the amino acid at position 2384 is substituted by an Alanine (A), the indicated position being determined by alignment with SEQ ID NO: 1.

In various embodiments, the mutant DNA polymerase theta (Pol theta) or a functional fragment thereof comprises at least one amino acid substitution at position 2384, wherein the amino acid at position 2384 is substituted by a polar amino acid selected from the group consisting of: Asparagine (N), Serine (S) and Threonine (T), the indicated position being determined by alignment with SEQ ID NO: 1

In various embodiments, the mutant DNA polymerase theta (Pol theta) or a functional fragment thereof comprises at least one amino acid substitution at position 2387, wherein the amino acid at position 2387 is substituted by an aromatic amino acid selected from the group consisting of: Phenylalanine (F) and Tryptophan (W), the indicated position being determined by alignment with SEQ ID NO: 1.

In various embodiments, the mutant DNA polymerase theta (Pol theta) or a functional fragment thereof comprises at least one amino acid substitution at position 2387, wherein the amino acid at position 2387 is substituted by an aliphatic amino acid selected from the group consisting of: Alanine (A) and Valine (V), the indicated position being determined by alignment with SEQ ID NO: 1.

In various embodiments, the mutant DNA polymerase theta (Pol theta) or a functional fragment thereof comprises at least one amino acid substitution at position 2391, wherein the amino acid at position 2391 is substituted by an aromatic amino acid selected from the group consisting of: Phenylalanine (F) and Tryptophan (W), the indicated position being determined by alignment with SEQ ID NO: 1.

In various embodiments, the mutant DNA polymerase theta (Pol theta) or a functional fragment thereof comprises at least one amino acid substitution at position 2391, wherein the amino acid at position 2391 is substituted by an aliphatic amino acid selected from the group consisting of: Alanine (A) and Valine (V), the indicated position being determined by alignment with SEQ ID NO: 1.

In various embodiments, the mutant DNA polymerase theta (Pol theta) or a functional fragment thereof comprises at least one amino acid substitution selected from the group consisting of: P to V substitution at position 2322 (P2322V), A to V substitution at position 2328 (A2328V), L to M substitution at position 2334 (L2334M), E to G substitution at position 2335 (E2335G), Q to N at position 2384 (Q2384N), Y to F substitution at position 2387 (Y2387F); and Y to F substitution at position 2391 (Y2391 F), the indicated positions being determined by alignment with SEQ ID NO: 1.

In various embodiments, the mutant DNA polymerase theta (Pol theta) or a functional fragment thereof comprises at least one amino acid substitution selected from the group consisting of: P to V substitution at position 2322 (P2322V), A to V substitution at position 2328 (A2328V), L to M substitution at position 2334 (L2334M), E to G substitution at position 2335 (E2335G), and Y to F substitution at position 2387 (Y2387F), the indicated positions being determined by alignment with SEQ ID NO: 1. In various embodiments, the mutant DNA polymerase theta (Pol theta) or a functional fragment thereof comprises a single amino acid substitution selected from the group consisting of: P to V substitution at position 2322 (P2322V), A to V substitution at position 2328 (A2328V), L to M substitution at position 2334 (L2334M), E to G substitution at position 2335 (E2335G), Q to N at position 2384 (Q2384N), Y to F substitution at position 2387 (Y2387F), and Y to F substitution at position 2391 (Y2391 F), the indicated positions being determined by alignment with SEQ ID NO: 1.

In various embodiments, the mutant DNA polymerase theta (Pol theta) or a functional fragment thereof comprises a double amino acid substitution L2334M and E2335G, the indicated positions being determined by alignment with SEQ ID NO: 1.

In various embodiments, the mutant DNA polymerase or a functional fragment thereof comprises at least one amino acid substitution selected from the group consisting of: P to V substitution at position 2322 (P2322V), A to V substitution at position 2328 (A2328V), L to M substitution at position 2334 (L2334M), E to G substitution at position 2335 (E2335G), and Y to F substitution at position 2387 (Y2387F), the indicated positions being determined by alignment with SEQ ID NO: 1. The terms "mutant" and "variant" may be used interchangeably and constitute the same meaning and purpose within the present invention. A mutant or a variant means a polypeptide derived from DNA polymerases of the pol theta subfamily, or derived from a functional fragment of such DNA polymerases, and in particular of a human DNA polymerase theta sequence according to the sequence SEQ ID NO: 1, and comprising at least one substitution, and having DNA polymerase and terminal nucleotidyltransferase activities. The variants can be obtained by various techniques well known in the art.

The term "substitution" means that the amino acid in the particular position has been replaced by another amino acid than that in wild-type (wt) DNA polymerase. Preferably, the term "substitution" refers to replacement of an amino acid residue with another selected from the 20 natural residues of standard amino acids, rare amino acid residues of natural origin (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine), and unnatural amino acid residues (e.g. norleucine, norvalin and cyclohexyl-alanine). Preferably, the term "substitution" refers to the replacement of an amino acid residue by another selected from the standard 20 amino acid residues. For example, a P to V substitution at position 2322 means the replacement of the proline (P) in position 2322 by a valine, the indicated position being determined by alignment with SEQ ID NO: 1.

The amino acids residues are represented by the one letter or three letter code according to the following nomenclature: A: Ala, alanine; C: Cys, cysteine; D: Asp, aspartic acid; E: Glu, glutamic acid; F: Phe, phenylalanine; G: Gly, glycine; H: His, histidine; I: Ile, isoleucine; K: Lys, lysine; L: Leu, leucine; M: Met, methionine; N: Asn, asparagine; P: Pro, proline; Q: Gln, glutamine; R: Arg, arginine; S: Ser, serine; T: Thr, threonine; V: Val, valine; W: Trp, tryptophan; Y: Tyr, tyrosine.

The term "aliphatic amino acid" refers to residues having side chain that contain only carbon or hydrogen atoms and remain inside proteins. Aliphatic amino acids group comprises the residues Glycine (G), Alanine (A), Valine (V), Leucine (L) and Isoleucine (I). Methionine residue can be considered as aliphatic amino acid although its side-chain contains a sulfur atom that is largely non-reactive, so that Methionine effectively substitutes well with the strictly aliphatic amino acids.

The term "polar amino acid" refers to residues having a polar group on their side chain. This allows these residues to form hydrogen bonds and covalent bonds to other substituents that may modify the protein structure. The residues Threonine (T), Serine (S), Cysteine (C), Proline (P), Asparagine (N) and Glutamine (Q) constitute the polar amino acids group.

The term "aromatic amino acid" refers to residues containing an aromatic ring. Generally, aromatic ring systems are planar, and electrons are shared over the whole ring structure. The aromatic amino acid group comprises Phenylalanine (F), Tryptophane (W) and Tyrosine (Y). By "comprises at least one substitution", it is meant that the mutant DNA polymerase has one or more amino acid substitutions as indicated with respect to the amino acid sequence SEQ ID NO: 1, but may have other modifications, including substitutions, deletions or additions of amino acid residues.

The mutant DNA polymerase can comprise 1, 2, 3, 4, 5, 6, 7 or all of the mutations listed above. All of these possible combinations are specifically contemplated.

Preferably, the mutant DNA polymerase is at least 1000, 1100, 1200, 1300, 1400, 1500, 1600, 1700, 1725, 1750, or 1775 amino acids in size. Preferably, the mutant contains at least 1, 2, 3, 4, 5, or 6 substitutions in the Finger subdomain (residues 2333-2474) or the full-length amino acid sequence of Human pol theta (pol θ), Mouse pol theta (pol θ), Zebrafish pol theta (pol θ), or Fruit fly mus308 pol theta (pol θ) or in a homologous pol theta (pol θ).

Preferably, the mutant is contained in the plasmids within the bacteria deposited as CNCM I-5238 (*E. coli* Δ1-1791_CS13); CNCM I-5239 (*E. coli* Δ1-1791_DW9); CNCM I-5240 (*E. coli* Δ1-1791_MC15); and CNCM I-5241 (*E. coli* Δ1-1791_NM11).

Preferably, the mutant contains at least 1, 2, 3, 4, 5, or 6 substitutions in the Finger subdomain (residues 2333-2474) or the full-length amino acid sequence of Human pol theta (pol θ), Mouse pol theta (pol θ), Rat pol theta (pol θ), Chicken pol theta (pol θ), Canine pol theta (pol θ), Zebrafish pol theta (pol θ), or Fruit fly mus308 pol theta (pol θ) or in a homologous pol theta (pol θ).

The term "homologous" refers to sequences that have sequence similarity. The term "sequence similarity", in all its grammatical forms, refers to the degree of identity or correspondence between nucleic acid or amino acid sequences. In the context of the invention, two amino acid sequences are "homologous" when at least 80%, alternatively at least 81%, alternatively at least 82%, alternatively at least 83%, alternatively at least 84%, alternatively at least 85%, alternatively at least 86%, alternatively at least 87%, alternatively at least 88%, alternatively at least 89%, alternatively at least 90%, alternatively at least 91%, alternatively at least 92%, alternatively at least 93%, alternatively at least 94%, alternatively at least 95%, alternatively at least 96%, alternatively at least 97%, alternatively at least 98%, alternatively at least 99% of the amino acids are identical to the Finger subdomain (residues 2333-2474) or the full-length amino acid sequence of Human pol theta (pol θ) (Gene ID. 10721), Mouse pol theta (pol θ) (Gene ID. 77782), Zebrafish pol theta (pol θ) (Gene ID. 566079), or Fruit fly mus308 pol theta (pol θ) (Gene ID. 41571).

Preferably, the mutant DNA polymerase has at least 70%, 75%, 80%, 85%, 90%, 95%, 97%, 98%, or 99% identity with the following amino acid sequence (SEQ ID NO:1):

```
   1  mnllrrsgkr rrsesgsdsf sgsggdssas pqflsgsvls pppglgrclk aaaageckpt
  61  vpdyerdkll lanwglpkav lekyhsfgvk kmfewqaecl llgqvlegkn lvysaptsag
 121  ktivaellil krvlemrkka lfilpfvsva kekkyylqsl fqevgikvdg ymgstspsrh
 181  fssldiavct ieranglinr lieenkmdll gmvvvdelhm lgdshrgyll ellltkicyi
 241  trksascqad lasslsnavq ivgmsatlpn lelvaswlna elyhtdfrpv pllesvkvgn
 301  siydssmklv refepmlqvk gdedhvvslc yeticdnhsv llfcpskkwc ekladiiare
 361  fynlhhqaeg lvkpsecppv ileqkellev mdqlrrlpsg ldsvlqktvp wgvafhhagl
 421  tfeerdiieg afrqglirvl aatstlssgv nlparrviir tpifggrpld iltykqmvgr
 481  agrkgvdtvg esilicknse kskgiallqg slkpvrsclq rregeevtgs miraileiiv
 541  ggvastsqdm htyaactfla asmkegkqgi qrnqesvqlg aieacvmwll enefiqstea
 601  sdgtegkvyh pthlgsatls sslspadtld ifadlqramk gfvlendlhi lylvtpmfed
 661  wttidwyrff clweklptsm krvaelvgve egflarcvkg kvvarterqh rqmaihkrff
 721  tslvlldlis evplreinqk ygcnrgqiqs lqqsaavyag mitvfsnrlg whnmelllsq
 781  fqkrltfgiq relcdlvrvs llnaqrarvl yasgfhtvad laraniveve vilknavpfk
 841  sarkavdeee eaveerrnmr tiwvtgrkgl tereaaaliv eearmilqqd lvemgvqwnp
 901  callhsstcs lthsesevke htfisqtkss ykkltsknks ntifsdsyik hspnivqdln
 961  ksrehtssfn cnfqngnqeh qtcsifrark rasldinkek pgasqnegkt sdkkvvqtfs
1021  qktkkaplnf nsekmsrsfr swkrrkhlkr srdssplkds gacrihlqgq tlsnpslced
1081  pftldekkte frnsgpfakn vslsgkekdn ktsfplqikq ncswnitltn dnfvehivtg
1141  sqsknvtcqa tsvvsekgrg vaveaekine vliqngsknq nvymkhhdih pinqylrkqs
1201  hegtstitkq kniierqmpc eayssyinrd snvtinceri klnteenkps hfqalgddis
1261  rtvipsevlp sagafskseg qhenflnisr lqektgtytt nktknnhvsd lglvlcdfed
1321  sfyldtqsek iiqqmatena klgakdtnla agimqkslvq qnsmnsfqke chipfpaeqh
1381  plgatkidhl dlktvgtmkq ssdshgvdil tpespifhsp illeenglfl kknevsvtds
```

```
1441  qlnsflqgyq tqetvkpvil lipqkrtptg vegeclpvpe tslnmsdsll fdsfsddylv 1501  keqlpdmqmk eplpsevtsn hfsdslclqe dlikksnvne nqdthqqltc sndesiifse 1561  mdsvqmveal dnvdifpvqe knhtvvspra lelsdpvlde hhqgdqdggd qderaekskl 1621  tgtrqnhsfi wsgasfdlsp glqrildkvs spleneklks mtinfsslnr kntelneeqe 1681  visnletkqv qgisfssnne vkskiemlen nanhdetssl lprkesnivd dnglipptpi 1741  ptsaskltfp giletpvnpw ktnnvlqpge sylfgspsdi knhdlspgsr ngfkdnspis 1801  dtsfslqlsq dglqltpass sseslsiidv asdqnlfqtf ikewrckkrf sislacekir 1861  sltssktati gsrfkqassp qeipirddgf pikgcddtlv vglavcwggr dayyfslqke 1921  qkhseisasl vppsldpslt lkdrmwylqs clrkesdkec svviydfiqs ykilllscgi 1981  sleqsyedpk vacwlldpds qeptlhsivt sflphelpll egmetsqgiq slglnagseh 2041  sgryrasves ilifnsmnql nsllqkenlq dvfrkvemps qyclalleln gigfstaece 2101  sqkhimqakl daietqayql aghsfsftss ddiaevlfle lklppnremk nqgskktlgs 2161  trrgidngrk lrlgrqfsts kdvlnklkal hplpglilew rritnaitkv vfplqrekcl 2221  npflgmeriy pvsqshtatg ritftepniq nvprdfeikm ptlvgespps qavgkgllpm 2281  grgkykkgfs vnprcqaqme eraadrgmpf sismrhafvp fpggsilaad ysqlelrila 2341  hlshdrrliq vintgadvfr siaaewkmie pesvgddlrq qakqicygii ygmgakslge 2401  qmgikendaa cyidsfksry tginqfmtet vknckrdgfv qtilgrrryl pgikdnnpyr 2461  kahaerqain tivqgsaadi vkiatvniqk qletfhstfk shghregmlq sdqtglsrkr 2521  klqgmfcpir ggffilqlhd ellyevaeed vvqvaqivkn emesavklsv klkvkvkiga 2581  swgelkdfdv.
```

Mutants, homologues, functional fragments of DNA polymerases of the Pol theta family can be made by routine techniques in the art and screened for activity (i.e., capable of performing non-templated nucleic acid extension) using the assays described herein or other similar assays.

Nucleic Acids, Vectors and Cells

In various embodiments, the invention encompasses nucleic acids comprising a nucleotide sequence encoding the mutant DNA polymerase of the invention or a functional fragment thereof, a vector comprising these nucleic acids, and a host cell comprising these vectors. Nucleic acids include DNA, RNA, and modified nucleic acids.

The term "vector" herein means the vehicle by which a heterologous (e.g., mutant or synthetic) DNA or RNA sequence of can be introduced into a host cell so as to transform it and promote expression of the introduced sequence. Preferably, the vector is a DNA vector. Vectors may include for example, plasmids, phages, and viruses and are discussed in greater detail below. Indeed, any type of plasmid, cosmid, YAC or viral vector may be used to prepare a recombinant nucleic acid construct. For example, viral vectors, such as lentiviruses, retroviruses, herpes viruses, adenoviruses, adeno-associated viruses, vaccinia virus, baculovirus, and other recombinant viruses with desirable cellular tropism. Methods for constructing and using viral vectors are known in the art (see, Miller and Rosman, *BioTechniques*, 7:980-990, 1992).

For non-vertebrate cells, preferred vectors are the arboviruses, the West Nile virus being particularly preferred, which are arthropod vectors. Other vectors that are known to efficiently be expressed in non-vertebrate cells are the baculoviruses.

For vertebrate cells, lentiviral, AAV, baculoviral and adenoviral vectors are preferred. The vectors suited for expression in mammalian host cells can also be of non viral (e.g. plasmid DNA) origin. Suitable plasmid vectors include, without limitation, pREP4, pCEP4 (Invitrogene), pCI (Promega), pCDM8 and pMT2PC, pVAX and pgWiz.

For prokaryote cells, plasmid, bacteriophage and cosmid vectors are preferred. Suitable vectors for use in prokaryote systems include without limitation pBR322 (Gibco BRL), pUC (Gibco BRL), pBluescript (Stratagene), p Poly, pTrc; pET 11d; pIN; and pGEX vectors.

For plant cells, plasmid expression vectors such as Ti plasmids, and virus expression vectors such as Cauliflower mosaic virus (CaMV) and tobacco mosaic virus TMV are preferred.

Expression of recombinant proteins in yeast cells can be done using three types of vectors: integration vectors (YIp), episomal plasmids (YEp), and centromeric plasmids (YCp): Suitable vectors for expression in yeast (e.g. *S. cerevisiae*) include, but are not limited to pYepSec1, pMFa, pJRY88, pYES2 (Invitrogen Corporation, San Diego, Calif.) and pTEF-MF (Dualsystems Biotech Product code: P03303).

A sequence "encoding" an expression product, such as a RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

In the context of the present invention, "host" cells are any cells which can be used for producing recombinant proteins, such as "non-vertebrate" (or invertebrate) cells, vertebrate cells, plant cells, yeast cells, or prokaryote cells. They are preferably non-vertebrate and vertebrate cells.

Non-vertebrate (also known as invertebrate) comprises different phyla, the most famous being the Insect, Arachnida, Crustacea, Mollusca, Annelida, Cirripedia, Radiata, Coelenterata and Infusoria. They are now classified into over 30 phyla, from simple organisms such as sea sponges and flatworms to complex animals such as arthropods and molluscs. In the context of the invention, non-vertebrate cells are preferably insect cells, such as *Drosophila* or Mosquito cells, more preferably *Drosophila* S2 cells.

Examples of cells derived from vertebrate organisms that are useful as host cell lines include non-human embryonic stem cells or derivative thereof, for example avian EBX cells; monkey kidney CVI line transformed by SV40 sequences (COS-7, ATCC CRL 1651); a human embryonic kidney line (293); baby hamster kidney cells (BHK, ATCC CCL 10); Chinese hamster ovary cells (CHO); mouse sertoli cells (TM4); monkey kidney cells (CVI, ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442);

human lung cells (W138, ATCC CCL 75); human liver cells (Hep G2, HB 8065); mouse mammary tumor cells (MMT 060562, ATCC CCL51); rat hepatoma cells (HTC, MI.5); YB2/O (ATCC n° CRL1662); NIH3T3; HEK and TRI cells. In the context of the invention, vertebrate cells are preferably EBX, CHO, YB2/O, COS, HEK, NIH3T3 cells or derivatives thereof.

Plant cells which can be used in the context of the invention are the tobacco cultivars Bright Yellow 2 (BY2) and *Nicotiana Tabaccum* 1 (NT-1).

Yeast cells which can be used in the context of the invention are: *Saccharomyces cerevisiae, Schizosaccharomyces pombe*, and *Hansenula polymorpha*, as well as methylotropic yeasts like *Pichia pastoris* and *Pichia methanolica*.

Prokaryote cells which can be used in the context of the invention are typically *E. Coli* bacteria or *Bacillus Subtilis* bacteria.

In various embodiments, the host cell of the invention is the host cell deposited at the Collection Nationale de Cultures de Microorganismes (CNCM) at the Institut Pasteur, 25, Rue du Docteur Roux, 75724 Paris, FR, on Sep. 14, 2017 under the deposit number CNCM I-5238 (*E. coli* Δ1-1791_CS13).

In various embodiments, the host cell of the invention is the host cell deposited at the Collection Nationale de Cultures de Microorganismes (CNCM) at the Institut Pasteur, 25, Rue du Docteur Roux, 75724 Paris, FR, on Sep. 14, 2017 under the deposit number CNCM I-5239 (*E. coli* Δ1-1791_DW9).

In various embodiments, the host cell of the invention is the host cell deposited at the Collection Nationale de Cultures de Microorganismes (CNCM) at the Institut Pasteur, 25, Rue du Docteur Roux, 75724 Paris, FR, on Sep. 14, 2017 under the deposit number CNCM I-5240 (*E. coli* Δ1-1791_MC15).

In various embodiments, the host cell of the invention is the host cell deposited at the Collection Nationale de Cultures de Microorganismes (CNCM) at the Institut Pasteur, 25, Rue du Docteur Roux, 75724 Paris, FR, on Sep. 14, 2017 under the deposit number CNCM I-5241 (*E. coli* Δ1-1791_NM11).

In various embodiments, the invention encompasses the use of the nucleic acids, vectors, and host cells of the invention for producing a mutant DNA polymerase.

Methods For Producing Mutant DNA Polymerases

In various embodiments, the invention encompasses a method for generating a mutant DNA polymerase of the Pol theta subfamily or a functional fragment thereof comprising substituting at least one amino acid in a DNA polymerase of the Pol theta family at a position selected from the group consisting of: 2322, 2328, 2334, 2335, 2384, 2387 and 2391, the indicated positions being determined by alignment with SEQ ID NO: 1.

In various embodiments, the invention encompasses a method for generating a mutant DNA polymerase of the Pol theta subfamily comprising substituting at least one amino acid in a DNA polymerase of the Pol theta subfamily, wherein the at least one substitution is selected from the group consisting of: a Proline (P) to an aliphatic amino acid or a polar amino acid substitution at position 2322, an Alanine (A) to an aliphatic amino acid or a polar amino acid substitution at position 2328, a Leucine (L) to an aliphatic amino acid substitution at position 2334, a Glutamic acid (E) to an aliphatic amino acid or a polar amino acid substitution at position 2335, a Glutamine (Q) to an aliphatic amino acid or a polar amino acid substitution at position 2384, a Tyrosine (Y) to an aromatic amino acid or an aliphatic amino acid substitution at position 2387, and a Tyrosine (Y) to an aromatic amino acid or an aliphatic amino acid substitution at position 2391, the indicated positions being determined by alignment with SEQ ID NO: 1.

In various embodiments, the invention encompasses a method for generating a mutant DNA polymerase of the Pol theta subfamily comprising substituting at least one amino acid at position 2322 in a DNA polymerase of the Pol theta subfamily, wherein the amino acid at position 2322 is substituted by an aliphatic amino acid selected from the group consisting of: Valine (V) and Alanine (A), the indicated position being determined by alignment with SEQ ID NO: 1.

In various embodiments, the invention encompasses a method for generating a mutant DNA polymerase of the Pol theta subfamily comprising substituting at least one amino acid at position 2322 in a DNA polymerase of the Pol theta subfamily, wherein the amino acid at position 2322 is substituted by a polar amino acid selected from the group consisting of: Threonine (T) and Serine (S), the indicated position being determined by alignment with SEQ ID NO: 1.

In various embodiments, the invention encompasses a method for generating a mutant DNA polymerase of the Pol theta subfamily comprising substituting at least one amino acid at position 2328 in a DNA polymerase of the Pol theta subfamily, wherein the amino acid at position 2328 is substituted by an aliphatic amino acid selected from the group consisting of: Valine (V) and Glycine (G), the indicated position being determined by alignment with SEQ ID NO: 1.

In various embodiments, the invention encompasses a method for generating a mutant DNA polymerase of the Pol theta subfamily comprising substituting at least one amino acid at position 2328 in a DNA polymerase of the Pol theta subfamily, wherein the amino acid at position 2328 is substituted by a polar amino acid selected from the group consisting of: Threonine (T) and Serine (S), the indicated position being determined by alignment with SEQ ID NO: 1.

In various embodiments, the invention encompasses a method for generating a mutant DNA polymerase of the Pol theta subfamily comprising substituting at least one amino acid at position 2334 in a DNA polymerase of the Pol theta subfamily, wherein the amino acid at position 2334 is substituted by an aliphatic amino acid selected from the group consisting of: Methionine (M), Isoleucine (I) and Alanine (A), the indicated position being determined by alignment with SEQ ID NO: 1.

In various embodiments, the invention encompasses a method for generating a mutant DNA polymerase of the Pol theta subfamily comprising substituting at least one amino acid at position 2335 in a DNA polymerase of the Pol theta subfamily, wherein the amino acid at position 2335 is substituted by an aliphatic amino acid selected from the group consisting of: Glycine (G) and Alanine (A), the indicated position being determined by alignment with SEQ ID NO: 1.

In various embodiments, the invention encompasses a method for generating a mutant DNA polymerase of the Pol theta subfamily comprising substituting at least one amino acid at position 2335 in a DNA polymerase of the Pol theta subfamily, wherein the amino acid at position 2335 is substituted by a polar amino acid selected from the group consisting of: Threonine (T) and Serine (S), the indicated position being determined by alignment with SEQ ID NO: 1.

In various embodiments, the invention encompasses a method for generating a mutant DNA polymerase of the Pol theta subfamily comprising substituting at least two amino acids at positions 2334 and 2335 in a DNA polymerase of the Pol theta subfamily. In various embodiments, the amino acid at position 2334 is substituted by an amino acid selected from the group consisting of: Methionine (M), Isoleucine (I) and Alanine (A), and preferably by a Methionine (M), In some embodiments, the amino acid at position 2335 is substituted by an amino acid selected from the group consisting of: Glycine (G), Alanine (A), Threonine (T) and Serine (S), and preferably by a Glycine (G).

In various embodiments, the invention encompasses a method for generating a mutant DNA polymerase of the Pol theta subfamily comprising substituting at least one amino acid at position 2384 in a DNA polymerase of the Pol theta subfamily, wherein the amino acid at position 2384 is substituted by an Alanine (A), the indicated position being determined by alignment with SEQ ID NO: 1.

In various embodiments, the invention encompasses a method for generating a mutant DNA polymerase of the Pol theta subfamily comprising substituting at least one amino acid at position 2384 in a DNA polymerase of the Pol theta subfamily, wherein the amino acid at position 2384 is substituted by a polar amino acid selected from the group consisting of: Asparagine (N), Serine (S) and Threonine (T), the indicated position being determined by alignment with SEQ ID NO: 1

In various embodiments, the invention encompasses a method for generating a mutant DNA polymerase of the Pol theta subfamily comprising substituting at least one amino acid at position 2387 in a DNA polymerase of the Pol theta subfamily, wherein the amino acid at position 2387 is substituted by an aromatic amino acid selected from the group consisting of: Phenylalanine (F) and Tryptophan (W), the indicated position being determined by alignment with SEQ ID NO: 1.

In various embodiments, the invention encompasses a method for generating a mutant DNA polymerase of the Pol theta subfamily comprising substituting at least one amino acid at position 2387 in a DNA polymerase of the Pol theta subfamily, wherein the amino acid at position 2387 is substituted by an aliphatic amino acid selected from the group consisting of: Alanine (A) and Valine (V), the indicated position being determined by alignment with SEQ ID NO: 1.

In various embodiments, the invention encompasses a method for generating a mutant DNA polymerase of the Pol theta subfamily comprising substituting at least one amino acid at position 2391 in a DNA polymerase of the Pol theta subfamily, wherein the amino acid at position 2391 is substituted by an aromatic amino acid selected from the group consisting of: Phenylalanine (F) and Tryptophan (W), the indicated position being determined by alignment with SEQ ID NO: 1.

In various embodiments, the invention encompasses a method for generating a mutant DNA polymerase of the Pol theta subfamily comprising substituting at least one amino acid at position 2391 in a DNA polymerase of the Pol theta subfamily, wherein the amino acid at position 2391 is substituted by an aliphatic amino acid selected from the group consisting of: Alanine (A) and Valine (V), the indicated position being determined by alignment with SEQ ID NO: 1.

In various embodiments, the invention encompasses a method for generating a mutant DNA polymerase of the Pol theta subfamily comprising substituting at least one amino acid in a DNA polymerase of the Pol theta subfamily, wherein the at least one substitution is selected from the group consisting of: P to V substitution at position 2322 (P2322V), A to V substitution at position 2328 (A2328V), L to M substitution at position 2334 (L2334M), E to G substitution at position 2335 (E2335G), Q to N at position 2384 (Q2384N), Y to F substitution at position 2387 (Y2387F); and Y to F substitution at position 2391 (Y2391F), the indicated positions being determined by alignment with SEQ ID NO: 1.

In various embodiments, the invention encompasses a method for generating a mutant DNA polymerase of the Pol theta subfamily comprising substituting at least one amino acid in a DNA polymerase of the Pol theta subfamily, wherein the at least one substitution is selected from the group consisting of: P to V substitution at position 2322 (P2322V), A to V substitution at position 2328 (A2328V), L to M substitution at position 2334 (L2334M), E to G substitution at position 2335 (E2335G), and Y to F substitution at position 2387 (Y2387F), the indicated positions being determined by alignment with SEQ ID NO: 1.

In various embodiments, the invention encompasses a method for generating a mutant DNA polymerase of the Pol theta subfamily comprising substituting a single amino acid in a DNA polymerase of the Pol theta subfamily, wherein the single amino acid substitution is selected from the group consisting of: P to V substitution at position 2322 (P2322V), A to V substitution at position 2328 (A2328V), L to M substitution at position 2334 (L2334M), E to G substitution at position 2335 (E2335G), Q to N at position 2384 (Q2384N), Y to F substitution at position 2387 (Y2387F), and Y to F substitution at position 2391 (Y2391F), the indicated positions being determined by alignment with SEQ ID NO: 1.

In various embodiments, the invention encompasses a method for generating a mutant DNA polymerase of the Pol theta subfamily comprising substituting the double amino acid substitution L2334M and E2335G, the indicated positions being determined by alignment with SEQ ID NO: 1.

In various embodiments, the invention encompasses a method for generating a mutant DNA polymerase of the Pol theta subfamily comprising substituting at least one amino acid in a DNA polymerase of the Pol theta subfamily, wherein the at least one substitution is selected from the group consisting of: P to V substitution at position 2322 (P2322V), A to V substitution at position 2328 (A2328V), L to M substitution at position 2334 (L2334M), E to G substitution at position 2335 (E2335G), and Y to F substitution at position 2387 (Y2387F); and E to G substitution at position 2335

(E2335G), the indicated positions being determined by alignment with SEQ ID NO: 1.

These substitutions can be made using routine methods known in the art, such as those described in the Examples. Preferably, the substitutions are made relative to a nucleic acid having all or part of the DNA sequence encoding Human pol theta (pol θ), Mouse pol theta (pol θ), Zebrafish pol theta (pol θ), or Fruit fly mus308 pol theta (pol θ) or a homologous pol theta (pol θ). Preferably, the DNA polymerase has at least 70%, 75%, 80%, 85%, 90%, 95%, 97%, 98%, 99%, or 100% identity with the amino acid sequence of SEQ ID NO:1. The nucleic acid can be at least 200, 300, 400, 500, 600, 700, 800, 900, 1000, 2000, 3000, 4000, or 5000 etc. nucleotides in size and may correspond to the Finger subdomain (residues 2333-2474) or the full-length amino acid sequence.

In a preferred embodiment, the mutant is made starting with DNA polymerase having at least 70%, 75%, 80%, 85%, 90%, 95%, 97%, 98%, 99%, or 100% identity with the amino acid sequence of SEQ ID NO:1 and substituting amino acids within this DNA polymerase.

In various embodiments, the invention encompasses a method for producing a mutant DNA polymerase culturing the host cell of the invention under culture conditions allowing expression of the polynucleotide encoding said mutant, and optionally recovering said mutant thus expressed from the medium culture or host cells.

Methods For Incorporating Nucleotides

The term "about" refers to a measurable value such as an amount, a temporal duration, a temperature and the like, and is meant to encompass non-limiting variations of +/−40% or +/−20% or +/−10% or +/−5% or +/−1% or +/−0.1% from the specified value, as such variations are appropriate.

In one embodiment, the invention encompasses a method for incorporating nucleotides in a template-free manner comprising incubating the mutant DNA polymerase of the invention, or a functional fragment thereof, with nucleotide triphosphates under conditions that allow nucleotide incorporation in the absence of a template.

In various embodiments, the mutant DNA polymerase or a functional fragment thereof is at a concentration of about 0.5 µM to about 50 µM, preferably at a concentration of about 1 µM to about 30 µM, preferably at a concentration of about 2 µM to about 10 µM, and preferably at a concentration of about 5 µM.

In various embodiments, the mutant DNA polymerase or a functional fragment thereof is incubated in presence of at least one divalent metal. In one embodiment, the divalent metal is manganese ($Mn^{2+}$), cobalt ($Co^{2+}$), magnesium ($Mg^{2+}$) or a combination thereof. In some embodiments, the divalent metal is manganese ($Mn^{2+}$), magnesium ($Mg^{2+}$) or a combination thereof. In some embodiments, the divalent metal is at a concentration of about 1 mM to about 50 mM. In some embodiments, the divalent metal is at a concentration of about 5 mM. Similarly, in one embodiment, the invention encompasses the use the mutant DNA polymerase of the invention or a functional fragment thereof for incorporating nucleotides in a template-free manner. Exemplary conditions are set forth in the Examples.

In various embodiments, the mutant DNA polymerase or a functional fragment thereof is incubated in presence of sodium chloride (NaCl) at a concentration of about 50 mM to about 300 mM, and preferably at a concentration of about 150 mM.

In various embodiments, the mutant DNA polymerase or a functional fragment thereof is incubated in presence of 5 mM $Mn^{2+}$, 20 mM Tris/HCl pH 8, 10% glycerol, 150 mM NaCl, 0.01% IGEPAL C6-30, 0.1 mg.ml$^{-1}$ BSA (Bovine Serum Albumine). In various embodiments, the incubation is at least 1 minute for generating a 20-30 nucleotides fragment.

In various embodiments, the incubation is performed at a temperature of about 25° C. to 50° C., preferably at a temperature of about 42° C.

The nucleotides can be natural deoxy-ribonucleotides, natural ribonucleotides, modified nucleotides or any combination of natural nucleotides and modified nucleotides. In some embodiments the deoxy-ribonucleotide is dATP, dGTP, dCTP, dTTP, or dUTP. In some embodiments the ribonucleotide is ATP, GTP, CTP, or UTP. In certain non-limiting embodiments, the modified nucleotide may be:

cy3-dUTP, Digoxigenin-I I-dUTP, Biotin-16AA-dUTP, Texas Red-5-dCTP, Cyanine 3-AA-UTP, 4-Thio-UTP, Biotin-16-AA-dCTP, Ganciclovir Triphosphate, N6-(6-Azido) hexyl-adenosine-5'-triphosphate, 5-Hydroxymethyl-2'-deoxyuridine-5'-Triphosphate;

2' modified nucleotides: 2'-Fluoro-dNTP: 2'-Fluoro-dUTP, 2'-Fluoro-dATP, 2'-Fluoro-dCTP, 2'-Fluoro-dGTP, 2'-Fluoro-dTTP; 2'-amino-dNTP: 2'-Amino-dATP, 2'-Amino-dTTP, 2'-Amino-dCTP, 2'-Amino-dGTP and 2'-Amino-dUTP; preferably, 2'-Amino-dATP or 2'-Amino-dGTP; 2'-O-methyl-dNTP: 2'-O-methyl-dATP, 2'-O-methyl-dUTP, 2'-O-methyl-dCTP, 2'-O-methyl-dGTP; 2'-N3-dNTP: 2'-azido-2'-dATP, 2'-azido-2'-dUTP, 2'-azido-2'-dCTP, 2'-azido-2'-dGTP; 2'-O-methyl-ATP and 2'-O-methyl-CTP;

Sugar modified nucleotides: Ara-ATP (Vidarabine triphosphate), Ara-CTP (Cytarabine triphosphate), and FANA;

Base modified nucleotides: 5-methyl-UTP, Etheno-ATP, 2-Aminopurine, and 5-ethynyl-UTP; and 3'-modified nucleotides: 3'-azido-ddATP, 3'-azido-ddCTP, 3'-O-methyl-ATP, 3'-O-methyl-CTP, 3'-O-(2-nitrobenzyl)-2'-dATP, 3'-O—NH$_2$-dATP, 3'-O—NH$_2$-dTTP, 3'-O—NH$_2$-dCTP and 3'-O—NH$_2$-dGTP and others. Other 3'-modified nucleotides include in particular reversible terminators and irreversible terminators. Such types of terminators are well-known in the art. Reversible terminators include for example 3'-O-azidomethyl nucleotides (Palla et al., RSC ADV., 2014, 4, 49342-) and 3'-(2-nitro-benzyl) nucleotides. Irreversible terminators include for example 3'-O-methyl dNTPs, Preferred modified nucleotides include: 2'-Fluoro-dUTP, 2'-Fluoro-dATP, 2'-Fluoro-dCTP, 2'-Fluoro-dGTP, 2'-Fluoro-dTTP, 2'-Amino-dATP, 5-methyl-UTP, Ara-ATP (Vidarabine triphosphate), Ara-CTP (Cytarabine triphosphate), 2'-O-methyl-ATP, 2'-O-methyl-CTP, Etheno-ATP, 2-Aminopurine, FANA, and 5-ethynyl-UTP.

In various embodiments, the invention encompasses a method for producing degenerate or random nucleotide sequences comprising incubating the mutant DNA polymerase of the invention or a functional fragment thereof with nucleotide triphosphates under conditions that allow degenerate or random nucleotide incorporation to produce degenerate or random nucleotide sequences. Exemplary conditions are set forth in the Examples.

In various embodiments, the mutant DNA polymerase or a functional fragment thereof is at a concentration of about 0.5 µM to about 50 µM, preferably at a concentration of about 1 µM to about 30 µM, preferably at a concentration of about 2 µM to about 10 µM, and preferably at a concentration of about 5 µM.

In various embodiments, the mutant DNA polymerase or a functional fragment thereof is incubated in presence of at least one divalent metal. In one embodiment, the divalent metal is manganese (Mn2+), cobalt (Co2+), magnesium (Mg2+) or a combination thereof. In some embodiments, the divalent metal is manganese (Mn2+), magnesium (Mg2+) or a combination thereof. In some embodiments, the divalent metal is at a concentration of about 1 mM to about 50 mM. In some embodiments, the divalent metal is at a concentration of about 5 mM.

In various embodiments, the mutant DNA polymerase or a functional fragment thereof is incubated in presence of sodium chloride (NaCl) at a concentration of about 50 mM to about 300 mM, and preferably at a concentration of about 150 mM.

In various embodiments, the mutant DNA polymerase or a functional fragment thereof is incubated in presence of 5 mM Mn2+, 20 mM Tris/HCl pH 8, 10% glycerol, 150 mM NaCl, 0.01% IGEPAL C6-30, 0.1 mg.ml-1 BSA (Bovine Serum Albumine).

In various embodiments, the incubation is at least 1 minute for generating a 20-30 nucleotides fragment.

In various embodiments, the incubation is performed at a temperature of about 25° C. to 50° C., preferably at a temperature of about 42° C.

The nucleotides can be natural deoxy-ribonucleotides, natural ribonucleotides, modified nucleotides or any combination of natural nucleotides and modified nucleotides. In some embodiments the deoxy-ribonucleotide is dATP, dGTP, dCTP, dTTP, or dUTP. In some embodiments the ribonucleotide is ATP, GTP, CTP, or UTP. In certain non-limiting embodiments, the modified nucleotide may be cy3-dUTP, Digoxigenin-I I-dUTP, Biotin-16AA-dUTP, Texas Red-5-dCTP, Cyanine 3-AA-UTP, 4-Thio-UTP, Biotin-16-AA-dCTP, Ganciclovir Triphosphate, N6-(6-Azido) hexyl-adenosine-5'-triphosphate, 5-Hydroxymethyl-2'-deoxyuridine-5'-Triphosphate, 2'-Fluoro-dUTP, 2'-Fluoro-dATP, 2'-Fluoro-dCTP, 2'-Fluoro-dGTP, 2'-Fluoro-dTTP, 2'-Amino-dATP, 2'-Amino-dTTP, 2'-Amino-dCTP, 2'-Amino-dGTP, 2'-Amino-dUTP; 2'-O-methyl-dUTP, 2'-O-methyl-dGTP, 2'-N3-dATP, 2'-N3dCTP, 2'-N3-dGTP, 2'-N3-dTTP, 2'-azido-2'-dATP, 2'-azido-2'-dUTP, 2'-azido-2'-dCTP, 2'-azido-2'-dGTP, 2'-O-methyl-ATP, 2'-O-methyl-CTP; 3'-azido-ddATP, 3'-azido-ddCTP, 3'-O-methyl-ATP, 3'-O-methyl-CTP, 3'-O-(2-nitrobenzyl)-2'-dATP, 3'-O—NH$_2$-dATP, 3'-O—NH$_2$-dTTP, 3'-O—NH$_2$-dCTP, 3'-O—NH$_2$-dGTP, 5-methyl-UTP, Ara-ATP (Vidarabine triphosphate), Ara-CTP (Cytarabine triphosphate), 2'-O-methyl-ATP, 2'-O-methyl-CTP, ε-ATP, 2-Aminopurine, FANA, and 5-ethynyl-UTP. Preferred modified nucleotides include: 2'-Fluoro-dUTP, 2'-Fluoro-dATP, 2'-Fluoro-dCTP, 2'-Fluoro-dGTP, 2'-Fluoro-dTTP, 2'-Amino-dATP, 2'-azido-2'-dATP, 2'-azido-2'-dUTP, 2'-azido-2'-dCTP, 2'-azido-2'-dGTP, 5-methyl-UTP, Ara-ATP (Vidarabine triphosphate), Ara-CTP (Cytarabine triphosphate), 2'-O-methyl-ATP, 2'-O-methyl-CTP, ε-ATP, 2-Aminopurine, FANA, 5-ethynyl-UTP, and reversible and irreversible 3'-modified nucleotide terminators as defined above. The degenerate or random nucleotides sequences can contain at least 0%, 10%, 20%, 30%, 40% or 50% molar ratio of natural deoxy-ribonucleotides or ribonucleotides.

In some embodiments, a fixed nucleotide sequence can be added to the 3' end of the degenerate or random nucleotide sequences. In some embodiments, the degenerate or random nucleotide sequences can be amplified. In some embodiments, the amplified sequences can be cloned into a vector to generate a library of degenerate or random nucleotide sequences.

Generation of Functional Nucleic Acids Libraries

In one embodiment, the invention encompasses use the mutant DNA polymerase of the invention or a functional fragment thereof for generating a functional nucleic acid library, and preferably an aptamer library.

In various embodiments, the invention encompasses a kit for generating a functional nucleic acid library, in particular an aptamer library comprising the mutant DNA polymerase of the invention or a functional fragment thereof. In some embodiments, the kit comprises reagents for degenerate or random nucleotide incorporation. In some embodiments, the kit comprises a vector for generating a library of degenerate or random nucleotide sequences.

Routinely, SELEX procedures comprise a step where the aptamer candidates are amplified before the next selection step. Since the newly synthesized RNAs do not have a fixed region at both ends, this region can be added enzymatically at the 3' end of each RNA fragment (the 5' end contains the constant known primer sequence).

In various embodiments, the use of ligation reaction[40] can be used for adding a 3' fixed region. For that purpose, commercial enzymes such as T4 RNA ligase I or RtcB ligase (from New England Biolabs) can be suitable. T4 RNA ligase I has been used in the example according to the commercial protocol.

In various embodiments, a fixed region can be added at the 3' end of each RNA fragment. The process for synthesizing the fixed region can be as described in the patent application WO2015/159023 (AU2015248673), which is hereby incorporated by reference.

To prepare a functional nucleic acid library, optionally an aptamer library, the functional nucleic acid candidates can be amplified, for example by PCR, before selection.

In various embodiments, the self-amplification step can be performed by using the mutant DNA polymerase theta of the present invention or a functional fragment thereof. By using the same enzyme, it would be possible to execute the entire SELEX procedure in an all-in-one system.

In various embodiments, the self-amplification step can be performed through one-pot isothermal reaction[41] by the Norovirus RNA replicase (NV3D$_{pol}$). The amplified nucleic acids can be inserted (i.e., cloned) into any vectors that could contain circularized DNA or RNA for the construction of a library. In some embodiments, a library of degenerate or random nucleotide sequences can be generated. The library can contain at least $10^5$, $10^6$, $10^7$, $10^8$, $10^9$, $10^{10}$, $10^{11}$, $10^{12}$, $10^{13}$, $10^{14}$, $10^{15}$, or $10^{16}$ different sequences.

Kits

In one embodiment, the invention encompasses a kit for performing any of the above described methods, wherein the kit comprises the mutant DNA polymerase of the invention or a functional fragment thereof.

In various embodiments, the kit comprises a nucleic acid primer with a 3'OH-end. In some embodiment, the nucleic acid primer is selected from the group consisting of: single-stranded DNA, double-stranded DNA with a 3'-OH single stranded over-hang and single-stranded RNA, In various embodiments, the kit comprises at least one divalent metal. In some embodiments, the divalent metal is manganese ($Mn^{2+}$), cobalt ($Co^{2+}$), magnesium ($Mg^{2+}$) or a combination thereof. In some embodiments, the divalent metal is manganese ($Mn^{2+}$), magnesium ($Mg^{2+}$) or a combination thereof.

In various embodiments, the kit comprises a mixture of nucleotides. In some embodiments, the nucleotides are natural deoxy-ribonucleotides, natural ribonucleotides, modified nucleotides or any combination of natural nucleotides and modified nucleotides. In some embodiments the deoxy-ribonucleotide is dATP, dGTP, dCTP, dATP, or dUTP. In some embodiments the ribonucleotide is ATP, GTP, CTP, or UTP. In certain non-limiting embodiments, the modified nucleotide may be cy3-dUTP, Digoxigenin-I I-dUTP, Biotin-16AA-dUTP, Texas Red-5-dCTP, Cyanine 3-AA-UTP, 4-Thio-UTP, Biotin-16-AA-dCTP, Ganciclovir Triphosphate, N6-(6-Azido)hexyl-adenosine-5'-triphosphate, 5-Hydroxymethyl-2'-deoxyuridine-5'-Triphosphate, 2'Fluoro-dUTP, 2'-Fluoro-dATP, 2'-Fluoro-dCTP, 2'-Fluoro-dGTP, 2'-Fluoro-dTTP, 2'-Amino-dATP, 2'-Amino-dTTP, 2'-Amino-dCTP, 2'-Amino-dGTP, 2'-Amino-dUTP; 2'-O-methyl-dUTP, 2'-O-methyl-dGTP, 2'-azido-2'-dATP, 2'-azido-2'-dUTP, 2'-azido-2'-dCTP, 2'-azido-2'-dGTP, 2'-O-methyl-ATP, 2'-O-methyl-CTP; 3'-azido-ddATP, 3'-azido-ddCTP, 3'-O-methyl-ATP, 3'-O-methyl-CTP, 3'-O-(2-nitrobenzyl)-2'-dATP, 3'-O—NH$_2$-dATP, 3'-O—NH$_2$-dTTP, 3'-O—NH$_2$-dCTP, 3'-O—NH$_2$-dGTP, 5-methyl-UTP, Ara-ATP (Vidarabine triphosphate), Ara-CTP (Cytarabine triphosphate), 2'-O-methyl-ATP, 2'-O-methyl-CTP, ϵ-ATP, 2-Aminopurine, FANA, and 5-ethynyl-UTP. Preferred modified nucleotides include: 2'-Fluoro-dUTP, 2'-Fluoro-dATP, 2'-Fluoro-dCTP, 2'-Fluoro-dGTP, 2'-Fluoro-dTTP, 2'-Amino-dATP, 2'-azido-2'-dATP, 2'-azido-2'-dUTP, 2'-azido-2'-dCTP, 2'-azido-2'-dGTP, 5-methyl-UTP, Ara-ATP (Vidarabine triphosphate), Ara-CTP (Cytarabine triphosphate), 2'-O-methyl-ATP, 2'-O-methyl-CTP, ϵ-ATP, 2-Aminopurine, FANA, 5-ethynyl-UTP, and reversible and irreversible 3'-modified nucleotide terminators as defined above.

In various embodiments, the kit comprises a reaction buffer.

In various embodiments, the kit comprises instructions for use.

Applications

The mutant DNA polymerase Pol theta of the present invention, or a functional fragment thereof, may be used in a wide variety of protocols and technologies. For example, in certain embodiment, the mutant DNA polymerase Pol theta of the present invention, or a functional fragment thereof, is used in the fields of molecular biology, genomics, transcriptomics, epigenetics, nucleic acid synthesis, nucleic acid sequencing, and the like. The mutant DNA polymerase Pol theta of the present invention, or a functional fragment thereof, can be used in many technology platforms, including but not limited to microarray, bead, and flow cytometry, and will useful in numerous applications, such as genomic research, drug target validation, drug discovery, diagnostic biomarker identification and therapeutic assessment.

EXAMPLES

Materials and Reagents

All chemicals and reagents were purchased from Sigma Aldrich (Saint-Quentin Fallavier, France) or Thermo Fisher scientifics (Courtaboeuf, France) and were of the highest purity. The commercial enzymes T4 Polynucleotide kinase, T4 DNA ligase and T4 RNA ligase 1 were obtained from New England Biolabs (NEB). The enzymes used for the nucleosides digestion, Benzonase® nuclease, Phosphodiesterase I from *Crotalus adamenteus* venom and alkaline Phosphatase from bovine intestinal mucosa were purchased from Sigma Aldrich.

Nucleotides Analogs

Commercial Nucleotides

The following nucleotides were purchased from Jena Bioscience: 5-ethynyl-UTP, 2-Aminopurine-riboside-5'-triphosphate, 2'-O-methyl-CTP, 2'-O-methyl-ATP, ara-CTP, ara-ATP, epsilon (ϵ)-ATP.

The following ones were purchased from Trilink Biotechnologies: 3'-Deoxynucleotide set (3'-dATP, 3'-dCTP, 3'-dGTP, 3'-Deoxy-5-methyl-UTP, 3'-dUTP), 5-methyl-UTP, ATP, CTP, UTP, GTP, 2-Fluoro-dATP, 2-Fluoro-dCTP 2'-Fluoro-dGTP, 2'-Fluoro-dTTP, 2'-Fluoro-dUTP, 2'-amino-dATP, 2'-amino-dUTP, 2'-amino-dCTP, 2'-amino-dCTP, 2'-amino-dGTP, 2'-O-methyl-dATP, 2'-O-methyl-dUTP, 2'-O-methyl-dCTP, 2'-O-methyl-dGTP, 2'-Azido-dATP, 2'-Azido-dUTP, 2'-Azido-dCTP, 2'-Azido-dGTP.

Custom Synthetic Nucleotides

FANA nucleotide was synthesized by M. Hollenstein from Institut Pasteur, Unité de Chimie Bioorganique des acides nucléiques, CNRS UMR 3523.

Protein Purification

WT Pol theta (Pol θ) (residues 1792-2590) was expressed from the pSUMO3[26] construct (from S. Doublié & S. Wallace, Addgene plasmid #78462) in BL21 CodonPlus (DE3) RIPL cells (Agilent technologies). The expression was carried out by autoinduction in Terrific broth EZMix™ supplemented with α-lactose (2 g/L), D-glucose (0.5 g/L), glycerol (8 ml.L$^{-1}$), 100 μg.mL$^{-1}$ of ampicillin and 50 μg.mL$^{-1}$ of chloramphenicol. 6 L of autoinducing medium were inoculated (starting OD$_{600}$, 0.05) and the culture was grown for 60 h at 20° C., with saturated cultures reaching a final OD$_{600}$ between 5 and 8. The following steps were performed at 4° C. Cells were harvested and resuspended at a ratio of 2.5-3 ml per gram of cell pellet in lysis buffer (50 mM HEPES pH 7.4, 300 mM NaCl, 10% glycerol, 1 mM TCEP, 5 mM Imidazole, 1.5% (v/v) IGEPAL C6-30, 5 mM CaCl$_2$, PIERCE™ EDTA-free protease inhibitor tablets and Benzonase® nuclease 500 U. Cell lysis was performed by using French press Cell-Disruptor at 20,000 psi. Following clarification by ultracentrifugation at 17,000 rpm for 1 h, two steps of column purification were performed. The supernatant was applied to a Ni-NTA resin through a His-Trap HP column (GE Healthcare Life sciences) which was equilibrated with buffer A (50 mM HEPES pH 7.4, 300 mM NaCl, 20 mM imidazole, 0.005% (v/v) IGEPAL C6-30, 1 mM TCEP, 10% (v/v) glycerol), and eluted with a gradient to 500 mM of imidazole with buffer B (50 mM HEPES pH 7.4, 300 mM NaCl, 500 mM Imidazole, 0.005% (v/v) IGEPAL C6-30, 1 mM TCEP, 10% (v/v) glycerol). Fractions from Ni-NTA chromatography containing pol θ were then applied to Heparin affinity chromatography after a two-fold dilution of the NaCl content with diluting buffer C (50 mM HEPES pH 7.4, 0.005% (v/v) IGEPAL C6-30, 1 mM TCEP, 10% (v/v) glycerol). The HiTrap Heparin column (GE Healthcare Life sciences) was equilibrated with buffer D (50 mM HEPES pH 7.4, 50 mM NaCl, 0.005% (v/v) IGEPAL C6-30, 1 mM TCEP, and 10% (v/v) glycerol) and eluted with a gradient to 2 M of NaCl with buffer E (50 mM HEPES pH 7.4, 2 M NaCl, 0.005% (v/v) IGEPAL C6-30, 1 mM TCEP, and 10% (v/v) glycerol). The protein fraction was then concentrated and frozen rapidly in a liquid nitrogen bath prior to storage at −80° C.

Generation of Mutants

Variant pol theta (pol θ) constructs were generated by site-directed mutagenesis by using the Quick-Change II XL kit (Agilent technologies) and were purified following the previously described protocol. The oligonucleotides used for the mutagenesis are listed in the supplementary Table II.

Oligonucleotides

Oligonucleotides were purchased from Eurogentec with RP-HPLC purity and dissolved in Nuclease-free water. Concentrations were measured by UV absorbance using the absorption coefficient ε at 260 nm provided by Eurogentec.

ssDNA Primer Radiolabelling

Oligonucleotides were labelled as follows: 40 μM of ssDNA primer (14-mer) were incubated with [γ-$^{32}$P]ATP (Perkin Elmer, 3000 Ci.mM$^{-1}$) and T4 polynucleotide kinase (New England Biolabs) for 1 hr at 37° C. in a total volume of 25 μL. The reaction was stopped by heating the T4 polynucleotide kinase at 75° C. for 10 min. 25 μM of label-free ssDNA primer was added to the mix and heated for 5 min up to 90° C., and slowly cooled to room temperature overnight.

Radioactive Nucleotidyltransferase Assay

5 μM of Pol θ was incubated with 50 nM of 5' $^{32}$P-labeled ssDNA for 0 to 30 min at 42° C. in the presence of 5 mM of MnCl$_2$ in a total volume of 10 μL of activity buffer (20 mM Tris pH 8, 150 mM NaCl, 10% glycerol, 0.01% IGEPAL C6-30, 0.1 mg.ml$^{-1}$ BSA). The reaction was started by addition of 500 μM of canonical or modified NTPs and stopped after 15 min at 42° C. by adding 10 mM EDTA and 98% formamide. The products of the reaction were resolved by gel electrophoresis on a 15% acrylamide gel and 8 M urea. The 0.4-mm wide gel was run for 3-4 hr at 40 V/cm and scanned by Storm 860 Molecular Dynamics phosphorimager (GE Healthcare).

Non-Radioactive Nucleotidyltransferase Assay

Different nucleotides ratios were tested in order to verify that each canonical ribonucleotide was equally incorporated by the polymerase. 5 μM of enzyme was incubated with 500 nM of non-labelled ssDNA primer (or ssDNA, or ssRNA primer labelled with ATTO488 at its 5'-end) and a ratio 1:1:1:1 of the four ribonucleotides (500 μM each) or with 500 μM of ATP, CTP and GTP, and 5 mM of UTP (1:1:1:10) or with 500 μM of ATP, CTP and GTP and 2.5 mM of UTP (1:1:1:5) or 500 μM of ATP and GTP and 2.5 mM of CTP and UTP (1:1:5:5). Additional mixtures were prepared with ATP/CTP and UTP/GTP (500 μM each). The reaction was performed in the same activity buffer in presence of 5 mM of MnCl$_2$ in a total volume of 100 μL. Synthetic RNA fragments were cleaned-up and used immediately for HPLC analysis and for RNA sequencing, for aptamer library construction, or stored at −80° C.

Hydrolysis of Synthetic RNA to Nucleosides and HPLC Analysis

Synthetic RNAs obtained after non-radioactive ssDNA primer extension were hydrolysed according to previous protocol[27] with slight modification. 5 to 80 μg of RNA were first cleaned-up by using the RNA Clean & concentrator™-5 kit (Zymo Research). The clean-up was carried out in two steps to allow the purification of small RNA fragments of size between 17 and 200 nt and at the same time large RNAs (>200 nt). The purified RNA pool was treated with Benzonase®nuclease (20 U), Phosphatase alkaline (1 U), Phosphodiesterase I (0.05 U) in 50 L of digestion buffer (50 mM Tris-HCl pH 8, 1 mM MgCl$_2$, 0.1 mg.mL$^{-1}$ BSA). The mix was incubated at 37° C. for 3 h and the digestion was kept up overnight at room temperature to insure a total lysis. Ribonucleosides were then cleaned-up by using a 10,000 MWCO Vivaspin®-500 centrifugal concentrator (Sartorius) and centrifuging for 10 min at 4° C. The filtrates were transferred to a 100 μL-vial insert tube to be further analyzed by HPLC. A Kromasil 100-5-C18 (150×4.6 mm) column (Sigma Aldrich) was used for HPLC analysis and the sample were eluted with a gradient of 0 to 20% of 10$^{-3}$ M Acetonitrile/TEAAc in 15 min. Solutions of 0.1 mM of the four ribonucleosides were injected as standards.

TruSeq RNA Library Preparation and Sequencing

We used 100 ng of total synthetic RNA and construct the sequencing libraries using the TruSeq Stranded mRNA LT Kit (Illumina, RS-122-2101, San Diego, Calif.) as recommended by the manufacturer, except that the fragmentation step was omitted. All the reagents were added to the reaction but the incubation at 94° C. was not performed. The directional libraries were controlled on Bioanalyzer DNA1000 Chips (Agilent Technologies, #5067-1504, Santa Clara, Calif.) and the concentration determined using the QuBit dsDNA HS kit (Q32854, Thermo Fisher Scientific). They were sequenced on an Illumina Hiseq 2500 sequencer using a HiSeq SR cluster kit v4 cBot HS (Illumina, # GD-401-4001) and a HiSeq SBS kit v4 50 cycles (Illumina, # FC-401-4002) in order to have around 50 millions single end reads of 65 bases per sample.

Different bases compositions were tested before RNA sequencing. A pool of the four nucleotides at a ratio of 1:1:1:1 (500 μM each, samples annotated as 'N') or with 500 μM of ATP, CTP and GTP, and 5 mM of UTP (ratio of 1:1:1:10, samples annotated as '10U') or with 500 μM of ATP, CTP and GTP and 2.5 mM of UTP (ratio of 1:1:1:5, sample annotated as '5U') or 500 μM of ATP and GTP and 2.5 mM of CTP and UTP (ratio of 1:1:5:5, sample annotated as '5U5C').

Statistical Analyses of TruSeq Reads

A FastQC analysis was ran in order to check the quality (Fret score) of the reads for each condition. Thus, statistical analyses were performed using R software v3.3.2, Shortread software v1.32.0 and Biostrings software v2.42.1. The software Cutadapt v1.14 was used to remove the TruSeq adapter sequences from the reads.

Aptamer Library Construction

The synthetic RNA pool, obtained after non-radioactive nucleotidyltransferase assay, was used to build the aptamer library. The RNA synthesis was stopped by the addition of 10 mM EDTA and the RNAs were cleaned-up with the RNA Clean & concentrator™-5 kit (#R1015, Zymo Research) according to the protocol recommended by the manufacturer for 17-200 nt RNA fragment purification. T4 RNA ligase I (#M0204L, New England Biolabs) has been used to ligate a 5'-phosphorylated ssRNA fragment labelled with Cy5 and preferably blocked at its 3'-end with ddC to avoid autoligation (oligonucleotide ligRNA-Cy5) to the newly synthesized RNAs (RNA acceptor labelled with ATT0488 at its 5' end). The reaction mixture comprised 1-20 pmol (preferably 10-20 pmol) of RNA acceptor and 5-40 pmol (preferably 20 pmol) of Cy5-ligRNA, 1 mM ATP, 15-25% (v/v) (preferably 20% (v/v) of PEG8000 and RNAsin 1U in a total volume of 20 μL of T4 RNA ligase I buffer supplied in the manufacturer kit (New England Biolabs). The mixture has been incubated for 16 h or overnight at 16° C.

The products of the reaction were resolved by gel electrophoresis on a 8% or 15% acrylamide gel and 8 M urea. The 0.4-mm wide gel was run for 3-4 hr at 40 V/cm and scanned by Typhoon imager (GE Healthcare). A double imaging has been performed by using Alexa488 filter, for the detection of the acceptor RNA length and by using Cy5 filter for the detection of the ligation of the Cy5-ligRNA. During SELEX (Systematic Evolution of Ligands by EXponential Enrichment) procedures it is critical to control the amplification step of nucleic acids aptamers that have bound to the molecule target. Indeed, it is important to have constant regions at 5'- and 3'-ends on either side of the randomized central sequence. These regions need to be useful for the reverse transcription reaction in order to obtain the complementary DNA and to perform PCR to enrich the pool for the next cycle. The same regions must also not interact or form undesirable secondary structures and influence the 3D conformation of the future aptamer.

CS13 and DW9 mutant exhibited a valuable ability to synthesize random sequence of RNAs by incorporating canonical or modified nucleotides to the 3'-ends of ssDNA fragments. The resulted pool of RNAs served as starting candidates for aptamer library. For that purpose, a fixed fragment of RNA was added to the end of each synthesized RNA. This fragment can serve as matrix strand to amplify the selected aptamer after each cycle of SELEX. The inventors decided to implement a ligation of the fixed fragment to each synthesized RNA by exploiting T4 RNA ligase I activity. The results indicate that the ligation of these fixed oligonucleotides occurs.

As explained just above, the 5'-end constant region of each synthetic RNA is constituted by the RNA (15-mer) or DNA primer (18-mer) used to initiate the elongation reaction. In a second step, the 3'-end constant region has been added by ligation of an RNA oligonucleotide after primer polymerization. The double fluorescence detection performed in the same gel allowed the observation of both the quality of the primer elongation (green fluorescence) and the efficiency of the ligation reaction (red fluorescence). The FIG. 13 presents the primer elongation rate of the DW9 mutant by adding natural ribonucleotides at 3'-end of a RNA primer. The lane 1 shows the fluorescence signals of both RNA primer (before elongation) and ligRNA (before ligation) and gave an idea of the quality of the signal detection obtained in the conditions of the assay. The lanes 2 to 6 display the elongation of the primer as a function of the incubation time (5 seconds to 15 minutes) and demonstrate an exponential increase of the length of the RNA with the duration of the incubation. The lanes 7 to 11 correspond to the same newly synthesized RNA that have acquired the 15-mer constant region by ligation. The efficiency of the ligation has been evaluated by the presence of both green and red fluorescence, resulting in a yellow colour along the gel and corresponding to a varied RNA fragment size. In addition, some thick band are observed at exactly +15, that corresponds to the ligation of the constant region to the non-elongated RNA primers that have remained in the reaction bulk. Finally, the lane 12 shows the absence of auto-ligation when the ligRNA fragments are in presence of T4 RNA ligase. Indeed, no band is visible except the "+0" that corresponds to the length of the ligRNA itself. This further demonstrates (or confirms) that it is possible to add a constant region to the synthetic RNA pool and that the RNA library can hence be screened or amplified for different applications, in particular for aptamer selection.

REFERENCES

1. DeVos, S. L. & Miller, T. M. Antisense oligonucleotides: treating neurodegeneration at the level of RNA. *Neurotherapeutics* 10, 486-97 (2013).
2. Crooke, S. T. *Antisense drug technology: principles, strategies, and applications.* (CRC Press, 2008).
3. Breaker, R. R. Riboswitches and the RNA world. *Cold Spring Harb. Perspect. Biol.* 4, a003566 (2012).
4. Walter, N. G. & Engelke, D. R. Ribozymes: catalytic RNAs that cut things, make things, and do odd and useful jobs. *Biologist (London).* 49, 199-203 (2002).
5. Diafa, S. & Hollenstein, M. Generation of Aptamers with an Expanded Chemical Repertoire. *Molecules* 20, 16643-16671 (2015).
6. Zhou, J. & Rossi, J. Aptamers as targeted therapeutics: current potential and challenges. *Nat Rev Drug Discov* 16, 440 (2017).
7. Mayer, G. The Chemical Biology of Aptamers. *Angew. Chemie Int. Ed.* 48, 2672-2689 (2009).
8. Lipi, F., Chen, S., Chakravarthy, M., Rakesh, S. & Veedu, R. N. In vitro evolution of chemically-modified nucleic acid aptamers: Pros and cons, and comprehensive selection strategies. *RNA Biol.* 13, 1232-1245 (2016).
9. Stoltenburg, R., Reinemann, C. & Strehlitz, B. SELEX—A (r)evolutionary method to generate high-affinity nucleic acid ligands. *Biomol. Eng.* 24, 381-403 (2007).
10. Delarue, M., Poch, O., Tordo, N., Moras, D. & Argos, P. An attempt to unify the structure of polymerases. "*Protein Eng. Des. Set* 3, 461-467 (1990).
11. Patel, P. H. & Loeb, L. A. Getting a grip on how DNA polymerases function. *Nat. Struct. Biol.* 8, 656-659 (2001).
12. Eom, S. H., Wang, J. & Steitz, T. A. Structure of Taq polymerase with DNA at the polymerase active site. *Nature* 382, 278-281 (1996).
13. Ellenberger, T., Doublié, S., Tabor, S., Long, A. M. & Richardson, C. C. Crystal structure of a bacteriophage T7 DNA replication complex at 2.2|[thinsp]|[[angst]|resolution. *Nature* 391, 251-258 (1998).
14. and, J. D. F. & Suo*, Z. Biochemical, Structural, and Physiological Characterization of Terminal Deoxynucleotidyl Transferase. (2006). doi:10.1021/CR040445W
15. Zahn, K. E., Averill, A. M., Aller, P., Wood, R. D. & Doublié, S. Human DNA polymerase θ grasps the primer terminus to mediate DNA repair. *Nat. Struct. Mol. Biol.* 22, 304-311 (2015).
16. Wood, R. D. & Doublié, S. DNA polymerase θ (POLQ), double-strand break repair, and cancer. *DNA Repair (Amst).* 44, 22-32 (2016).
17. Longley, M. J., Prasad, R., Srivastava, D. K., Wilson, S. H. & Copeland, W. C. Identification of 5'-deoxyribose phosphate lyase activity in human DNA polymerase gamma and its role in mitochondrial base excision repair in vitro. *Proc. Natl. Acad. Sci. U.S.A.* 95, 12244-8 (1998).
18. Kent, T., Mateos-Gomez, P. A., Sfeir, A. & Pomerantz, R. T. Polymerase θ is a robust terminal transferase that oscillates between three different mechanisms during end-joining. *Elife* 5, (2016).
19. Black, S. J., Kashkina, E., Kent, T. & Pomerantz, R. T. DNA Polymerase θ: A Unique Multifunctional End-Joining Machine. *Genes (Basel).* 7, 67 (2016).
20. Andrade, P., Martin, M. J., Juarez, R., Lopez de Saro, F. & Blanco, L. Limited terminal transferase in human DNA polymerase defines the required balance between accuracy and efficiency in NHEJ. *Proc. Natl. Acad. Sci.* 106, 16203-16208 (2009).
21. Ramadan, K. et al. Human DNA Polymerase γ Possesses Terminal Deoxyribonucleotidyl Transferase Activity And Can Elongate RNA Primers: Implications for Novel Functions. *J. Mol. Biol.* 328, 63-72 (2003).
22. Loc'h, J., Rosario, S. & Delarue, M. Structural Basis for a New Templated Activity by Terminal Deoxynucleotidyl Transferase: Implications for V(D)J Recombination. *Structure* (2016). doi:10.1016/j.str.2016.06.014
23. Gouge, J. et al. Structural basis for a novel mechanism of DNA bridging and alignment in eukaryotic DSB DNA repair. *EMBO J.* 34, 1126-42 (2015).

24. Boulé, J.-B., Rougeon, F. & Papanicolaou, C. Terminal Deoxynucleotidyl Transferase Indiscriminately Incorporates Ribonucleotides and Deoxyribonucleotides. *J. Biol. Chem.* 276, 31388-31393 (2001).
25. Delarue, M. et al. Crystal structures of a template-independent DNA polymerase: murine terminal deoxynucleotidyltransferase. *EMBO J.* 21, 427-39 (2002).
26. Patel, P. H. & Loeb, L. A. DNA polymerase active site is highly mutable: evolutionary consequences. *Proc. Natl. Acad. Sci. U.S.A.* 97, 5095-100 (2000).
27. Li, Y., Korolev, S. & Waksman, G. Crystal structures of open and closed forms of binary and ternary complexes of the large fragment of Thermus aquaticus DNA polymerase I: structural basis for nucleotide incorporation. *EMBO J.* 17, 7514-25 (1998).
28. Hogg, M., Seki, M., Wood, R. D., Doublié, S. & Wallace, S. S. Lesion Bypass Activity of DNA Polymerase θ (POLQ) Is an Intrinsic Property of the Pol Domain and Depends on Unique Sequence Inserts. *J. Mol. Biol.* 405, 642-652 (2011).
29. Ong, J. L., Loakes, D., Jaroslawski, S., Too, K. & Holliger, P. Directed Evolution of DNA Polymerase, RNA Polymerase and Reverse Transcriptase Activity in a Single Polypeptide. *J. Mol. Biol.* 361, 537-550 (2006).
30. Su, D. et al. Quantitative analysis of ribonucleoside modifications in tRNA by HPLC-coupled mass spectrometry. *Nat. Protoc.* 9, 828-841 (2014).
31. Charlton, J. & Smith, D. Estimation of SELEX pool size by measurement of DNA renaturation rates. *RNA* 5, 1326-32 (1999).
32. Bunka, D. H., Platonova, O. & Stockley, P. G. Development of aptamer therapeutics. *Curr. Opin. Pharmacol.* 10, 557-562 (2010).
33. Lauridsen, L. H., Rothnagel, J. A. & Veedu, R. N. Enzymatic Recognition of 2'-Modified Ribonucleoside 5'-Triphosphates: Towards the Evolution of Versatile Aptamers. *ChemBioChem* 13, 19-25 (2012).
34. Diafa, S. & Hollenstein, M. Generation of Aptamers with an Expanded Chemical Repertoire. *Molecules* 20, 16643-16671 (2015).
35. Pieken, W. A., Olsen, D. B., Benseler, F., Aurup, H. & Eckstein, F. Kinetic characterization of ribonuclease-resistant 2'-modified hammerhead ribozymes. *Science* 253, 314-7 (1991).
36. Rhie, A. et al. Characterization of 2'-Fluoro-RNA Aptamers That Bind Preferentially to Disease-associated Conformations of Prion Protein and Inhibit Conversion. *J. Biol. Chem.* 278, 39697-39705 (2003).
37. Ono, T., Scalf, M. & Smith, L. M. 2'-Fluoro modified nucleic acids: polymerase-directed synthesis, properties and stability to analysis by matrix-assisted laser desorption/ionization mass spectrometry. *Nucleic Acids Res.* 25, 4581-4588 (1997).
38. Dellafiore, M. A., Montserrat, J. M. & Iribarren, A. M. Modified Nucleoside Triphosphates for In-vitro Selection Techniques. *Front. Chem.* 4, 18 (2016).
39. Alves Ferreira-Bravo, I., Cozens, C., Holliger, P. & DeStefano, J. J. Selection of 2'-deoxy-2'-fluoroarabinonucleotide (FANA) aptamers that bind HIV-1 reverse transcriptase with picomolar affinity. *Nucleic Acids Res.* 43, 9587-99 (2015).
40. Malaby, A. W., Martin, S. K., Wood, R. D. & Doublié, S. in *DNA Repair Enzymes: Structure, Biophysics, and Mechanism* (ed. Eichman, B. F. B. T.-M. in E.) 592, 103-121 (Academic Press, 2017).
41. Zan, H. et al. The translesion DNA polymerase theta plays a dominant role in immunoglobulin gene somatic hypermutation. *EMBO J.* 24, 3757-69 (2005).
42. Seki, M., Marini, F. & Wood, R. D. POLQ (Pol), a DNA polymerase and DNA-dependent ATPase in human cells. *Nucleic Acids Res.* 31, 6117-6126 (2003).
43. Yousefzadeh, M. J. et al. Mechanism of Suppression of Chromosomal Instability by DNA Polymerase POLQ. *PLoS Genet.* 10, e1004654 (2014).
44. Kent, T. et al. Polymerase θ is a robust terminal transferase that oscillates between three different mechanisms during end-joining. *Elife* 5, 16203-16208 (2016).
45. Vashishtha, A. K., Wang, J. & Konigsberg, W. H. Different Divalent Cations Alter the Kinetics and Fidelity of DNA Polymerases. *J. Biol. Chem.* 291, 20869-20875 (2016).
46. Stark, M. R., Pleiss, J. A., Deras, M., Scaringe, S. A. & Rader, S. D. An RNA ligase-mediated method for the efficient creation of large, synthetic RNAs. *RNA* 12, 2014-9 (2006).
47. Arai, H., Nishigaki, K., Nemoto, N., Suzuki, M. & Husimi, Y. Characterization of Norovirus RNA replicase for in vitro amplification of RNA. *BMC Biotechnol.* 2013 131 13, 85 (2013).

TABLE I

Ribonucleoside composition of the synthesized RNA after enzymatic digestion

| | | C ($\varepsilon$ = 9000) | G ($\varepsilon$ = 13700) | A ($\varepsilon$ = 15400) | U ($\varepsilon$ = 10000) |
|---|---|---|---|---|---|
| Internal standards | Area (mAU * s) | 514.2 | 2370.0 | 1316.8 | 510.8 |
| | injected amount (pmol) | 114 | 346 | 171 | 102 |
| Sample with NTPs (1:1:1:1) | Area (mAU * s) | 2665 | 7812 | 3394 | 2671 |
| | injected amount (pmol) | 592.2 | 1140.3 | 440.6 | 534.0 |
| | % of total ribonucleoside amount | 21.0 | 40.5 | 15.7 | 19.0 |
| Sample with NTPs (1:1:1:10) | Area (mAU * s) | 7761.2 | 16149.6 | 10652.3 | 23444.2 |
| | injected amount (pmol) | 1724.7 | 2357.5 | 1383.4 | 4688.8 |
| | % of total ribonucleoside amount | 17.9 | 24.4 | 14.3 | 48.6 |
| Sample with ATP/CTP (1:1) | Area (mAU * s) | 2922.3 | | 1808.5 | |
| | injected amount (pmol) | 401.8 | | 379.5 | |
| | % of total ribonucleoside amount | 49.4 | | 46.6 | |
| Sample with UTP/GTP (1:1) | Area (mAU * s) | | 3393.5 | | 1491.8 |
| | injected amount (pmol) | | 495.3 | | 298.2 |
| | % of total ribonucleoside amount | | 56.8 | | 34.2 |

TABLE II

Oligonucleotides used in this study

| Primer Name | Sequence (5,-3) | SEQ ID NO: |
|---|---|---|
| CS13-fw | TGACTACTCTCAGCTTGGACTGAGGATCTTGGCTC | SEQ ID NO: 16 |
| CS13-rv | GAGCCAAGATCCTCAGTCCAAGCTGAGAGTAGTCA | SEQ ID NO: 17 |
| GC10-fw | CATGCCTTTGTGCCTTTCGTAGGTGGTTCAATACTGGC | SEQ ID NO: 18 |
| GC10-rv | GCCAGTATTGAACCACCTACGAAAGGCACAAAGGCATG | SEQ ID NO: 19 |
| NM11-fw | GCAGCAGGCAAAACAGATTTGCTTTGAGGTCATTTATGG | SEQ ID NO: 20 |
| NM11-rv | CCATAAATGATCCTCAAAGCAAATCTGTTTTGCCTGCTGC | SEQ ID NO: 21 |
| DW9-fw | GGCTGCTGACTACTCTCAGATGGGACTGAGGATCTTGGCTCAT | SEQ ID NO: 22 |
| DW9-rv | ATGAGCCAAGATCCTCAGTCCCATCTGGAAGTAGTCAGCAGCC | SEQ ID NO: 23 |
| MC15-fw | AGGTGGTTCAATACTGGTTGCTGACTACTCTCACG | SEQ ID NO: 24 |
| MC15-rv | GCTGAGAGTAGTCAGCAACCAGTATTGAACCACCT | SEQ ID NO: 25 |
| ssDNAp | TACGCATTAGCATA | SEQ ID NO: 13 |
| ATTO[488]-ssDNAp | ATTO[488]-TACGCATTAGCATA | SEQ ID NO: 13 |
| ligRNA-Cy5 | 5'P-UUAUGCUAAUGUCCC-Cy5 | SEQ ID NO: 15 |
| ini-RNA | GGGACAUUAGCAUAA | SEQ ID No: 26 |

The invention claimed is:

1. A host cell comprising a DNA vector comprising a nucleotide sequence encoding the mutant DNA polymerase wherein the host cell is selected from the group consisting of the host cells deposited at the Collection Nationale de Cultures de Microorganismes (CNCM) at the Institut Pasteur, 25, Rue du Docteur Roux, 75724 Paris, FR, on Sep. 14, 2017 under the deposit number CNCM I-5238 (*E. coli* Δ1-1791_CS13), CNCM I-5239 (*E. coli* Δ1-1791_DW9), CNCM I-5240 (*E. coli* Δ1-1791_MC15) and CNCM I-5241 (*E. coli* Δ1-1791_NM11).

2. A method for producing degenerate or random nucleotide sequences comprising incubating a mutant DNA polymerase with nucleotide triphosphates under conditions that allow degenerate or random nucleotide incorporation to produce degenerate or random nucleotide sequences;
wherein the mutant DNA polymerase is a DNA polymerase of the Pol theta (Pol theta) subfamily capable of performing non tem plated nucleic acid extension;
wherein the mutant DNA polymerase is at least 90% identical to SEQ ID NO: 1; and
wherein the mutant DNA polymerase comprises at least one amino acid substitution at a position selected from the group consisting of: 2322, 2328, 2334, 2335, 2384, 2387 and 2391, the indicated positions being determined by alignment with SEQ ID NO: 1.

3. The method of claim 2, further comprising adding a fixed nucleotide sequence to the 3' end of the degenerate or random nucleotide sequences.

4. The method of claim 2, further comprising amplifying the degenerate or random nucleotide sequences, and eventually further comprising cloning the amplified sequences into a vector to generate a library of degenerate or random nucleotide sequences.

5. The method of claim 2, wherein the mutant DNA polymerase is at least 95% identical to SEQ ID NO: 1.

6. The method of claim 2, wherein the at least one amino acid substitution in the mutant DNA polymerase is selected from the group consisting of: a Proline (P) to an aliphatic amino acid or a polar amino acid substitution at position 2322, an Alanine (A) to an aliphatic amino acid or a polar amino acid substitution at position 2328, a Leucine (L) to an aliphatic amino acid substitution at position 2334, a Glutamic acid (E) to an aliphatic amino acid or a polar amino acid substitution at position 2335, a Glutamine (Q) to an aliphatic amino acid or a polar amino acid substitution at position 2384, a Tyrosine (Y) to an aromatic amino acid or an aliphatic amino acid substitution at position 2387, and a Tyrosine (Y) to an aromatic amino acid or an aliphatic amino acid substitution at position 2391, the indicated positions being determined by alignment with SEQ ID NO: 1.

7. The method of claim 2, wherein the amino acid at position 2322 of the mutant DNA polymerase is substituted by an aliphatic amino acid selected from the group consisting of: Valine (V) and Alanine (A) or by a polar amino acid selected from the group consisting of: Threonine (T) and Serine (S), the indicated position being determined by alignment with SEQ ID NO: 1.

8. The method of claim 2, wherein the amino acid at position 2328 of the mutant DNA polymerase is substituted by an aliphatic amino acid selected from the group consisting of: Valine (V) and Glycine (G) or by a polar amino acid selected from the group consisting of: Threonine (T) and Serine (S), the indicated position being determined by alignment with SEQ ID NO: 1.

9. The method of claim 2, wherein the amino acid at position 2334 of the mutant DNA polymerase is substituted by an aliphatic amino acid selected from the group consisting of: Methionine (M), Isoleucine (I) and Alanine (A), the indicated position being determined by alignment with SEQ ID NO: 1.

10. The method of claim 2, wherein the amino acid at position 2335 of the mutant DNA polymerase is substituted by an aliphatic amino acid selected from the group consisting of: Glycine (G) and Alanine (A) or by a polar amino acid selected from the group consisting of: Threonine (T) and Serine (S), the indicated position being determined by alignment with SEQ ID NO: 1.

11. The method of claim 2, wherein the amino acid at position 2384 of the mutant DNA polymerase is substituted by an Alanine (A) or by a polar amino acid selected from the group consisting of: Asparagine (N), Serine (S) and Threonine (T), the indicated position being determined by alignment with SEQ ID NO: 1.

12. The method of claim 2, wherein the amino acid at position 2387 of the mutant DNA polymerase is substituted by an aromatic amino acid selected from the group consisting of: Phenylalanine (F) and Tryptophan (W) or by an aliphatic amino acid selected from the group consisting of: Alanine (A) and Valine (V), the indicated position being determined by alignment with SEQ ID NO: 1.

13. The method of claim 2, wherein the amino acid at position 2391 of the mutant DNA polymerase is substituted by an aromatic amino acid selected from the group consisting of: Phenylalanine (F) and Tryptophan (W) or by an aliphatic amino acid selected from the group consisting of: Alanine (A) and Valine (V), the indicated position being determined by alignment with SEQ ID NO: 1.

14. The method of claim 2, wherein the at least one amino acid substitution of the mutant DNA polymerase is selected from the group consisting of: P to V substitution at position 2322 (P2322V), A to V substitution at position 2328 (A2328V), L to M substitution at position 2334 (L2334M), E to G substitution at position 2335 (E2335G), Q to N at position 2384 (Q2384N), Y to F substitution at position 2387 (Y2387F); and Y to F substitution at position 2391 (Y2391F), the indicated positions being determined by alignment with SEQ ID NO: 1.

15. The method of claim 14, wherein the at least one amino acid substitution of the mutant DNA polymerase is selected from the group consisting of: P to V substitution at position 2322 (P2322V), A to V substitution at position 2328 (A2328V), L to M substitution at position 2334 (L2334M), E to G substitution at position 2335 (E2335G), and Y to F substitution at position 2387 (Y2387F), the indicated positions being determined by alignment with SEQ ID NO: 1.

16. The method of claim 2, wherein the mutant DNA polymerase comprises a single amino acid substitution selected from the group consisting of: P to V substitution at position 2322 (P2322V), A to V substitution at position 2328

(A2328V), L to M substitution at position 2334 (L2334M), E to G substitution at position 2335 (E2335G), Q to N at position 2384 (Q2384N), Y to F substitution at position 2387 (Y2387F), and Y to F substitution at position 2391 (Y2391F), the indicated positions being determined by alignment with SEQ ID NO: 1.

17. The method of claim 2, wherein the mutant DNA polymerase comprises a double amino acid substitution L2334M and E2335G, the indicated positions being determined by alignment with SEQ ID NO: 1.

* * * * *